(12) United States Patent
Bayley et al.

(10) Patent No.: US 9,758,953 B2
(45) Date of Patent: Sep. 12, 2017

(54) BASIN AND HAND DRYING SYSTEM

(71) Applicant: Bradley Fixtures Corporation, Menomonee Falls, WI (US)

(72) Inventors: Graeme S. Bayley, Brookfield, WI (US); Mark A. Figurski, Harland, WI (US); Kenneth A. Kreitzer, Espoo (FI); Jason M. Renner, Greenfield, WI (US); Jon A. Dommisse, West Bend, WI (US); Terry Lee McCallum, Milwaukee, WI (US)

(73) Assignee: Bradley Fixtures Corporation, Menomonee Falls, WI (US)

( * ) Notice: Subject to any disclaimer, the term of this patent is extended or adjusted under 35 U.S.C. 154(b) by 308 days.

(21) Appl. No.: 14/386,401

(22) PCT Filed: Mar. 14, 2013

(86) PCT No.: PCT/US2013/031171
§ 371 (c)(1),
(2) Date: Sep. 19, 2014

(87) PCT Pub. No.: WO2013/142224
PCT Pub. Date: Sep. 26, 2013

(65) Prior Publication Data
US 2015/0052678 A1    Feb. 26, 2015

Related U.S. Application Data

(60) Provisional application No. 61/620,541, filed on Apr. 5, 2012, provisional application No. 61/613,821, filed on Mar. 21, 2012.

(51) Int. Cl.
*E03C 1/181* (2006.01)
*A47K 5/12* (2006.01)
(Continued)

(52) U.S. Cl.
CPC ............... *E03C 1/181* (2013.01); *A47K 5/12* (2013.01); *A47K 10/48* (2013.01); *A61L 2/10* (2013.01);
(Continued)

(58) Field of Classification Search
CPC ....... A47K 10/48; A47K 5/12; A47K 2210/00
See application file for complete search history.

(56) References Cited

U.S. PATENT DOCUMENTS

| 540,235 A | 6/1895 | Clifford et al. |
| D30,136 S | 2/1899 | Eckerson |

(Continued)

FOREIGN PATENT DOCUMENTS

| AT | 141398 | 8/1996 |
| AU | 2005203363 | 2/2006 |

(Continued)

*Primary Examiner* — Janie Loeppke
(74) *Attorney, Agent, or Firm* — Boyle Fredrickson, S.C.

(57) ABSTRACT

A basin and hand drying system includes a hand dryer attached to a basin. The hand dryer includes a top air plenum and a bottom air plenum. The air plenums include a plurality of air outlets that direct pressurized air from a blower motor for hand drying. A soap dispenser and faucet mount on the basin for dispensing liquefied soap and water for hand washing.

20 Claims, 31 Drawing Sheets

(51) Int. Cl.
  *A47K 10/48* (2006.01)
  *E03C 1/05* (2006.01)
  *A61L 2/10* (2006.01)
  *A61L 2/232* (2006.01)
  *A61L 2/24* (2006.01)
  *A61L 9/16* (2006.01)
  *A61L 2/14* (2006.01)

(52) U.S. Cl.
  CPC .................. *A61L 2/232* (2013.01); *A61L 2/24* (2013.01); *A61L 9/16* (2013.01); *E03C 1/057* (2013.01); *A47K 2210/00* (2013.01); *A61L 2/14* (2013.01); *A61L 2202/14* (2013.01); *A61L 2209/111* (2013.01); *A61L 2209/14* (2013.01)

(56) References Cited

U.S. PATENT DOCUMENTS

| | | |
|---|---|---|
| D36,574 S | 2/1899 | Zipp |
| D36,575 S | 10/1903 | Zipp |
| D36,595 S | 10/1903 | Peet |
| 937,509 A | 10/1909 | Carpenter |
| 1,069,972 A | 8/1913 | Metzaer |
| 1,323,398 A | 12/1919 | Leland |
| 1,419,712 A | 6/1922 | Bassette |
| 1,423,800 A | 7/1922 | Hibbard et al. |
| 1,494,883 A | 5/1924 | Bassette et al. |
| 1,578,047 A | 3/1926 | Lum |
| 1,579,705 A | 4/1926 | Hewitt |
| 1,616,313 A | 2/1927 | Farmer |
| 1,659,851 A | 2/1928 | Brewington |
| 1,750,094 A | 3/1930 | Emmrich |
| 1,765,915 A | 6/1930 | Haase |
| D81,754 S | 8/1930 | Mabee |
| 1,816,055 A | 7/1931 | Pfeifer |
| 1,961,179 A | 6/1934 | Tinkham |
| 1,997,387 A | 4/1935 | McCord |
| 2,008,183 A | 7/1935 | McCord |
| 2,027,605 A | 5/1936 | McCord et al. |
| 2,041,352 A | 5/1936 | Jordan |
| D100,310 S | 7/1936 | Blu |
| 2,130,196 A | 9/1938 | Sakier |
| 2,192,383 A | 3/1940 | Krolop |
| 2,202,107 A | 5/1940 | Korn |
| 2,281,370 A | 4/1942 | Morrison et al. |
| 2,328,129 A | 8/1943 | Earle |
| 2,438,762 A | 3/1948 | McLeckie |
| 2,470,187 A | 5/1949 | Price |
| 2,479,571 A | 8/1949 | Hewitt |
| 2,498,699 A | 2/1950 | Mullett et al. |
| 2,504,740 A | 4/1950 | Siegel |
| 2,521,769 A | 9/1950 | Arcularrus |
| 2,537,821 A | 1/1951 | Fodor |
| 2,591,669 A | 4/1952 | Bucknell et al. |
| 2,606,274 A | 8/1952 | Spierer |
| RE23,674 E | 6/1953 | Spierer et al. |
| 2,641,679 A | 6/1953 | Brodbeck |
| 2,646,629 A | 7/1953 | Clemens |
| D170,204 S | 8/1953 | Long |
| 2,651,705 A | 9/1953 | Clemens |
| 2,666,837 A | 1/1954 | Brodbeck |
| 2,677,041 A | 4/1954 | Oliver et al. |
| 2,698,894 A | 1/1955 | Stein |
| 2,714,151 A | 7/1955 | Becker |
| 2,761,222 A | 9/1956 | Bennett |
| 2,767,407 A | 10/1956 | Weiss |
| 2,777,934 A | 1/1957 | Falkenthal |
| 2,826,763 A | 3/1958 | Bass |
| 2,837,835 A | 6/1958 | Hewitt et al. |
| 2,853,591 A | 9/1958 | Fine |
| 2,853,592 A | 9/1958 | Gravet |
| 2,859,535 A | 11/1958 | Carlson |
| 2,906,627 A | 9/1959 | Payton et al. |
| 2,908,019 A | 10/1959 | Lyon, Jr. |
| 2,965,906 A | 12/1960 | Mullett et al. |
| 2,977,455 A | 3/1961 | Murphy |
| 3,059,815 A | 10/1962 | Parsons, Jr. |
| 3,065,473 A | 11/1962 | Sporck et al. |
| 3,076,887 A | 2/1963 | Bulow |
| 3,128,161 A | 4/1964 | Hudon |
| D201,493 S | 6/1965 | Sundberg et al. |
| 3,220,424 A | 11/1965 | Nelson |
| 3,305,938 A | 2/1967 | Arthur |
| D210,131 S | 2/1968 | Rourke |
| 3,384,977 A | 5/1968 | Rosenberg |
| 3,409,995 A | 11/1968 | Greenwood et al. |
| 3,415,278 A | 12/1968 | Yamamoto of al. |
| 3,449,838 A | 6/1969 | Chancellor |
| 3,480,787 A | 11/1969 | Johansen |
| 3,487,477 A | 1/1970 | Classen |
| 3,491,381 A | 1/1970 | Catheart |
| 3,502,384 A | 3/1970 | Gipson |
| 3,505,692 A | 4/1970 | Forbes |
| 3,523,305 A | 8/1970 | Zorn |
| 3,536,294 A | 10/1970 | Rodriguez |
| 3,551,919 A | 1/1971 | Forbes |
| 3,556,158 A | 1/1971 | Schneider |
| 3,575,583 A | 4/1971 | Brown |
| 3,575,640 A | 4/1971 | Ishikawa |
| 3,576,277 A | 4/1971 | Blackman |
| 3,585,652 A | 6/1971 | Forbes et al. |
| 3,585,653 A | 6/1971 | Forbes et al. |
| 3,587,177 A | 6/1971 | Overly et al |
| 3,588,038 A | 6/1971 | Tanaka |
| 3,603,002 A | 9/1971 | Spierer |
| 3,613,124 A | 10/1971 | Ichimori et al. |
| 3,621,199 A | 11/1971 | Goldstein |
| 3,639,920 A | 2/1972 | Griffin et al. |
| 3,643,346 A | 2/1972 | Lester |
| 3,699,984 A | 10/1972 | Davis |
| 3,724,001 A | 4/1973 | Ichimori et al. |
| 3,744,149 A | 7/1973 | Helbling |
| 3,746,035 A | 7/1973 | Singer |
| 3,757,806 A | 9/1973 | Bhaskar et al. |
| 3,817,651 A | 6/1974 | Law et al. |
| 3,878,621 A | 4/1975 | Duerre |
| 3,904,167 A | 9/1975 | Touch et al. |
| 3,906,795 A | 9/1975 | Kask |
| 3,918,987 A | 11/1975 | Kopfer |
| D238,075 S | 12/1975 | Harris |
| 3,975,781 A | 8/1976 | Klimboff et al. |
| 3,992,730 A | 11/1976 | Davis |
| 4,072,157 A | 2/1978 | Wines, Jr. et al. |
| 4,120,180 A | 10/1978 | Jedora |
| 4,144,596 A | 3/1979 | MacFarlane et al. |
| 4,145,602 A | 3/1979 | Lee |
| 4,145,769 A | 3/1979 | MacFarlane et al. |
| D251,795 S | 5/1979 | McCann |
| 4,193,209 A | 3/1980 | Lovison et al. |
| 4,195,416 A | 4/1980 | Hall |
| 4,219,367 A | 8/1980 | Cary, Jr. et al. |
| 4,239,555 A | 12/1980 | Scharlack et al. |
| 4,256,133 A | 3/1981 | Coward et al. |
| D260,678 S | 9/1981 | Hiller |
| 4,295,233 A | 10/1981 | Hinkel et al. |
| 4,309,781 A | 1/1982 | Lissau |
| 4,336,619 A | 6/1982 | Hinkel et al. |
| 4,375,874 A | 3/1983 | Leotta et al. |
| 4,383,377 A | 5/1983 | Crafton |
| 4,398,310 A | 8/1983 | Lienhard |
| 4,402,095 A | 9/1983 | Pepper |
| 4,402,331 A | 9/1983 | Taldo et al. |
| D272,263 S | 1/1984 | Lienhard |
| 4,429,422 A | 2/1984 | Warcham |
| 4,453,286 A | 6/1984 | Weiland |
| 4,461,439 A | 7/1984 | Rose |
| 4,497,999 A | 2/1985 | Postbeschild |
| 4,509,543 A | 4/1985 | Livingston et al. |
| D279,404 S | 6/1985 | Hiller |
| 4,520,516 A | 6/1985 | Parsons |
| 4,541,563 A | 9/1985 | Uetsuhara |
| 4,570,823 A | 2/1986 | Arabian et al. |
| 4,594,797 A | 6/1986 | Houck, Jr. |

(56) References Cited

U.S. PATENT DOCUMENTS

| | | |
|---|---|---|
| 4,598,726 A | 7/1986 | Pepper |
| 4,604,764 A | 8/1986 | Enzo |
| 4,606,085 A | 8/1986 | Davies |
| 4,610,165 A | 9/1986 | Duffy et al. |
| 4,611,768 A | 9/1986 | Voss et al. |
| 4,624,017 A | 11/1986 | Foletta |
| 4,637,254 A | 1/1987 | Dyben et al. |
| 4,642,821 A | 2/1987 | Zanuso et al. |
| 4,642,909 A | 2/1987 | Garcial |
| 4,644,256 A | 2/1987 | Farias et al. |
| 4,651,777 A | 3/1987 | Hardman |
| 4,653,201 A | 3/1987 | Seaman |
| 4,670,010 A | 6/1987 | Dragone |
| 4,671,121 A | 6/1987 | Schieler |
| 4,681,141 A | 7/1987 | Wang |
| 4,682,628 A | 7/1987 | Hill |
| 4,685,222 A | 8/1987 | Houck, Jr. |
| 4,688,277 A | 8/1987 | Kakinoki et al. |
| 4,688,585 A | 8/1987 | Vetter |
| 4,700,049 A | 10/1987 | Rubin |
| 4,702,107 A | 10/1987 | Guerrini et al. |
| 4,707,867 A | 11/1987 | Kawabe et al. |
| 4,707,933 A | 11/1987 | Keck et al. |
| 4,709,728 A | 12/1987 | Ying-Chung |
| 4,716,605 A | 1/1988 | Shepherd et al. |
| 4,722,372 A | 2/1988 | Hoffman et al. |
| 4,735,002 A | 4/1988 | Rath |
| 4,735,357 A | 4/1988 | Gregory et al. |
| 4,741,363 A | 5/1988 | Hu |
| 4,742,583 A | 5/1988 | Yoshida et al. |
| 4,742,836 A | 5/1988 | Buehler |
| 4,744,515 A | 5/1988 | Watanabe |
| 4,746,090 A | 5/1988 | Hamilton |
| 4,762,273 A | 8/1988 | Gregory et al. |
| 4,765,003 A | 8/1988 | Chang |
| 4,767,922 A | 8/1988 | Stauffer |
| 4,769,863 A | 9/1988 | Tegg et al. |
| 4,780,595 A | 10/1988 | Alban |
| 4,785,162 A | 11/1988 | Kuo |
| 4,823,414 A | 4/1989 | Piersimoni et al. |
| 4,826,129 A | 5/1989 | Fong et al. |
| 4,839,039 A | 6/1989 | Parsons et al. |
| 4,848,599 A | 7/1989 | Kano et al. |
| 4,852,802 A | 8/1989 | Iggulden et al. |
| 4,856,122 A | 8/1989 | Pilolla |
| 4,857,112 A | 8/1989 | Franninge |
| 4,857,705 A | 8/1989 | Blevins |
| 4,872,485 A | 10/1989 | Laverty, Jr. |
| 4,876,435 A | 10/1989 | Hawkins |
| 4,882,467 A | 11/1989 | Dimick |
| 4,883,749 A | 11/1989 | Roberts et al. |
| 4,889,315 A | 12/1989 | Imanaga |
| 4,894,874 A | 1/1990 | Wilson |
| 4,909,580 A | 3/1990 | Mitchell |
| 4,914,758 A | 4/1990 | Shaw |
| 4,914,833 A | 4/1990 | Pilolla et al. |
| 4,915,347 A | 4/1990 | Iqbal et al. |
| 4,916,382 A | 4/1990 | Kent |
| 4,916,613 A | 4/1990 | Lange et al. |
| 4,921,129 A | 5/1990 | Jones et al. |
| 4,921,131 A | 5/1990 | Binderbauer et al. |
| 4,921,211 A | 5/1990 | Novak et al. |
| 4,940,298 A | 7/1990 | Jackson et al. |
| 4,941,219 A | 7/1990 | Van Marcke |
| 4,942,631 A | 7/1990 | Rosa |
| 4,948,090 A | 8/1990 | Chen |
| 4,953,236 A | 9/1990 | Lee et al. |
| 4,954,179 A | 9/1990 | Franninge |
| 4,955,535 A | 9/1990 | Tsutsui et al. |
| 4,959,603 A | 9/1990 | Yamamoto et al. |
| 4,963,780 A | 10/1990 | Hochstrasser |
| 4,967,425 A | 11/1990 | Kawamura et al. |
| 4,971,106 A | 11/1990 | Tsutsui et al. |
| 4,980,474 A | 12/1990 | Hayasjo et al. |
| 4,980,574 A | 12/1990 | Cirrito |
| 4,984,314 A | 1/1991 | Weigert |
| 4,986,221 A | 1/1991 | Shaw |
| 4,989,755 A | 2/1991 | Shiau |
| 4,993,172 A * | 2/1991 | Allen ............... A47K 10/48 34/202 |
| 4,995,585 A | 2/1991 | Gruber et al. |
| 4,998,673 A | 3/1991 | Pilolla |
| 5,000,044 A | 3/1991 | Duffy et al. |
| 5,008,963 A | 4/1991 | Stein |
| 5,018,550 A | 5/1991 | Burdorff |
| 5,025,516 A | 6/1991 | Wilson |
| 5,031,258 A | 7/1991 | Shaw |
| 5,031,337 A | 7/1991 | Pilolla et al. |
| 5,033,508 A | 7/1991 | Laverty, Jr. |
| 5,033,715 A | 7/1991 | Chiang et al. |
| 5,060,323 A | 10/1991 | Shaw |
| 5,062,164 A | 11/1991 | Lee et al. |
| 5,063,622 A | 11/1991 | Tsutsui et al. |
| 5,063,955 A | 11/1991 | Sakakibara |
| 5,072,618 A | 12/1991 | Taylor et al. |
| 5,074,322 A | 12/1991 | Jaw |
| 5,074,520 A | 12/1991 | Lee et al. |
| 5,076,424 A | 12/1991 | Nakamura |
| 5,080,324 A | 1/1992 | Chi |
| RE33,810 E | 2/1992 | Strieter |
| 5,084,984 A | 2/1992 | Duchoud et al. |
| 5,086,526 A | 2/1992 | Van Marcke |
| 5,092,560 A | 3/1992 | Chen |
| 5,095,941 A | 3/1992 | Betz |
| 5,099,587 A | 3/1992 | Jarosch |
| 5,111,594 A | 5/1992 | Allen |
| D326,711 S | 6/1992 | Lotito et al. |
| 5,117,693 A | 6/1992 | Duksa |
| 5,133,095 A | 7/1992 | Shiba et al. |
| 5,144,757 A | 9/1992 | Sasso |
| 5,146,695 A | 9/1992 | Yang |
| 5,158,114 A | 10/1992 | Botsolas |
| 5,163,234 A | 11/1992 | Tsukamoto et al. |
| 5,169,118 A | 12/1992 | Whiteside |
| 5,170,944 A | 12/1992 | Shirai |
| D332,194 S | 1/1993 | Hines |
| D332,195 S | 1/1993 | Hines |
| D332,196 S | 1/1993 | Hines |
| D332,365 S | 1/1993 | Hines |
| D332,366 S | 1/1993 | Hines |
| D332,369 S | 1/1993 | Hanna et al. |
| D332,370 S | 1/1993 | Hanna et al. |
| D332,542 S | 1/1993 | Hines |
| D332,679 S | 1/1993 | Hines |
| D332,849 S | 1/1993 | Hines |
| 5,175,892 A | 1/1993 | Shaw |
| 5,177,879 A | 1/1993 | Muta |
| 5,181,328 A | 1/1993 | Bouverie |
| D332,889 S | 2/1993 | Hines |
| 5,184,642 A | 2/1993 | Powell |
| 5,186,360 A | 2/1993 | Mease et al. |
| D334,266 S | 3/1993 | Hines |
| 5,193,563 A | 3/1993 | Melech |
| 5,199,116 A | 4/1993 | Fischer |
| 5,199,118 A | 4/1993 | Cole et al. |
| 5,199,188 A | 4/1993 | Franz |
| 5,202,666 A | 4/1993 | Knippscheer |
| D336,572 S | 6/1993 | Gunderson et al. |
| 5,216,251 A | 6/1993 | Matschke |
| 5,217,035 A | 6/1993 | Van Marcke |
| 5,224,685 A | 7/1993 | Chiang et al. |
| 5,226,629 A | 7/1993 | Millman et al. |
| 5,230,109 A | 7/1993 | Zaccai et al. |
| D338,361 S | 8/1993 | Hines |
| 5,239,610 A | 8/1993 | Shao |
| 5,243,717 A | 9/1993 | Yasuo |
| D340,374 S | 10/1993 | Hines |
| D340,375 S | 10/1993 | Hines |
| 5,251,872 A | 10/1993 | Kodaira |
| 5,253,376 A | 10/1993 | Fait |
| 5,255,822 A | 10/1993 | Mease et al. |
| D341,724 S | 11/1993 | Hines |
| 5,257,423 A | 11/1993 | Jacobsen et al. |
| 5,259,410 A | 11/1993 | Trueb et al. |

(56) References Cited

U.S. PATENT DOCUMENTS

| | | |
|---|---|---|
| 5,265,288 A | 11/1993 | Allison |
| 5,265,628 A | 11/1993 | Sage et al. |
| D342,175 S | 12/1993 | Hines |
| D342,177 S | 12/1993 | Hanna et al. |
| 5,267,475 A | 12/1993 | Gaston |
| 5,269,071 A | 12/1993 | Hamabe et al. |
| 5,272,918 A | 12/1993 | Gaston et al. |
| D342,992 S | 1/1994 | Robertson |
| 5,280,679 A | 1/1994 | Edelman |
| D344,830 S | 3/1994 | Carter et al. |
| 5,341,839 A | 8/1994 | Kobayashi et al. |
| 5,347,864 A | 9/1994 | Senghaas et al. |
| 5,351,347 A | 10/1994 | Kunkel |
| 5,351,417 A | 10/1994 | Rubin |
| 5,362,026 A | 11/1994 | Kobayashi et al. |
| 5,363,517 A | 11/1994 | Botsolas |
| 5,367,442 A | 11/1994 | Frost et al. |
| 5,369,818 A | 12/1994 | Barnum et al. |
| 5,377,424 A | 1/1995 | Albanes |
| 5,377,427 A | 1/1995 | Mashata |
| D355,949 S | 2/1995 | Laughton |
| 5,397,099 A | 3/1995 | Pilolla |
| 5,404,419 A | 4/1995 | Artis, Jr. |
| 5,412,816 A | 5/1995 | Paterson et al. |
| 5,412,818 A | 5/1995 | Chen |
| 5,426,271 A | 6/1995 | Clark et al. |
| D361,372 S | 8/1995 | Enthoven |
| 5,438,714 A | 8/1995 | Shaw |
| 5,438,763 A | 8/1995 | Yang |
| 5,442,867 A | 8/1995 | Robinson |
| D362,901 S | 10/1995 | Dannenberg et al. |
| 5,459,944 A | 10/1995 | Tatsutani et al. |
| D364,675 S | 11/1995 | Tebbe |
| 5,477,984 A | 12/1995 | Sayama et al. |
| 5,482,250 A | 1/1996 | Kodaira |
| 5,497,135 A | 3/1996 | Wisskirchen et al. |
| 5,504,950 A | 4/1996 | Natalizia et al. |
| 5,514,346 A | 5/1996 | Fujita |
| 5,522,411 A | 6/1996 | Johnson |
| 5,548,119 A | 8/1996 | Nortier |
| 5,555,912 A | 9/1996 | Saadi et al. |
| 5,561,871 A | 10/1996 | Laughton |
| 5,566,404 A | 10/1996 | Laughton |
| 5,570,869 A | 11/1996 | Diaz et al. |
| 5,586,746 A | 12/1996 | Humpert et al. |
| 5,588,636 A | 12/1996 | Eichholz et al. |
| 5,595,216 A | 1/1997 | Pilolla |
| 5,610,591 A | 3/1997 | Gallagher |
| 5,611,093 A | 3/1997 | Barnum et al. |
| 5,611,517 A | 3/1997 | Saadi et al. |
| 5,625,908 A | 5/1997 | Shaw |
| 5,627,375 A | 5/1997 | Hsieh |
| 5,640,781 A | 6/1997 | Carson |
| 5,642,462 A | 6/1997 | Huff |
| D380,529 S | 7/1997 | Laughton |
| 5,651,189 A | 7/1997 | Coykendall et al. |
| 5,651,384 A | 7/1997 | Rudrich |
| 5,670,945 A | 9/1997 | Applonie |
| D387,144 S | 12/1997 | Flaherty |
| 5,694,653 A | 12/1997 | Harald |
| 5,699,833 A | 12/1997 | Tsataros |
| 5,701,929 A | 12/1997 | Helmsderfer |
| 5,727,579 A | 3/1998 | Chardack |
| 5,730,165 A | 3/1998 | Philipp |
| D393,700 S | 4/1998 | Trueb et al. |
| 5,743,511 A | 4/1998 | Eichholz et al. |
| D394,495 S | 5/1998 | Hauser |
| 5,758,688 A | 6/1998 | Hamanaka et al. |
| 5,765,242 A | 6/1998 | Marciano |
| 5,769,120 A | 6/1998 | Laverty, Jr. et al. |
| 5,781,942 A | 7/1998 | Allen et al. |
| 5,782,382 A | 7/1998 | Van Marcke |
| D398,969 S | 9/1998 | Hauser, II |
| 5,813,047 A | 9/1998 | Teichroeb |
| 5,819,335 A | 10/1998 | Hennessy |
| 5,819,336 A | 10/1998 | Gilliam et al. |
| 5,829,072 A | 11/1998 | Hirsch et al. |
| D402,358 S | 12/1998 | Bonnell |
| 5,855,356 A | 1/1999 | Fait |
| 5,868,311 A | 2/1999 | Cretu-Petra |
| 5,873,178 A | 2/1999 | Johnson |
| 5,873,179 A | 2/1999 | Gregory et al. |
| 5,875,562 A | 3/1999 | Fogarty |
| 5,893,387 A | 4/1999 | Paterson et al. |
| 5,915,417 A | 6/1999 | Diaz et al. |
| 5,915,851 A | 6/1999 | Wattrick et al. |
| D411,876 S | 7/1999 | Hafner et al. |
| 5,918,855 A | 7/1999 | Hamanaka et al. |
| 5,924,148 A | 7/1999 | Flowers, Sr. |
| 5,943,712 A | 8/1999 | Van Marcke |
| 5,943,713 A | 8/1999 | Paterson et al. |
| 5,945,068 A | 8/1999 | Ferone |
| 5,945,913 A | 8/1999 | Gallagher |
| 5,950,983 A | 9/1999 | Jahrling |
| 5,954,069 A | 9/1999 | Foster |
| 5,961,095 A | 10/1999 | Schrott |
| 5,966,753 A | 10/1999 | Gauthier et al. |
| 5,972,126 A | 10/1999 | Fernie |
| 5,974,685 A | 11/1999 | Hironaka |
| 5,979,500 A | 11/1999 | Jahrling et al. |
| 5,984,262 A | 11/1999 | Parsons et al. |
| 5,988,588 A | 11/1999 | Allen et al. |
| 5,992,430 A | 11/1999 | Chardack et al. |
| 6,000,429 A | 12/1999 | Van Marcke |
| 6,003,170 A | 12/1999 | Humpert et al. |
| 6,006,388 A | 12/1999 | Young |
| 6,006,784 A | 12/1999 | Tsutsui et al. |
| D420,727 S | 2/2000 | Hundley |
| 6,018,885 A | 2/2000 | Hill |
| 6,029,292 A | 2/2000 | Leiferman et al. |
| 6,029,293 A | 2/2000 | Paterson et al. |
| 6,038,786 A | 3/2000 | Aisenberg et al. |
| D422,346 S | 4/2000 | Svendsen |
| 6,056,261 A | 5/2000 | Aparicio et al. |
| 6,059,192 A | 5/2000 | Zosimadis |
| 6,067,673 A | 5/2000 | Paese et al. |
| D428,477 S | 7/2000 | O'Connell et al. |
| 6,082,407 A | 7/2000 | Paterson et al. |
| 6,089,086 A | 7/2000 | Swindler et al. |
| 6,110,292 A | 8/2000 | Jewett et al. |
| D431,288 S | 9/2000 | Helmsderfer |
| 6,119,285 A | 9/2000 | Kim |
| D433,109 S | 10/2000 | Wilke et al. |
| 6,125,482 A | 10/2000 | Foster |
| 6,127,671 A | 10/2000 | Parsons et al. |
| 6,128,826 A | 10/2000 | Robinson |
| 6,131,587 A | 10/2000 | Chardack et al. |
| 6,142,342 A | 11/2000 | Lewis |
| 6,161,227 A | 12/2000 | Bargenquast |
| 6,161,814 A | 12/2000 | Jahrling |
| D435,893 S | 1/2001 | Helmsderfer |
| 6,178,572 B1 | 1/2001 | Van Marcke |
| 6,185,838 B1 | 2/2001 | Moore |
| 6,189,163 B1 | 2/2001 | Van Marcke |
| 6,189,230 B1 | 2/2001 | Huen |
| 6,192,530 B1 | 2/2001 | Dai |
| 6,199,428 B1 | 3/2001 | Estevez-Garcia et al. |
| 6,202,980 B1 | 3/2001 | Vincent et al. |
| 6,206,340 B1 | 3/2001 | Paese et al. |
| 6,209,392 B1 | 4/2001 | Rapala |
| 6,212,707 B1 | 4/2001 | Thompson et al. |
| 6,216,534 B1 | 4/2001 | Ross, Jr. et al. |
| 6,219,857 B1 | 4/2001 | Wu |
| 6,219,859 B1 | 4/2001 | Derakhshan |
| 6,236,317 B1 | 5/2001 | Cohen et al. |
| 6,250,601 B1 | 6/2001 | Kolar et al. |
| 6,253,609 B1 | 7/2001 | Ross, Jr. et al. |
| 6,253,611 B1 | 7/2001 | Varga et al. |
| 6,257,264 B1 | 7/2001 | Sturman et al. |
| 6,267,007 B1 | 7/2001 | Gunther |
| D446,664 S | 8/2001 | Petri |
| D447,224 S | 8/2001 | Hauster, II |
| 6,269,695 B1 | 8/2001 | Cesternino et al. |
| 6,273,394 B1 | 8/2001 | Vincent et al. |

(56) References Cited

U.S. PATENT DOCUMENTS

| | | |
|---|---|---|
| 6,279,179 B1 | 8/2001 | Register |
| 6,279,587 B1 | 8/2001 | Yamamoto |
| 6,282,812 B1 | 9/2001 | Wee et al. |
| 6,286,153 B1 | 9/2001 | Keller |
| 6,289,728 B1 | 9/2001 | Wilkins |
| 6,294,786 B1 | 9/2001 | Marcichow et al. |
| 6,295,410 B1 | 9/2001 | Helms et al. |
| D448,585 S | 10/2001 | Petri |
| 6,298,502 B1 | 10/2001 | Brown |
| 6,317,717 B1 | 11/2001 | Lindsey et al. |
| 6,321,785 B1 | 11/2001 | Bergmann |
| 6,322,005 B1 | 11/2001 | Kern et al. |
| 6,340,032 B1 | 1/2002 | Zosimadis |
| 6,341,389 B2 | 1/2002 | Philipps-Liebich et al. |
| D453,882 S | 2/2002 | Petri |
| 6,349,484 B1 | 2/2002 | Cohen |
| 6,351,866 B1 | 3/2002 | Bragulla |
| 6,363,549 B2 | 4/2002 | Humpert et al. |
| 6,370,951 B1 | 4/2002 | Kerchaert et al. |
| 6,386,390 B1 | 5/2002 | Tinker |
| 6,390,125 B2 | 5/2002 | Pawelzik et al. |
| 6,393,634 B1 | 5/2002 | Kodaira et al. |
| 6,401,274 B1 | 6/2002 | Brown |
| 6,408,881 B2 | 6/2002 | Lorenzelli et al. |
| 6,418,788 B2 | 7/2002 | Articolo |
| 6,426,701 B1 | 7/2002 | Levy et al. |
| 6,431,189 B1 | 8/2002 | Deibert |
| D462,195 S | 9/2002 | Wang |
| RE37,888 E | 10/2002 | Cretu-Petra |
| 6,467,514 B1 | 10/2002 | Korst et al. |
| 6,467,651 B1 | 10/2002 | Muderlak et al. |
| 6,481,040 B1 | 11/2002 | McIntyre |
| 6,481,634 B1 | 11/2002 | Zosimadis |
| 6,484,965 B1 | 11/2002 | Reaves |
| 6,508,121 B2 | 1/2003 | Eck |
| 6,523,193 B2 | 2/2003 | Saraya |
| 6,523,404 B1 | 2/2003 | Murphy et al. |
| 6,568,655 B2 | 5/2003 | Paese et al. |
| 6,572,207 B2 | 6/2003 | Hase et al. |
| D477,060 S | 7/2003 | Loberger et al. |
| 6,598,245 B2 | 7/2003 | Nishioka |
| 6,619,320 B2 | 9/2003 | Parsons |
| 6,624,606 B2 | 9/2003 | Kushida et al. |
| 6,639,209 B1 | 10/2003 | Patterson et al. |
| D481,826 S | 11/2003 | Martinuzzo et al. |
| 6,641,002 B2 | 11/2003 | Gerenraich et al. |
| 6,643,865 B2 | 11/2003 | Bork et al. |
| 6,651,851 B2 | 11/2003 | Muderlak et al. |
| D483,152 S | 12/2003 | Martinuzzo et al. |
| 6,658,934 B1 | 12/2003 | Housey et al. |
| D484,958 S | 1/2004 | Loberger et al. |
| 6,671,890 B2 | 1/2004 | Nishioka |
| 6,671,898 B1 | 1/2004 | Eggenberger et al. |
| 6,679,285 B2 | 1/2004 | Pablo |
| 6,691,340 B2 | 2/2004 | Honda et al. |
| 6,691,724 B2 | 2/2004 | Ford |
| 6,711,949 B1 | 3/2004 | Sorenson |
| 6,711,950 B1 | 3/2004 | Yamaura et al. |
| 6,715,730 B2 | 4/2004 | Ehr |
| 6,766,589 B1 | 7/2004 | Bory et al. |
| 6,769,197 B1 | 8/2004 | Tai |
| 6,769,443 B2 | 8/2004 | Bush |
| 6,770,869 B2 | 8/2004 | Patterson et al. |
| D496,450 S | 9/2004 | Loberger et al. |
| 6,789,197 B1 | 9/2004 | Saito |
| 6,812,657 B2 | 11/2004 | Raimondi |
| 6,827,294 B1 | 12/2004 | Fan et al. |
| 6,843,079 B2 | 1/2005 | Hird |
| 6,857,314 B2 | 2/2005 | Ohhashi et al. |
| 6,871,541 B2 | 3/2005 | Weisse |
| 6,882,278 B2 | 4/2005 | Winings et al. |
| 6,883,563 B2 | 4/2005 | Smith |
| D507,634 S | 7/2005 | Loberger et al. |
| 6,912,864 B2 | 7/2005 | Roche et al. |
| 6,915,690 B2 | 7/2005 | Okada et al. |
| 6,922,144 B2 | 7/2005 | Bulin et al. |
| D508,117 S | 8/2005 | Loberger et al. |
| 6,922,912 B2 | 8/2005 | Phillips |
| 6,928,235 B2 | 8/2005 | Pollack |
| 6,929,150 B2 | 8/2005 | Muderlak et al. |
| D509,577 S | 9/2005 | Loberger et al. |
| 6,950,606 B2 | 9/2005 | Logan et al. |
| D511,205 S | 11/2005 | Loberger et al. |
| D511,821 S | 11/2005 | Loberger et al. |
| 6,962,005 B1 | 11/2005 | Khosropour et al. |
| 6,962,168 B2 | 11/2005 | McDaniel et al. |
| 6,964,405 B2 | 11/2005 | Marcichow et al. |
| 6,966,334 B2 | 11/2005 | Bolster |
| 6,968,860 B1 | 11/2005 | Haenlein et al. |
| D512,648 S | 12/2005 | Smith et al. |
| 6,980,126 B2 | 12/2005 | Fournier |
| 6,986,171 B1 | 1/2006 | Perrin |
| 6,993,968 B2 | 2/2006 | Kogure |
| 6,996,863 B2 | 2/2006 | Kaneko |
| 7,007,318 B2 | 3/2006 | Bork et al. |
| 7,014,166 B1 | 3/2006 | Wang |
| 7,018,473 B2 | 3/2006 | Shadrach, III |
| 7,025,227 B2 | 4/2006 | Oliver et al. |
| 7,039,301 B1 | 5/2006 | Aisenberg et al. |
| 7,039,963 B2 | 5/2006 | Loberger et al. |
| 7,079,037 B2 | 7/2006 | Ross, Jr. et al. |
| D526,394 S | 8/2006 | Loberger et al. |
| D527,085 S | 8/2006 | Loberger et al. |
| 7,082,828 B1 | 8/2006 | Wilkins |
| 7,093,485 B2 | 8/2006 | Newman et al. |
| D527,809 S | 9/2006 | Loberger et al. |
| 7,104,519 B2 | 9/2006 | O'Maley et al. |
| 7,107,631 B2 | 9/2006 | Lang et al. |
| 7,114,510 B2 | 10/2006 | Peters et al. |
| 7,150,293 B2 | 12/2006 | Jonte |
| 7,165,450 B2 | 1/2007 | Jamnia et al. |
| 7,174,577 B2 | 2/2007 | Jost et al. |
| D537,927 S | 3/2007 | Loberger et al. |
| D538,898 S | 3/2007 | Trepanier |
| D539,400 S | 3/2007 | Loberger et al. |
| 7,191,484 B2 | 3/2007 | Dawe |
| 7,191,920 B2 | 3/2007 | Boil et al. |
| 7,198,175 B2 | 4/2007 | Ophardt |
| 7,201,052 B2 | 4/2007 | Lee |
| D542,474 S | 5/2007 | Churchill et al. |
| 7,219,686 B2 | 5/2007 | Schmitz et al. |
| 7,228,874 B2 | 6/2007 | Bolderheij et al. |
| 7,228,984 B2 | 6/2007 | Tack et al. |
| 7,232,111 B2 | 6/2007 | McDaniel et al. |
| 7,242,307 B1 | 7/2007 | LeBlond et al. |
| 7,271,728 B2 | 9/2007 | Taylor et al. |
| 7,278,624 B2 | 10/2007 | Iott et al. |
| 7,296,765 B2 | 11/2007 | Rodrian |
| 7,305,722 B2 | 12/2007 | Sha et al. |
| 7,315,165 B2 | 1/2008 | Kleinen et al. |
| 7,318,949 B2 | 1/2008 | Shadrach, III |
| 7,320,146 B2 | 1/2008 | Nortier et al. |
| D561,315 S | 2/2008 | Loberger et al. |
| 7,343,799 B2 | 3/2008 | Nagakura et al. |
| 7,350,245 B2 | 4/2008 | Giagni |
| 7,364,053 B2 | 4/2008 | Ophardt |
| 7,377,163 B2 | 5/2008 | Miyagawa |
| 7,396,000 B2 | 7/2008 | Parsons et al. |
| 7,406,722 B2 | 8/2008 | Fukuizumi et al. |
| 7,409,860 B2 | 8/2008 | Ferreira et al. |
| 7,437,833 B2 | 10/2008 | Sato et al. |
| 7,443,305 B2 | 10/2008 | Verdiramo |
| 7,451,894 B2 | 11/2008 | Ophardt |
| 7,455,197 B2 | 11/2008 | Ophardt |
| 7,458,261 B2 | 12/2008 | Miyagawa |
| 7,464,418 B2 | 12/2008 | Seggio et al. |
| 7,467,550 B2 | 12/2008 | Betz, II et al. |
| 7,471,883 B2 | 12/2008 | Seutter et al. |
| 7,472,433 B2 | 1/2009 | Rodenbeck et al. |
| 7,477,148 B2 | 1/2009 | Lynn et al. |
| 7,484,409 B2 | 2/2009 | Dykstra et al. |
| D588,676 S | 3/2009 | Loberger et al. |
| 7,516,939 B2 | 4/2009 | Bailey |
| D591,839 S | 5/2009 | Loberger et al. |

(56) References Cited

U.S. PATENT DOCUMENTS

| | | | |
|---|---|---|---|
| 7,527,174 B2 | 5/2009 | Meehan et al. |
| 7,530,269 B2 | 5/2009 | Newman et al. |
| 7,533,787 B2 | 5/2009 | Muderlak et al. |
| 7,537,195 B2 | 5/2009 | McDaniel et al. |
| 7,555,209 B2 | 6/2009 | Pradas Diez et al. |
| D599,059 S | 8/2009 | Clerch |
| 7,588,168 B2 | 9/2009 | Bagwell et al. |
| 7,596,883 B2 | 10/2009 | Kameishi |
| 7,597,122 B1 | 10/2009 | Smith |
| 7,607,442 B2 | 10/2009 | Barnhill et al. |
| 7,607,443 B2 | 10/2009 | Barnhill et al. |
| 7,614,096 B2 | 11/2009 | Vincent |
| 7,614,160 B2 | 11/2009 | Kameishi et al. |
| 7,617,830 B2 | 11/2009 | Barnhill et al. |
| 7,627,909 B2 | 12/2009 | Esche |
| 7,631,372 B2 | 12/2009 | Marty et al. |
| 7,641,173 B2 | 1/2010 | Goodman |
| 7,641,740 B2 | 1/2010 | Barnhill et al. |
| 7,650,653 B2 | 1/2010 | Johnson et al. |
| 7,651,068 B2 | 1/2010 | Bailey |
| D610,242 S | 2/2010 | Loberger et al. |
| 7,657,162 B2 | 2/2010 | Itoigawa et al. |
| 7,659,824 B2 | 2/2010 | Prodanovich et al. |
| 7,681,447 B2 | 3/2010 | Nagakura et al. |
| 7,682,464 B2 | 3/2010 | Glenn et al. |
| D614,273 S | 4/2010 | Loberger et al. |
| 7,690,395 B2 | 4/2010 | Jonte et al. |
| 7,690,623 B2 | 4/2010 | Parsons et al. |
| 7,698,770 B2 | 4/2010 | Barnhill et al. |
| 7,701,164 B2 | 4/2010 | Clothier et al. |
| 7,721,602 B2 | 5/2010 | Benner et al. |
| 7,726,334 B2 | 6/2010 | Ross, Jr. et al. |
| 7,731,154 B2 | 6/2010 | Parsons et al. |
| 7,743,438 B2 | 6/2010 | Chen |
| 7,743,782 B2 | 6/2010 | Jost |
| 7,750,594 B2 | 7/2010 | Clothier et al. |
| 7,754,021 B2 | 7/2010 | Barnhill et al. |
| 7,754,022 B2 | 7/2010 | Barnhill et al. |
| 7,757,700 B2 | 7/2010 | Barnhill et al. |
| 7,758,701 B2 | 7/2010 | Barnhill et al. |
| 7,766,026 B2 | 8/2010 | Boey |
| 7,766,194 B2 | 8/2010 | Boll et al. |
| 7,774,953 B1 | 8/2010 | Duran |
| 7,784,481 B2 | 8/2010 | Kunkel |
| 7,786,628 B2 | 8/2010 | Childe et al. |
| 7,789,095 B2 | 9/2010 | Barnhill et al. |
| 7,797,769 B2 | 9/2010 | Ozenick |
| 7,804,409 B2 | 9/2010 | Munro et al. |
| D625,792 S | 10/2010 | Rundberg et al. |
| 7,812,598 B2 | 10/2010 | Yasuda et al. |
| 7,814,582 B2 | 10/2010 | Reddy et al. |
| 7,815,134 B2 | 10/2010 | Hohl |
| 7,818,083 B2 | 10/2010 | Glenn et al. |
| 7,819,136 B1 | 10/2010 | Eddy |
| D628,280 S | 11/2010 | Loberger et al. |
| 7,825,564 B2 | 11/2010 | Croft et al. |
| RE42,005 E | 12/2010 | Jost et al. |
| D629,877 S | 12/2010 | Rundberg |
| 7,856,736 B2 | 12/2010 | Churchill et al. |
| 7,860,671 B1 | 12/2010 | LaCaze |
| D633,992 S | 3/2011 | Rundberg et al. |
| D637,350 S | 5/2011 | Kato et al. |
| 7,944,116 B2 | 5/2011 | Causier |
| 7,946,055 B2 | 5/2011 | Churchill et al. |
| 7,971,368 B2 | 7/2011 | Fukaya et al. |
| 8,037,619 B2 | 10/2011 | Liu |
| 8,043,714 B2 | 10/2011 | Hashimoto |
| 8,064,756 B2 | 11/2011 | Liu |
| 8,128,465 B2 | 3/2012 | Collins |
| D661,023 S | 5/2012 | Liu et al. |
| 8,561,626 B2 | 10/2013 | Sawaski et al. |
| 8,944,105 B2 | 2/2015 | Rodenbeck et al. |
| 8,997,271 B2 | 4/2015 | Bayley et al. |
| 2001/0011389 A1 | 8/2001 | Philipps-Liebich et al. |
| 2001/0011390 A1 | 8/2001 | Humpert et al. |
| 2001/0020619 A1 | 9/2001 | Pfeifer et al. |
| 2002/0006275 A1 | 1/2002 | Pollack |
| 2002/0019709 A1 | 2/2002 | Segal |
| 2002/0104159 A1 | 8/2002 | Nishioka |
| 2002/0157176 A1 | 10/2002 | Wawrla et al. |
| 2002/0171056 A1 | 11/2002 | Paese et al. |
| 2003/0037612 A1 | 2/2003 | Nagakura et al. |
| 2003/0172547 A1 | 9/2003 | Shephard |
| 2003/0188380 A1 | 10/2003 | Loberger et al. |
| 2003/0210140 A1 | 11/2003 | Menard et al. |
| 2003/0213062 A1 | 11/2003 | Honda et al. |
| 2004/0016296 A1 | 1/2004 | Weisse |
| 2004/0025248 A1 | 2/2004 | Lang et al. |
| 2004/0083547 A1 | 5/2004 | Mercier |
| 2004/0128755 A1 | 7/2004 | Loberger et al. |
| 2004/0129075 A1 | 7/2004 | Sorenson |
| 2004/0143898 A1 | 7/2004 | Jost et al. |
| 2004/0149779 A1 | 8/2004 | Boll et al. |
| 2004/0182151 A1 | 9/2004 | Meure |
| 2004/0221645 A1 | 11/2004 | Brzozowski et al. |
| 2004/0221646 A1 | 11/2004 | Ohhashi et al. |
| 2004/0221647 A1 | 11/2004 | Sabatino |
| 2004/0238660 A1 | 12/2004 | Fan et al. |
| 2005/0000015 A1 | 1/2005 | Kaneko |
| 2005/0087557 A1 | 4/2005 | Oliver et al. |
| 2005/0098968 A1 | 5/2005 | Dyson et al. |
| 2005/0199843 A1 | 9/2005 | Jost et al. |
| 2005/0205818 A1 | 9/2005 | Bayley et al. |
| 2006/0098961 A1 | 5/2006 | Seutter et al. |
| 2006/0101575 A1 | 5/2006 | Louis |
| 2006/0102642 A1 | 5/2006 | Muntzing et al. |
| 2006/0145111 A1 | 7/2006 | Lang et al. |
| 2006/0150316 A1 | 7/2006 | Fukuizumi et al. |
| 2006/0151513 A1 | 7/2006 | Shadrach, III |
| 2006/0185074 A1 | 8/2006 | Loberger et al. |
| 2006/0200903 A1 | 9/2006 | Rodenbeck et al. |
| 2006/0207019 A1 | 9/2006 | Vincent |
| 2006/0225200 A1 | 10/2006 | Wierenga |
| 2006/0272170 A1 | 12/2006 | Holmes |
| 2007/0023565 A1 | 2/2007 | Babikian |
| 2007/0079524 A1 | 4/2007 | Sato et al. |
| 2007/0094787 A1 | 5/2007 | Hwang |
| 2007/0144034 A1* | 6/2007 | Kameishi ............... A47K 10/48 34/523 |
| 2007/0151338 A1 | 7/2007 | Benner et al. |
| 2007/0152082 A1 | 7/2007 | Hyslop |
| 2007/0194637 A1 | 8/2007 | Childe et al. |
| 2007/0230839 A1 | 10/2007 | Childe et al. |
| 2007/0252551 A1 | 11/2007 | Clothier et al. |
| 2007/0261162 A1 | 11/2007 | Atkinson |
| 2007/0263994 A1* | 11/2007 | Diez .................. A47K 10/48 392/380 |
| 2007/0278983 A1 | 12/2007 | Clothier et al. |
| 2008/0005833 A1 | 1/2008 | Bayley et al. |
| 2008/0018995 A1 | 1/2008 | Baun |
| 2008/0052952 A1 | 3/2008 | Nelson |
| 2008/0072668 A1 | 3/2008 | Miyagawa |
| 2008/0078019 A1 | 4/2008 | Allen, Jr. et al. |
| 2008/0083786 A1 | 4/2008 | Marin |
| 2008/0098950 A1 | 5/2008 | Gudjohnsen et al. |
| 2008/0099088 A1 | 5/2008 | Boey |
| 2008/0109956 A1 | 5/2008 | Bayley et al. |
| 2008/0127410 A1 | 6/2008 | Schmitt et al. |
| 2008/0185396 A1 | 8/2008 | Yang et al. |
| 2008/0185398 A1 | 8/2008 | Yang et al. |
| 2008/0185399 A1 | 8/2008 | Yang et al. |
| 2008/0189850 A1 | 8/2008 | Seggio et al. |
| 2008/0193111 A1 | 8/2008 | Seutter et al. |
| 2008/0209760 A1 | 9/2008 | French et al. |
| 2008/0213644 A1 | 9/2008 | Shindoh et al. |
| 2008/0216343 A1 | 9/2008 | Churchill et al. |
| 2008/0216344 A1 | 9/2008 | Churchill et al. |
| 2008/0222910 A1 | 9/2008 | Churchill et al. |
| 2008/0253754 A1 | 10/2008 | Rubin |
| 2008/0256825 A1 | 10/2008 | Hsu |
| 2008/0271527 A1 | 11/2008 | Hewitt |
| 2008/0285134 A1 | 11/2008 | Closset et al. |
| 2008/0289098 A1 | 11/2008 | Kunkel |
| 2008/0301970 A1 | 12/2008 | Hackwell et al. |

(56) References Cited

U.S. PATENT DOCUMENTS

| | | |
|---|---|---|
| 2008/0313918 A1 | 12/2008 | Dyson et al. |
| 2008/0313919 A1 | 12/2008 | Churchill et al. |
| 2008/0317448 A1 | 12/2008 | Brown et al. |
| 2009/0000023 A1 | 1/2009 | Wegelin et al. |
| 2009/0000024 A1 | 1/2009 | Louis et al. |
| 2009/0000142 A1 | 1/2009 | Churchill et al. |
| 2009/0000147 A1 | 1/2009 | Collins |
| 2009/0031493 A1 | 2/2009 | Tsujita et al. |
| 2009/0034946 A1 | 2/2009 | Simmonds |
| 2009/0049599 A1 | 2/2009 | Parsons et al. |
| 2009/0056011 A1 | 3/2009 | Wolf et al. |
| 2009/0058666 A1 | 3/2009 | Clabaugh |
| 2009/0069870 A1 | 3/2009 | Haase et al. |
| 2009/0077736 A1* | 3/2009 | Loberger ............ E03C 1/057 4/623 |
| 2009/0094740 A1 | 4/2009 | Ji |
| 2009/0100593 A1 | 4/2009 | Lincoln et al. |
| 2009/0113746 A1 | 5/2009 | Churchill et al. |
| 2009/0113748 A1 | 5/2009 | Dyson et al. |
| 2009/0119832 A1 | 5/2009 | Conroy |
| 2009/0119942 A1 | 5/2009 | Aisenberg et al. |
| 2009/0126103 A1 | 5/2009 | Dietrich et al. |
| 2009/0159612 A1 | 6/2009 | Beavis et al. |
| 2009/0183383 A1* | 7/2009 | Kroll ............ A45D 20/22 34/99 |
| 2009/0236358 A1 | 9/2009 | Rippl et al. |
| 2009/0243243 A1 | 10/2009 | Watson |
| 2009/0266157 A1 | 10/2009 | Maruo et al. |
| 2009/0272445 A1 | 11/2009 | Shimizu et al. |
| 2009/0293190 A1 | 12/2009 | Ringelstetter et al. |
| 2009/0293192 A1 | 12/2009 | Pons |
| 2009/0293304 A1 | 12/2009 | Yang |
| 2010/0014844 A1 | 1/2010 | Dannenberg et al. |
| 2010/0108892 A1* | 5/2010 | Zhang ............ G01S 7/491 250/353 |
| 2010/0132112 A1 | 6/2010 | Bayley et al. |
| 2010/0139394 A1 | 6/2010 | Pauer et al. |
| 2010/0154239 A1 | 6/2010 | Hutchinson |
| 2010/0168926 A1 | 7/2010 | Bayley et al. |
| 2010/0192399 A1 | 8/2010 | Sawabe et al. |
| 2010/0199759 A1 | 8/2010 | Prasad |
| 2010/0213208 A1 | 8/2010 | Ben et al. |
| 2010/0219013 A1 | 9/2010 | Liddell |
| 2010/0223993 A1 | 9/2010 | Shimizu et al. |
| 2010/0231392 A1 | 9/2010 | Sherron |
| 2010/0236092 A1 | 9/2010 | Causier |
| 2010/0252759 A1 | 10/2010 | Guler et al. |
| 2010/0269364 A1 | 10/2010 | Liu |
| 2010/0276529 A1 | 11/2010 | Nguyen |
| 2010/0296799 A1 | 11/2010 | Liu |
| 2011/0006083 A1 | 1/2011 | Walters et al. |
| 2011/0023319 A1 | 2/2011 | Fukaya et al. |
| 2011/0155934 A1 | 6/2011 | Guler et al. |
| 2011/0171083 A1 | 7/2011 | Swistak |
| 2011/0271441 A1 | 11/2011 | Bayley et al. |
| 2011/0277342 A1 | 11/2011 | Ishii et al. |
| 2012/0011739 A1 | 1/2012 | Nakamura |
| 2012/0017459 A1 | 1/2012 | Kikuchi et al. |
| 2012/0017460 A1 | 1/2012 | Kikuchi et al. |
| 2012/0042536 A1* | 2/2012 | White ............ A47K 10/48 34/486 |
| 2012/0055557 A1 | 3/2012 | Belz et al. |
| 2012/0291195 A1 | 11/2012 | Courtney et al. |
| 2012/0291303 A1 | 11/2012 | Courtney et al. |
| 2013/0025045 A1 | 1/2013 | Gagnon et al. |
| 2013/0031799 A1 | 2/2013 | Gagnon et al. |
| 2013/0042497 A1 | 2/2013 | Ryan et al. |
| 2013/0055588 A1 | 3/2013 | Nakamura et al. |
| 2013/0104413 A1 | 5/2013 | Akiyoshi et al. |
| 2013/0139400 A1 | 6/2013 | Fukano |
| 2013/0199640 A1 | 8/2013 | Williamson |
| 2014/0253336 A1* | 9/2014 | Ophardt ............ A47K 5/1202 340/573.1 |
| 2015/0000025 A1* | 1/2015 | clements ............ G06F 3/013 4/443 |

FOREIGN PATENT DOCUMENTS

| | | |
|---|---|---|
| AU | 2006274708 | 2/2007 |
| AU | 2006274715 | 2/2007 |
| BE | 347407 | 12/1927 |
| CN | 102665512 | 9/2012 |
| DE | 504089 | 7/1930 |
| DE | 2018695 | 10/1971 |
| DE | 2304815 | 8/1974 |
| DE | 2657164 | 12/1976 |
| DE | 7707416 | 7/1977 |
| DE | 3036623 | 2/1982 |
| DE | 4218658 | 12/1992 |
| DE | 9304270 | 9/1993 |
| DE | 9304160 | 7/1994 |
| DE | 19608157 | 7/1997 |
| DE | 10210474 | 9/2002 |
| DE | 69821140 | 11/2004 |
| DE | 20-2004-012352 | 12/2004 |
| DE | 20-2005-018472 | 2/2006 |
| DE | 10-2009-003070 | 11/2010 |
| EP | 0274785 | 7/1988 |
| EP | 1057942 | 12/2000 |
| EP | 1241301 | 9/2002 |
| EP | 1250378 | 10/2002 |
| EP | 1258568 | 11/2002 |
| EP | 1057441 | 9/2006 |
| EP | 1912549 | 3/2010 |
| EP | 2177142 | 4/2010 |
| EP | 2277424 | 1/2011 |
| EP | 2554085 | 2/2013 |
| GB | 549766 | 12/1942 |
| GB | 737054 | 9/1955 |
| GB | 909069 | 10/1962 |
| GB | 915674 | 1/1963 |
| GB | 2249026 | 4/1992 |
| GB | 2358350 | 7/2001 |
| GB | 2380676 | 4/2003 |
| GB | 2450563 | 12/2008 |
| JP | 49-037685 | 4/1974 |
| JP | 61-179993 | 11/1986 |
| JP | 01-071575 | 5/1989 |
| JP | 1256632 | 10/1989 |
| JP | 04-221523 | 8/1992 |
| JP | 04-136195 | 12/1992 |
| JP | 05007752 | 2/1993 |
| JP | 5163748 | 6/1993 |
| JP | 05-055988 | 7/1993 |
| JP | 06-062977 | 3/1994 |
| JP | 07-116076 | 5/1995 |
| JP | 8-140891 | 6/1996 |
| JP | 08-164088 | 6/1996 |
| JP | 08-196470 | 8/1996 |
| JP | 08-266939 | 10/1996 |
| JP | 9-056640 | 3/1997 |
| JP | 9-135788 | 5/1997 |
| JP | 09-215631 | 8/1997 |
| JP | 9242155 | 9/1997 |
| JP | 10-113304 | 5/1998 |
| JP | 10-113305 | 5/1998 |
| JP | 10-248748 | 9/1998 |
| JP | 10-257992 | 9/1998 |
| JP | 11-000283 | 1/1999 |
| JP | 11-113789 | 4/1999 |
| JP | 11-169317 | 6/1999 |
| JP | 11244190 | 9/1999 |
| JP | 2000-000178 | 1/2000 |
| JP | 2000-000180 | 1/2000 |
| JP | 2000-157448 | 6/2000 |
| JP | 2000-184987 | 7/2000 |
| JP | 2000262433 | 9/2000 |
| JP | 2000-271039 | 10/2000 |
| JP | 2000-282528 | 10/2000 |

(56) References Cited

FOREIGN PATENT DOCUMENTS

| | | |
|---|---|---|
| JP | 2000-300461 | 10/2000 |
| JP | 2001-000361 | 1/2001 |
| JP | 2001-003407 | 1/2001 |
| JP | 2001-104213 | 4/2001 |
| JP | 2001-140305 | 5/2001 |
| JP | 2001-346715 | 12/2001 |
| JP | 2002-028100 | 1/2002 |
| JP | 2002115303 | 4/2002 |
| JP | 2002-136448 | 5/2002 |
| JP | 2002-345682 | 12/2002 |
| JP | 2003-153823 | 5/2003 |
| JP | 2003275112 | 9/2003 |
| JP | 2004-215879 | 8/2004 |
| JP | 2004-261510 | 9/2004 |
| JP | 2005-168799 | 6/2005 |
| JP | 2006-081925 | 3/2006 |
| JP | 2006-101987 | 4/2006 |
| JP | 2006-192250 | 7/2006 |
| JP | 2006-204738 | 8/2006 |
| JP | 2006-304926 | 11/2006 |
| JP | 2007-054670 | 3/2007 |
| JP | 2007-082904 | 4/2007 |
| JP | 2007-098106 | 4/2007 |
| JP | 2007209459 | 8/2007 |
| JP | 2008-005883 | 1/2008 |
| JP | 2008-073152 | 3/2008 |
| JP | 2008-080100 | 4/2008 |
| JP | 2008-099797 | 5/2008 |
| JP | 2008-110240 | 5/2008 |
| JP | 2008-272086 | 11/2008 |
| JP | 2008-272251 | 11/2008 |
| JP | 2009088657 | 4/2009 |
| JP | 2010-048238 | 3/2010 |
| JP | 2010-075602 | 4/2010 |
| JP | 2010-110450 | 5/2010 |
| JP | 3160341 | 6/2010 |
| JP | 2011-055859 | 3/2011 |
| KR | 100711544 | 4/2007 |
| KR | 20120070020 | 6/2012 |
| NL | 1017777 | 10/2002 |
| TW | 567822 | 12/2003 |
| TW | 408638 | 8/2011 |
| WO | 96/26795 | 9/1995 |
| WO | 01/16436 | 3/2001 |
| WO | 2006/055681 | 5/2006 |
| WO | 2007/011747 | 1/2007 |
| WO | 2007/015036 | 2/2007 |
| WO | 2007/015039 | 2/2007 |
| WO | 2007/015046 | 2/2007 |
| WO | 2007-067924 | 6/2007 |
| WO | 2009/039290 | 3/2009 |
| WO | 2009/062546 | 5/2009 |
| WO | 2010/088975 | 8/2010 |
| WO | 2010/089927 | 8/2010 |
| WO | 2010/095250 | 8/2010 |
| WO | 2010/095251 | 8/2010 |
| WO | 2010/119536 | 10/2010 |
| WO | 2011/009156 | 1/2011 |
| WO | 2011/044247 | 4/2011 |
| WO | 2011/074018 | 6/2011 |
| WO | 2011/077625 | 6/2011 |

\* cited by examiner

BASIN AND HAND DRYING SYSTEM

CROSS-REFERENCE(S) TO RELATED APPLICATION(S)

This application claims a benefit of priority under 35 USC §119 based on International Application No. PCT/US2013/031171 filed on Mar. 14, 2013, which claims priority to U.S. Provisional Patent Application No. 61/620,541 filed Apr. 5, 2012 as well as on U.S. Provisional Patent Application No. 61/613,821 filed Mar. 21, 2012, the entire contents of both are hereby expressly incorporated by reference into the present application.

BACKGROUND OF THE INVENTION

The present invention relates generally to the field of lavatory systems and, more particularly, to an integrated wash basin and hand drying system.

An exemplary lavatory system is described in U.S. Ser. No. 13/088,793, which is assigned to Bradley Fixtures Corporation, the assignee of this application. The aforementioned application, which is incorporated herein, describes a lavatory system in which a hand washing station has a wash basin, a faucet, and an electric hand dryer. The integration of these components into a single wash station alleviates the need for a user to leave the wash station to access a hand dryer. That is, the hand dryer is adjacent the wash basin and blown into an area generally above the wash basin. Accordingly, a user can water and soap his hands in a conventional manner and then move his hands to the drying zone of the hand dryer. The user's hands do not need to leave the wash basin for the hands to be exposed to the drying air. Hence, water does not drip onto the floor as the user presents his hands to the dryer and water wicked from the hands is blown into the wash basin rather than onto the floor.

SUMMARY AND OBJECTS OF THE INVENTION

By way of summary, the present invention is directed to lavatory systems. An effect of the present invention is to allow a lavatory user to wash and dry his/her hands in a clean, convenient, and sanitary manner.

The lavatory system may include a basin including a water collecting area and a back splash. The back splash may integrate with a soap dispenser and a faucet. A hand dryer including a first plenum extending from the backsplash and a second plenum integrated with the water collecting form a drying cavity configured to receive a person's hands. A faucet extending from the back splash may supply water for hand washing. A soap dispenser extending from the back splash may dispense soap for hand washing. A drain may be included in the basin below the faucet for draining water from the faucet, soap from the soap dispenser, and water removed from the person's hands by the hand dryer. An additional drain may be included by the hand dryer that is plumbed into the faucet drain.

A lavatory system cover may be attached beneath the basin for enclosing plumbing, a blower motor, or any other mechanicals. A pair of end caps may be removably attached to a first and second side of the lavatory system. The removable end caps may conceal attachments for additional lavatory systems when attached, and removed for attaching the additional lavatory systems.

The lavatory system may be further equipped with a microcontroller in communication with proximity sensors integrated with the soap dispenser, hand dryer, and faucet configured to activate the soap dispenser, hand dryer, and faucet, respectively, when an object is sensed. A moisture sensor also in communication with the microcontroller may be included for detecting a moisture content of a person's hands in proximity to the hand dryer. The microcontroller may be configured to calculate the optimum run time for a hand dryer blower motor based on the sensed moisture content.

One primary object of the invention is to provide an apparatus with a color LED display that displays information from a system diagnostics system that may be controlled by the microcontroller. The LED display also communicates to a user or maintenance person a maintenance procedure. Another object of the invention is to provide a lavatory system with active noise cancellation features, resulting in quiet operation. Another object of the invention is to provide an apparatus that has one or more of the characteristics discussed above in various color and material combinations, thus, allowing for an aesthetically pleasing environment.

Another aspect of the invention, these objects are achieved by providing an apparatus comprising sterilization features. In one embodiment, the lavatory system may use any of the following: ultra violet lights, HEPA filtration, ionization, and antimicrobial agents.

Yet another aspect of the invention, an electric hand dryer may be incorporated into the lavatory system with various nozzle designs allowing a custom-tailored solution in directing the direction and strength of the air travel from the electric hand dryer. The electric hand dryer may also utilize a dryer drain plumbed into the lavatory's drain, preventing water from a user's hands from ending up on the floor.

In accordance with yet another aspect of the invention, the electric hand dryer may utilize a blower motor with the ability to last for one-half to 1 million cycles over its usable life. This may be accomplished through the use of a brushless motor, a motor with curvilinear brushes, or helically curved brushes. Such a motor may have the ability to provide 68,000 activations per year wherein each activation lasts 15-30 seconds. The electric hand dryer may include a configuration to reduce air pressure within the unit and thus increase overall motor life. The volume of air supplied to the hand cavity may include a measured volume of approximately 333 cu. inches, e.g., approximate dimensions of a length of 9.5 inches, depth of 10 inches, and height of 3.5 inches.

In order to prevent water from damaging the hand dryer, a flood relief portion is connected to the basin preventing water in the basin from contacting the electric blower motor. To prevent water from splashing onto a person from a person's hands when using the hand dryer, a plurality of nozzles oriented with a plurality of angles is included within the first and second plenums.

A microcontroller may also be included that is programmed to control the hand dryer, soap dispenser, and faucet with a triangulation algorithm using a plurality of inputs from a plurality of proximity sensors configured to sense a person's hands proximate to the hand dryer, soap dispenser, and faucet. An additional sensor may be included to sense a level of contamination on a user's hands, and wherein the microcontroller determines a quantity of soap to dispense from the soap dispenser as a result. Also, a moisture sensor may be in communication with the microcontroller for detecting a moisture content of a person's hands in proximity to the hand dryer. A run time determined by the microcontroller for the electric blower motor based on the moisture content may be calculated by the microcontroller. The proximity sensors may include at least one camera and the microcontroller may be programmed with image processing to determine if a person's hands are proximate to the hand dryer.

The lavatory system may include a display screen attached to the basin for displaying either active text-based information and/or active graphical information that includes advertising and time usage of the lavatory system.

An active noise cancellation system may be included that is configured to cancel an acoustic noise produced by the lavatory system.

A primary object of the invention is to provide an apparatus with a color LED display that displays information from a system diagnostics system. The LED display also communicates to a user or maintenance person a maintenance procedure. Another object of the invention is to provide a lavatory system with active noise cancellation features, resulting in quiet operation. Another object of the invention is to provide an apparatus that has one or more of the characteristics discussed above in various color and material combinations, thus, allowing for an aesthetically pleasing environment.

In accordance with one aspect of the invention, these objects are achieved by providing an apparatus comprising sterilization features. In one embodiment, the lavatory system may use any of the following: ultra violet lights, HEPA filtration, and antimicrobial agents.

In accordance with another aspect of the invention, an electric hand dryer may be incorporated into the lavatory system with various nozzle designs allowing a custom-tailored solution in directing the direction and strength of the air travel from the electric hand dryer.

These and other aspects and objects of the present invention will be better appreciated and understood when considered in conjunction with the following description and the accompanying drawings. It should be understood, however, that the following description, while indicating preferred embodiments of the present invention, is given by way of illustration and not of limitation. Many changes and modifications may be made within the scope of the present invention without departing from the spirit thereof, and the invention includes all such modifications.

Figure 1:
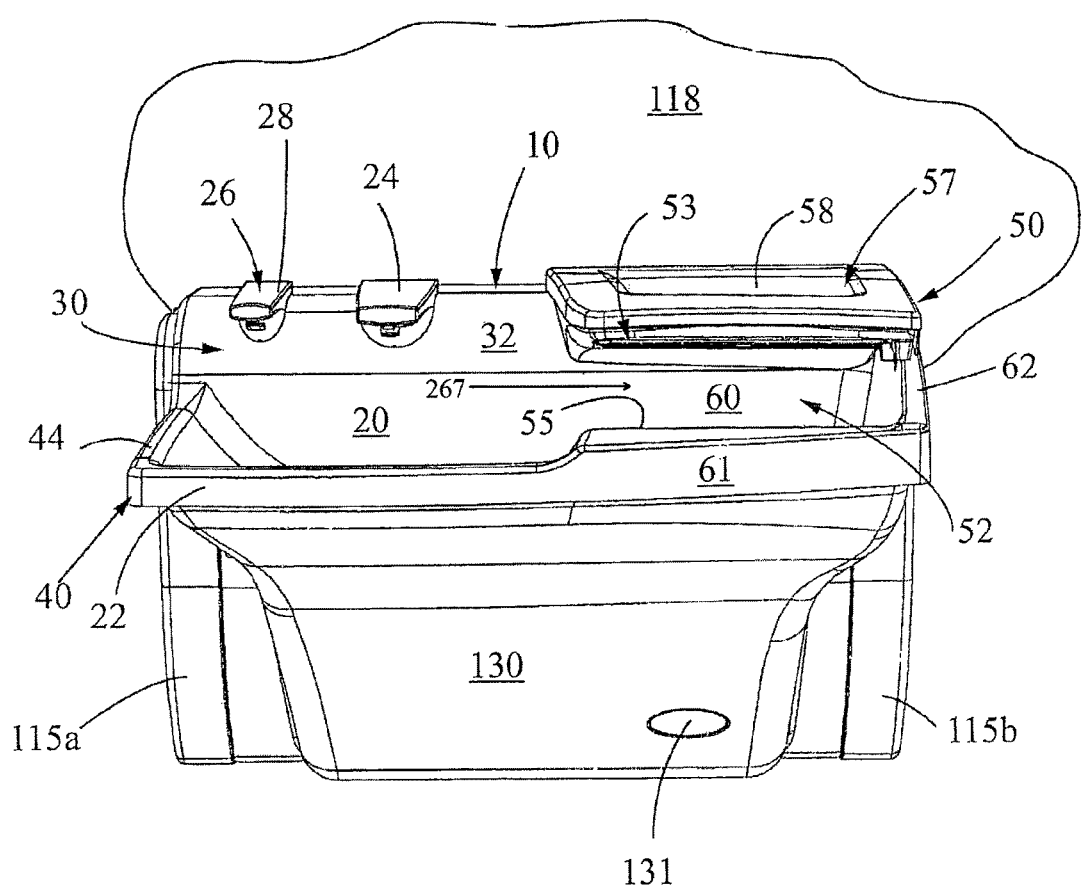
FIG. 1 illustrates a view of a lavatory system of the present invention.

In describing the preferred embodiment of the invention which is illustrated in the drawings, specific terminology will be resorted to for the sake of clarity. However, it is not intended that the invention be limited to the specific terms so selected and it is to be understood that each specific term includes all technical equivalents which operate in a similar manner to accomplish a similar purpose. For example, the words "connected", "attached", or terms similar thereto are often used. They are not limited to direct connection but include connection through other elements where such connection is recognized as being equivalent by those skilled in the art.

DETAILED DESCRIPTION OF EMBODIMENTS

The present invention will be described with respect to a hand dryer that is part of an integrated lavatory system also having a wash basin, a water faucet, and, optionally, a soap dispenser. However, it is understood that the present invention is applicable with standalone hand dryers, such as conventional wall-mounted hand dryers, and may also be desirable for other types of dryers in which it is desirable to delay commencement of a drying cycle based on the presentment of an object to be dried to a drying chamber, cavity, or zone. In one preferred embodiment, the present invention is applicable with an integrated lavatory system such as that described in U.S. Ser. No. 13/088,793; however, as noted above, the invention is not so limited.

Turning now to FIGS. 1-24, a lavatory system 10, preferably, has a wash basin 20, including a wash basin wall 22. As shown in FIGS. 1-4, faucet 24 is provided within the wash basin 20. The faucet 24 may include indicia etched thereon such as a water droplet symbol or a faucet light 23 for directing a user. Such etched indicia may be particularly helpful to a user that has poor eyesight. The faucet 24 may also include a sensor located behind a sensor window 25 which automatically engages a faucet control to provide water to the user. The faucet 24 is connected to plumbing to provide hot and/or cold water to the faucet. Preferably, the water is provided at a comfortable temperature for the user's hands by preferably controlling the blend of hot and cold water.

A soap dispensing system 26 is near the faucet 24 and in the wash basin 20. The soap dispenser 26 includes a spout 28 and a soap dispensing sensor (located behind sensor window 29) to detect an object, such as a user's hand 166 (see, e.g., FIG. 20), and provide soap thereto. Indicia, such as soap bubbles, or a light 27, may also be placed on the spout 28. As best shown in FIG. 1, a countertop 30 is preferably provided above and around the wash basin 20. The soap dispenser or system 26 includes a liquid soap container (not shown) located under the wash basin 20 and countertop 30 and that is connected to the spout 28. A backsplash 32 may also be present and integral with the countertop 30. Thus, the soap container is masked, in part, also by the backsplash 32. Further disclosure of one embodiment of the soap dispensing system 26 may be found in co-pending U.S. patent application Ser. No. 13/088,512 further incorporated herein by reference.

Figure 2:
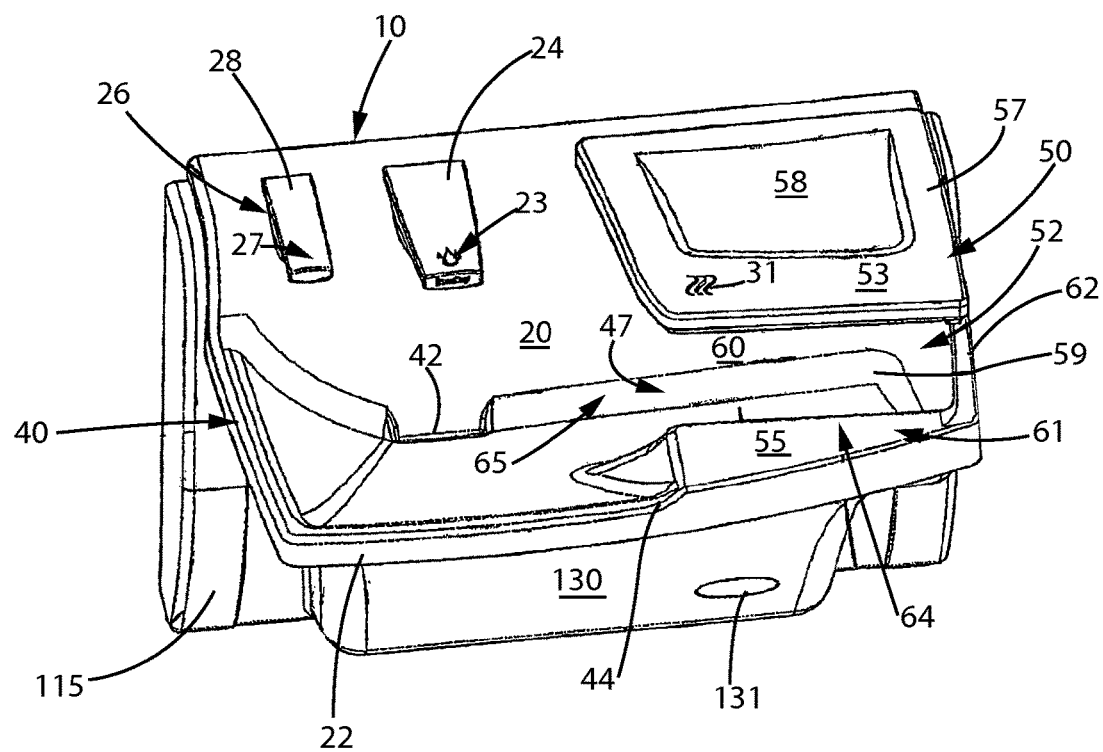
FIG. 2 is a front elevation view of a lavatory system according to the present invention.
Figure 3:
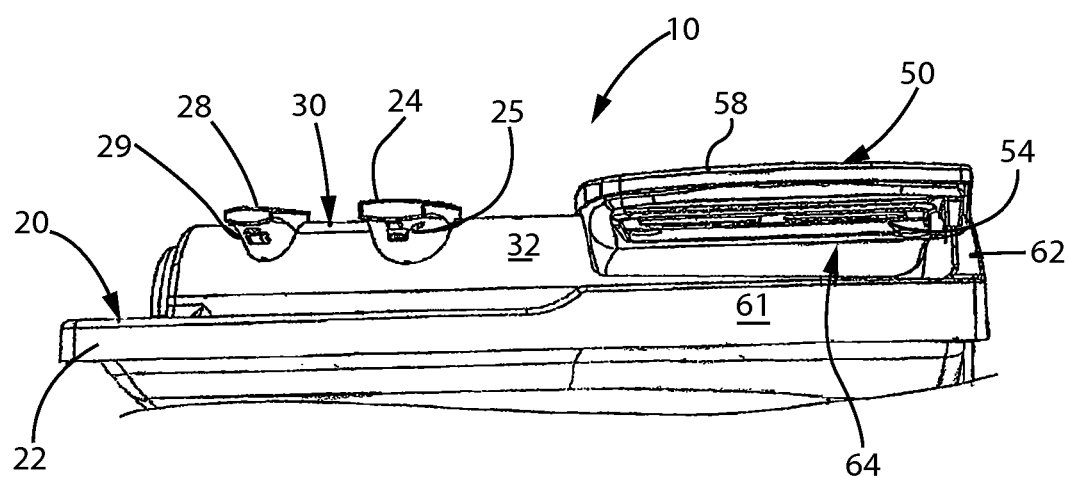
FIG. 3 is a front elevation cutaway view of a lavatory system according to the present invention showing upper portion and hand-washing features.
Figure 4:
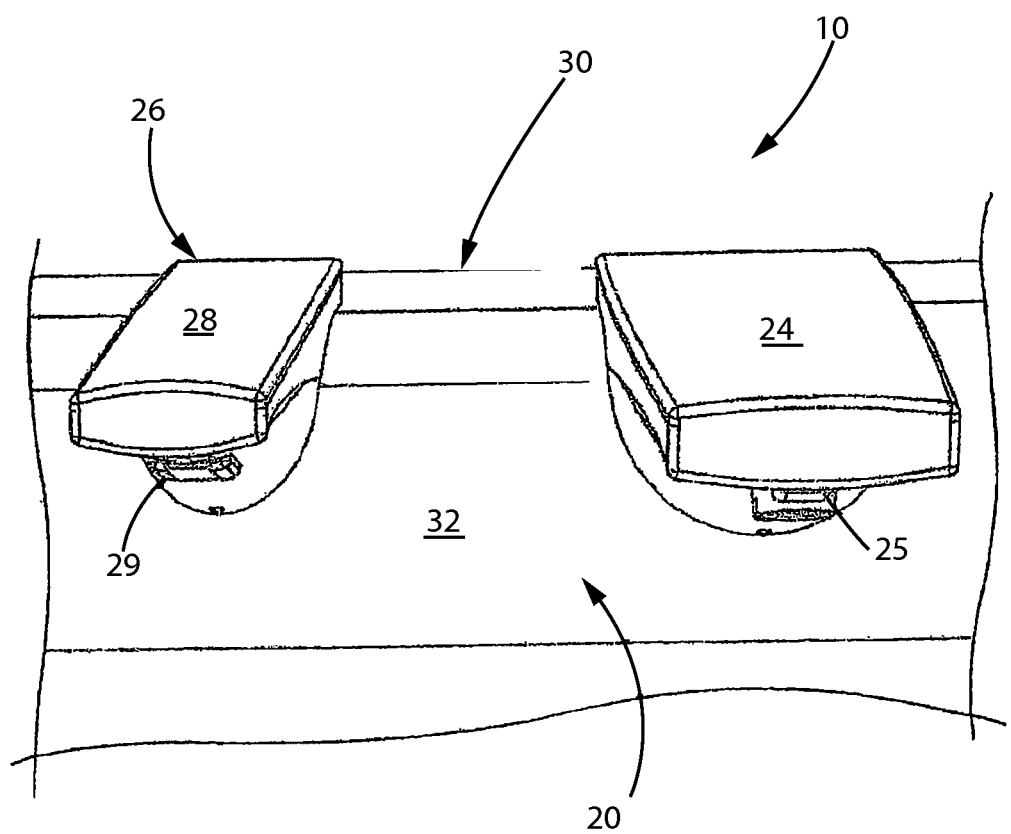
FIG. 4 is a front elevation view of a cutaway portion of the lavatory system according to the present invention showing the faucet and soap dispenser.

As best seen in FIG. 2, preferably a single drain 42, preferably with drain cap, is provided in the wash basin 20. This drain 42 takes soap and water from the wash basin 20 down to a drainpipe (not shown). The drainpipe 127 is preferably located directly under the wash basin 20 (see, e.g., FIG. 18).

As seen in FIGS. 5-9, the lavatory system 10 preferably includes an integral drying system, e.g., a hand dryer 50. The hand dryer 50 has a hand-receiving cavity 52 and a motor 74. In one preferred embodiment, a mechanism 40 for preventing flooding and damage to the motor 74 is provided. The mechanism 40 may include a flood relief rim or overflow lip 44 located on the wash basin 20, see, e.g., FIG. 6A. The flood relief rim 44 is provided below the lower portion's air outlet 56 and the nozzle tips 162b as shown. Thus, water that cannot make it down the drain 42 will flow over the flood relief rim 44 and not down the nozzle holes 162b and into the motor 74. Other motor protection and flood prevention mechanisms 40 will be described further below.

Referring now to FIG. 2, the hand dryer 50 may be provided with etched instructional indicia, a heat wave symbol, or light 31. A drain conduit 47 is preferably present to fluidly connect the hand-receiving cavity 52 and wash basin 20. The conduit 47 removes excess water from the user's hands that has been left through the hand-receiving cavity 52 down toward the single drain 42 in the wash basin 20. This water then travels down the drainpipe 127, see, e.g., FIG. 18.

Figure 5:
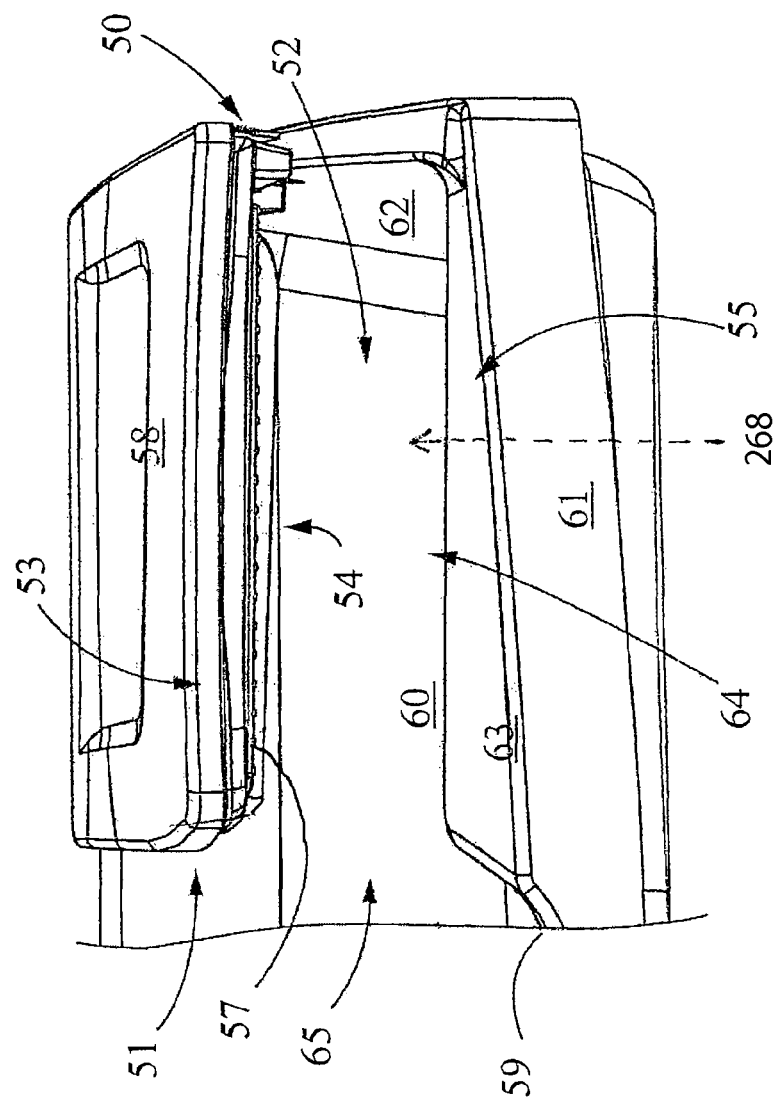
FIG. 5 is a front elevation view of a cutaway portion of the lavatory system according to the present invention showing the upper portion and upper air outlet.

As best seen in FIG. 5, the hand dryer 50 is preferably provided with a top portion 53 and a bottom portion 55. The top portion 53 may also include a hood 51 with a base which forms a top wall 57 of the cavity 52. The top portion hood 51 may also include a top portion cover which may form a shelf 58. An upper air outlet 54 is also provided in the upper portion 53.

Figure 6A:
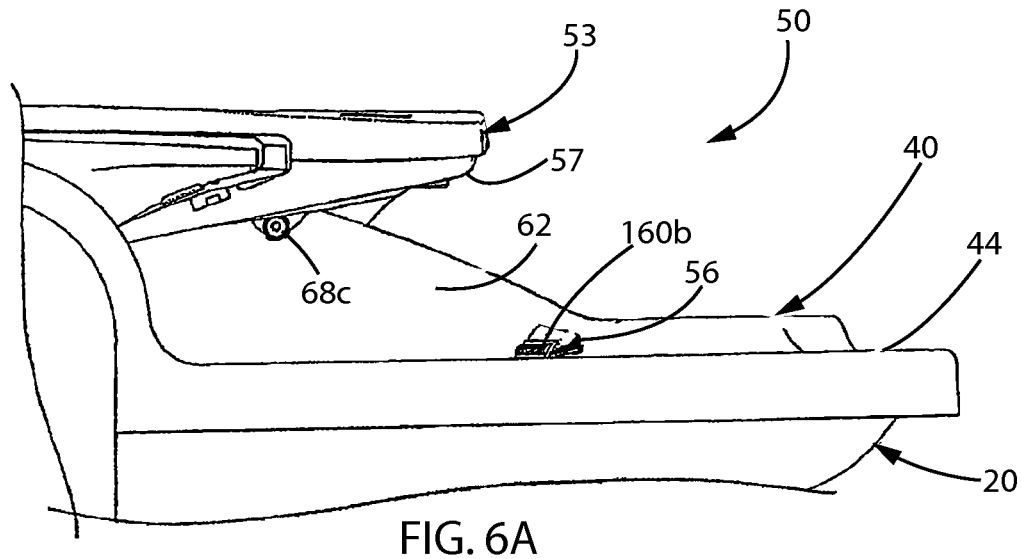
FIG. 6A is a side view of a cutaway portion of the lavatory system according to the present invention showing the upper portion, lower nozzles, and basin.
Figure 6B:
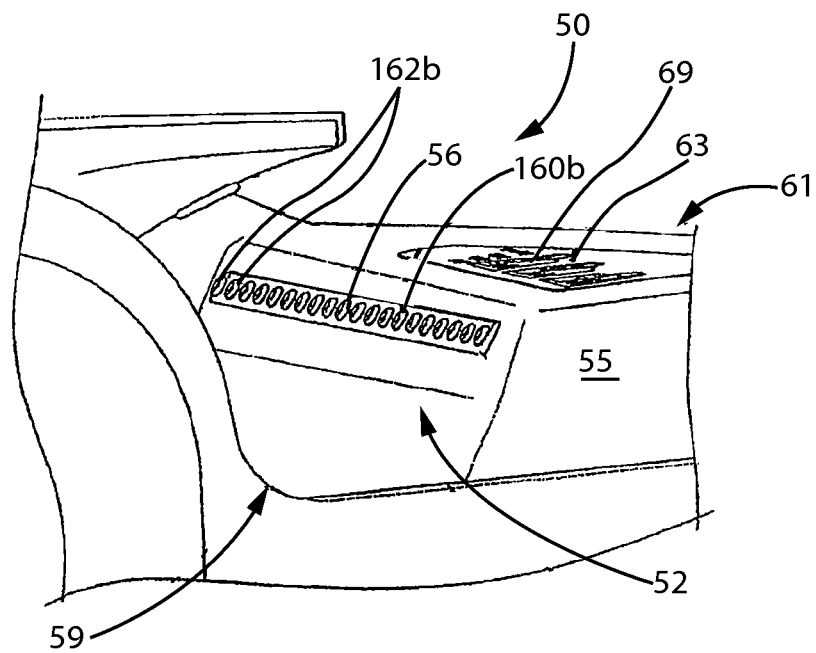
FIG. 6B is a side view of a cutaway portion of the lavatory system according to the present invention illustrating the hand dryer and lower nozzle tips.

As best shown in FIGS. 5, 6A, and 6B, a bottom portion 55 includes a lower air outlet 56. The bottom portion 55 is formed, in part, by bottom wall 59. The bottom portion 55 of the hand-receiving cavity 52 preferably also includes a back wall 60, front wall 61, and single side wall 62 (see, e.g., FIG. 5). A front ledge 63 is preferably integral with the front wall 61. The hand-receiving cavity 52, therefore, is preferably configured to have a front opening 64 and a single side opening 65 (herein the left side) and allows users to enter their hands at a generally oblique angle. Further, instructions 69 for using the hand dryer may be provided on the front ledge 63 as shown in FIG. 6B.

Figure 7:
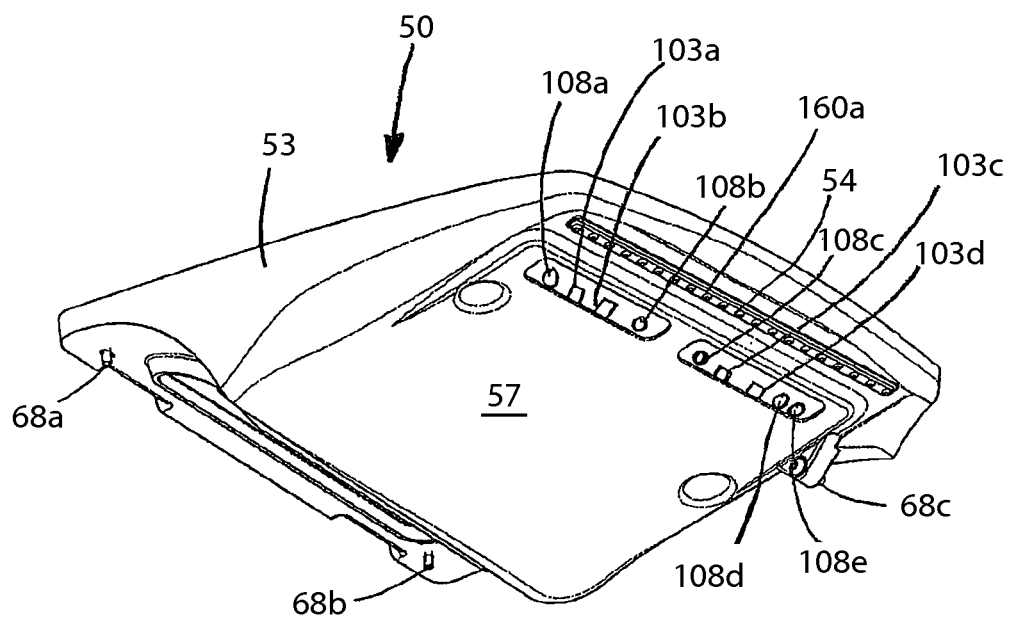
FIG. 7 is a partially exploded lower view of the hand dryer showing the top portion, upper air outlet, and hand dryer sensors.

As best shown in FIG. 7, one embodiment includes a top wall or base 57 that attaches to the backsplash 32 (not shown) and countertop 30 (not shown) preferably with bolts 68a and 68b. A side anchoring screw 68c is also provided to attach the top portion to side wall 62 (see, e.g., FIG. 9). The top portion 53 preferably also has multiple sensors 103a-d and LED lights, e.g., 108a-e located therein and preferably covered by a window to protect them from splashing water and debris. A moisture sensor 106 may also be included for sensing the moisture content on a person's hands. A microcontroller 99, shown in FIG. 16, may determine the optimum time to activate the hand dryer based on the sensed moisture.

Figure 8:
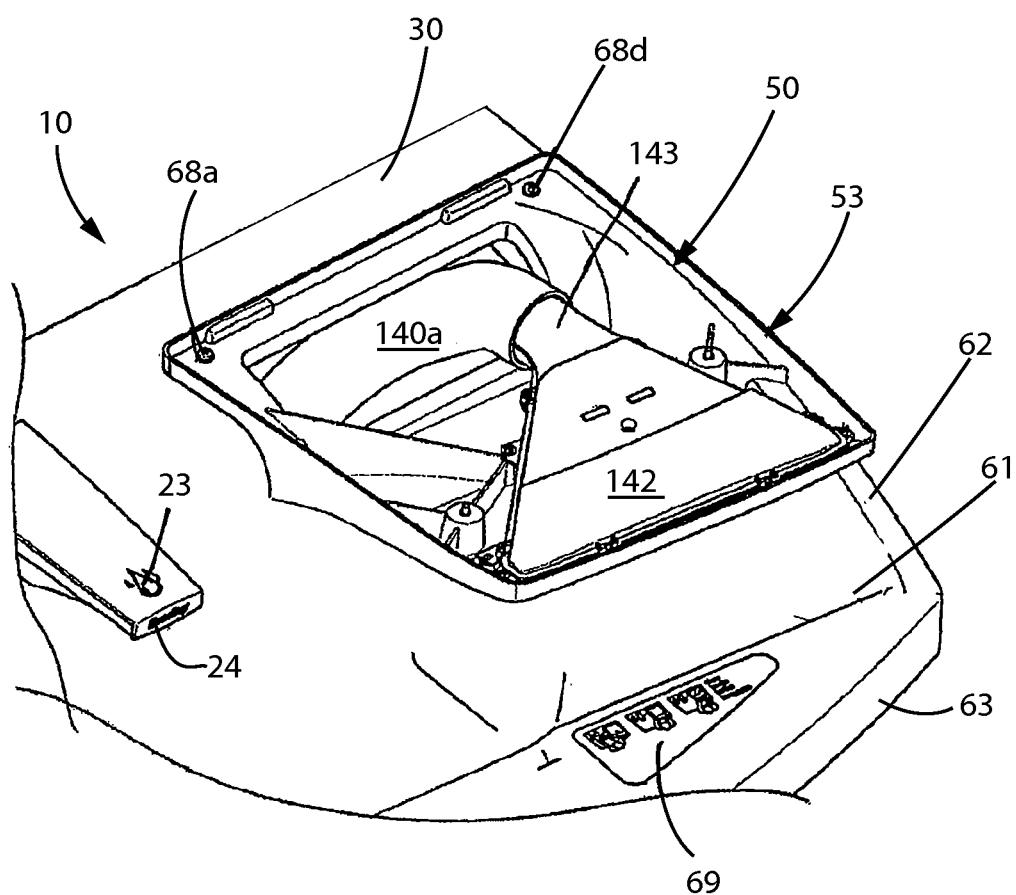
FIG. 8 is a partially exploded upper view of the top portion showing the upper plenum.

FIG. 8 shows the top portion 53 of the hand dryer 50 with the top cover 58 removed. Inside the top portion 53 is a hose 140a which attaches to a first or upper plenum 142. The hose 140a is connected to the first or upper plenum air inlet 143 (see, e.g., FIG. 11) to provide air to the upper plenum 142.

Figure 9:
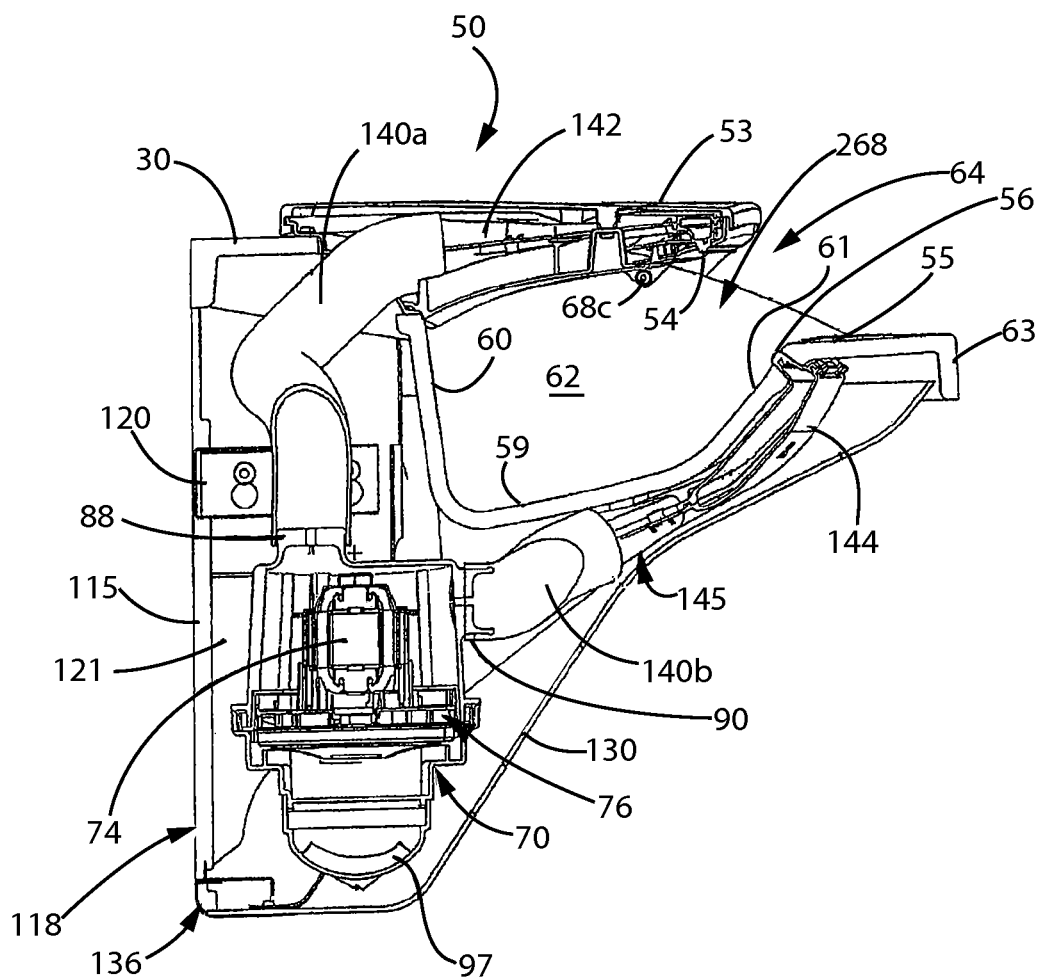
FIG. 9 is a side cross-sectional view of the lavatory system showing the hand dryer, motor, upper plenum, and lower plenum.
Figure 10:
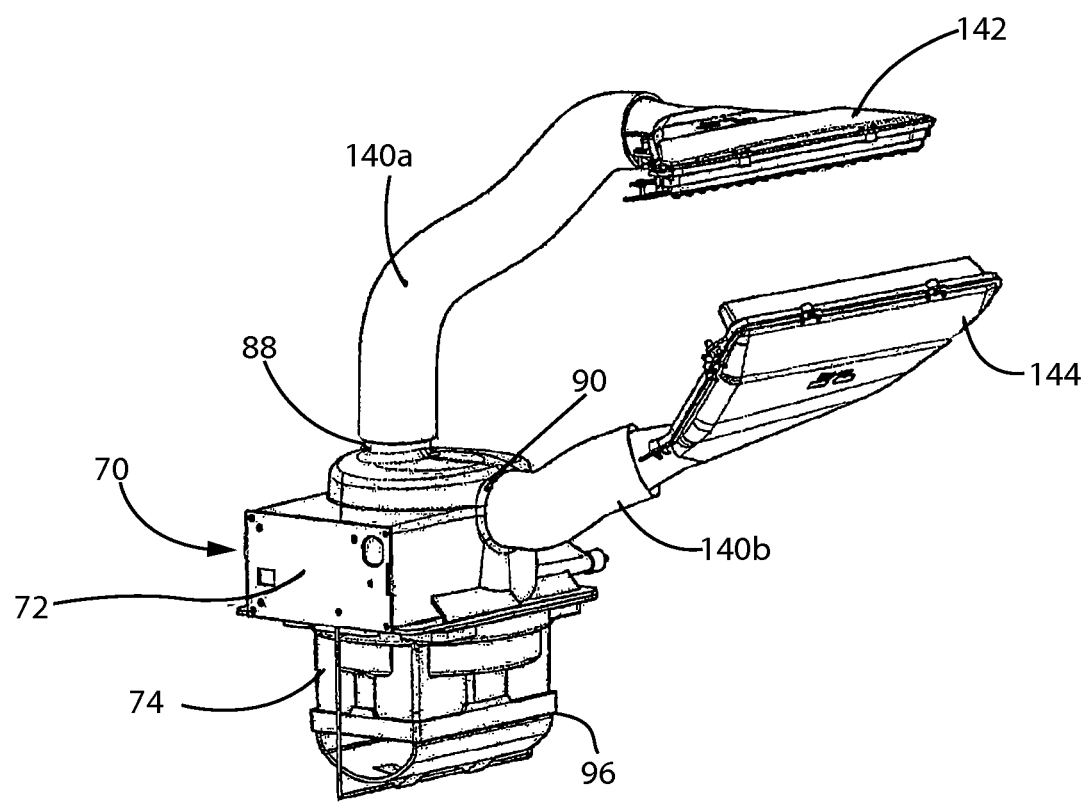
FIG. 10 is a partially exploded view of the lavatory system showing the hand dryer motor, upper plenum, and lower plenum.

As shown in FIGS. 9 and 10, a second, or lower plenum 144, is also provided to the hand dryer 50. The lower plenum 144 is connected to a hose 140b which delivers air to the lower plenum 144 via a lower plenum air inlet 145. The preferably flexible hoses 140a and 140b are attached to a first outlet port 88 and a second outlet port 90 which are preferably on or part of a motor housing 70. A motor 74, with a fan 76 (see, e.g. FIG. 16), provides air to the hand dryer 50. The air outlets 54, 56 are configured in such a way so that they provide air into the hand-receiving cavity 52 (see, e.g., FIGS. 5 and 6B) downwardly and back toward the back wall 60. For example, in one embodiment, the two outlet or exhaust ports 54, 56 are offset from one another in horizontal planes, i.e., the lower plenum 144 nozzle holes 164b are at about a 37 degree angle from horizontal and located closer to the user than the upper plenum 142 nozzle holes 164a which are at about an angle of 1 degree rearward from vertical and located closer to the backsplash 32 of the hand dryer cavity 52. This configuration reduces the chance of water splashing onto the user of the dryer 50. FIG. 10 shows the motor 74 and motor housing 70 of hand dryer 50 operably connected to plenums 142, 144. As shown, the motor housing 70 preferably has an aluminum cover plate 72 and an intake cover 96.

Figure 11:
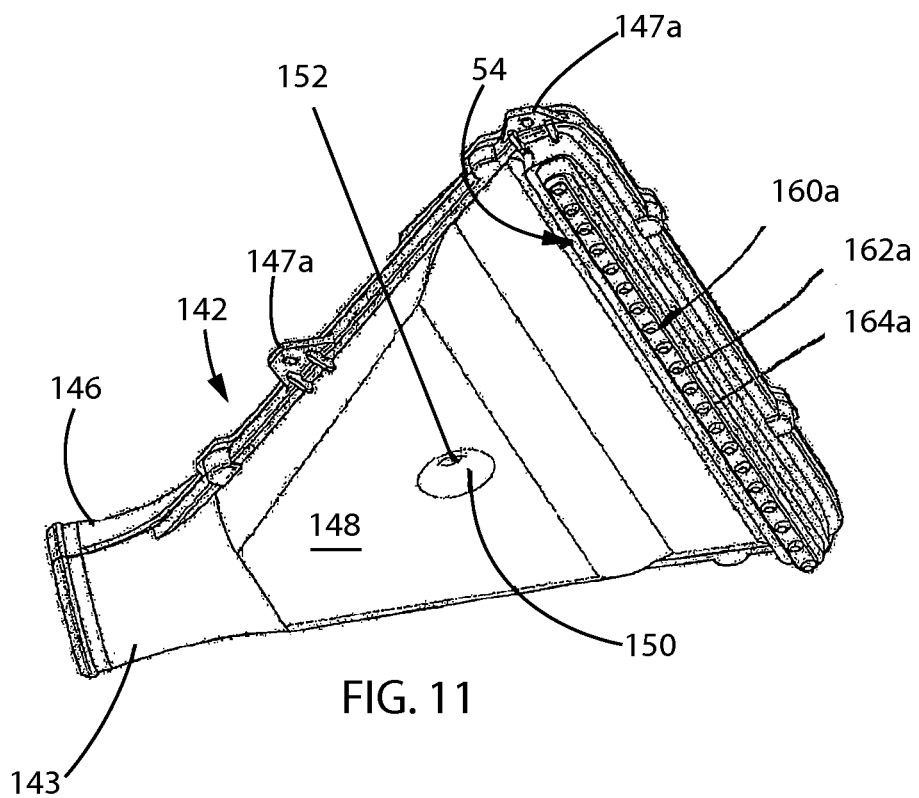
FIG. 11 is a lower view of the hand dryer upper plenum of the lavatory system according to the present invention.
Figure 12:
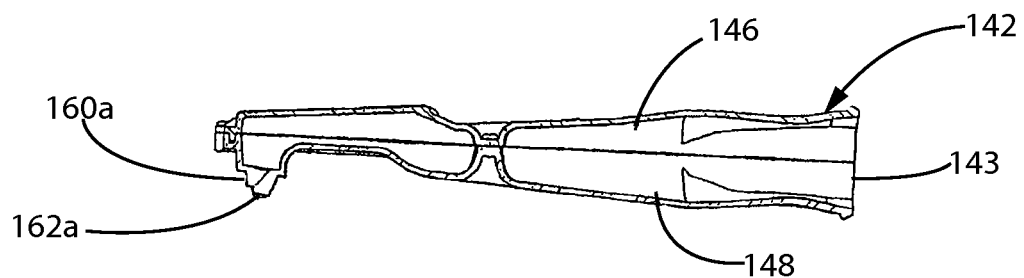
FIG. 12 is a side cross-sectional view of the hand dryer upper plenum of the lavatory system according to the present invention.

FIGS. 11 and 12 show the upper plenum 142 in detail. The upper plenum 142, preferably, is constructed of a top piece 146 and a bottom piece 148. The upper plenum air inlet 143 is preferably integral with the upper plenum's 142 top piece 146 and bottom piece 148. A center post 150 and a screw 152 may be used to connect the top piece 146 to the bottom piece 148. Plastic bonding techniques, such as adhesives, may also be used. Additional screws and posts may also be provided along the outside of the plenum 142. The plenum 142 preferably has top nozzles 160a molded into it to provide the top portion upper air outlet 54. The top nozzles 160a preferably include pointed or frustoconical nozzle tips 162a that have nozzle holes 164a therethrough. The upper plenum 142 has multiple projections or tabs 147a protruding therefrom. The projections 147a act as connecting points for screws to attach the plenum of hand dryer 50 to the lavatory system 10.

Figure 13:
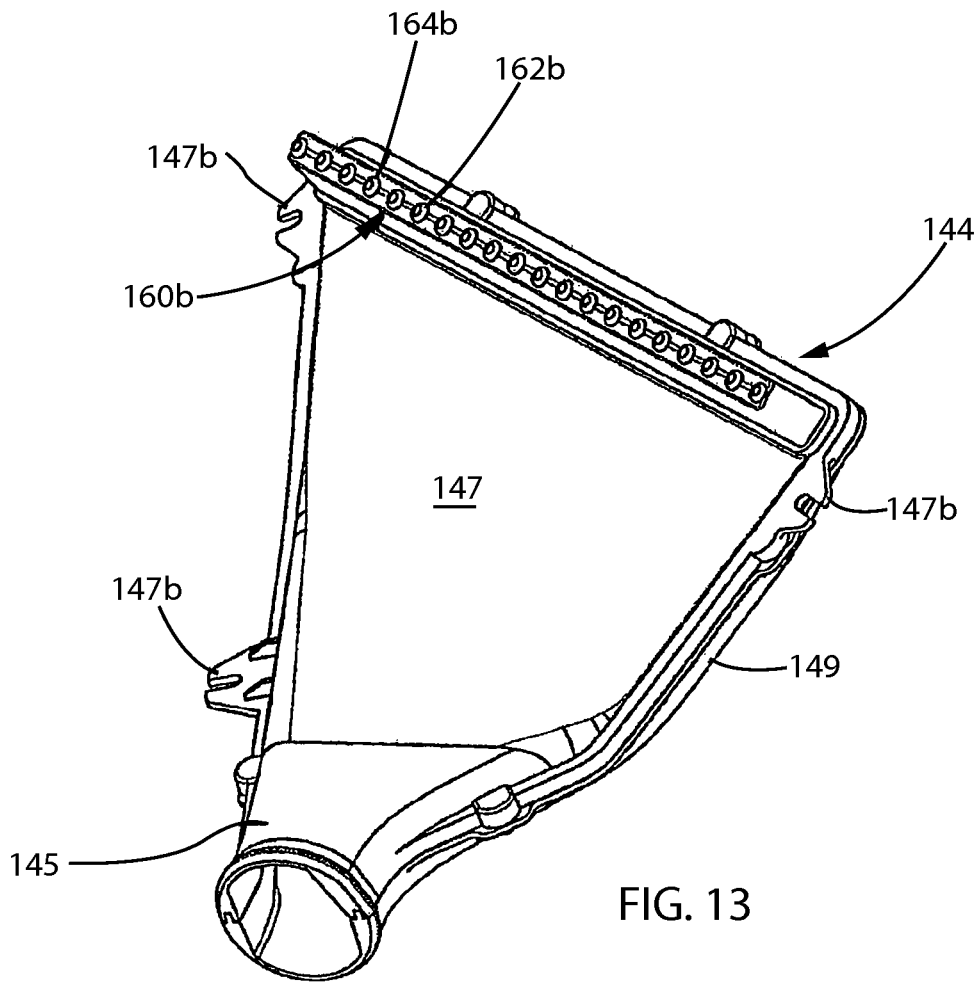
FIG. 13 is an elevation view of the hand dryer lower plenum of the lavatory system according to the present invention.
Figure 14:
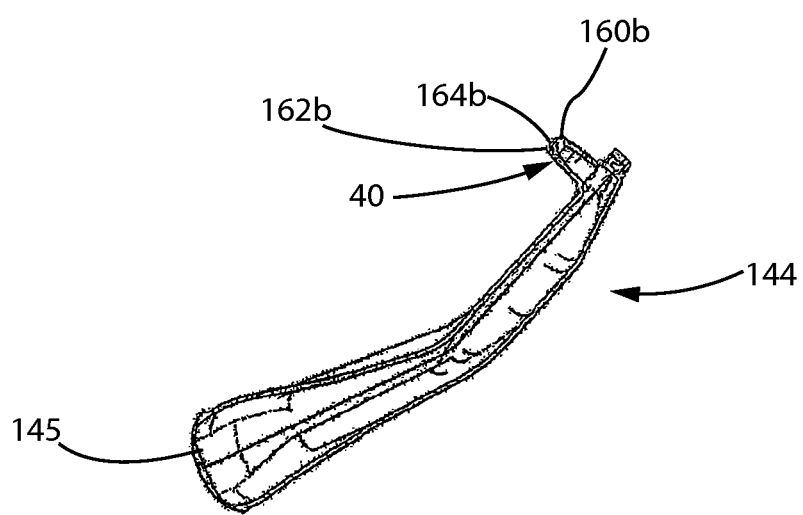
FIG. 14 is a side cross-sectional view of the hand dryer lower plenum of the lavatory system according to the present invention.

As shown in FIGS. 13 and 14, the lower plenum 144 is similarly configured. The lower plenum 144 has a top piece 147 connected to a bottom piece 149, preferably by bonding and/or posts and screws. A lower plenum air inlet 145 is also provided. The lower plenum air inlet 145 is preferably integral with the rest of the lower plenum 144. The lower plenum 144 also has multiple projections or tabs 147b protruding therefrom which act as connecting points for screws to attach the plenum 144 to the lavatory system 10. Like the upper plenum, the lower plenum 144 is preferably constructed of two injection-molded plastic top and bottom pieces bonded and/or screwed together. The lower plenum may also contain a center post screw (not shown) to minimize deflection of the plenum when pressurized.

Bottom nozzles 160b are provided, again, preferably by molding into the lower plenum 144. Lower nozzles 160b, like the upper nozzles 160a, preferably have protruding frustoconical nozzle tips 162b each of which has a nozzle hole 164b therethrough. The shape of the nozzle tips 162b on the lower plenum 144 further acts as a flood prevention mechanism 40 to protect the motor 74.

Figure 15:
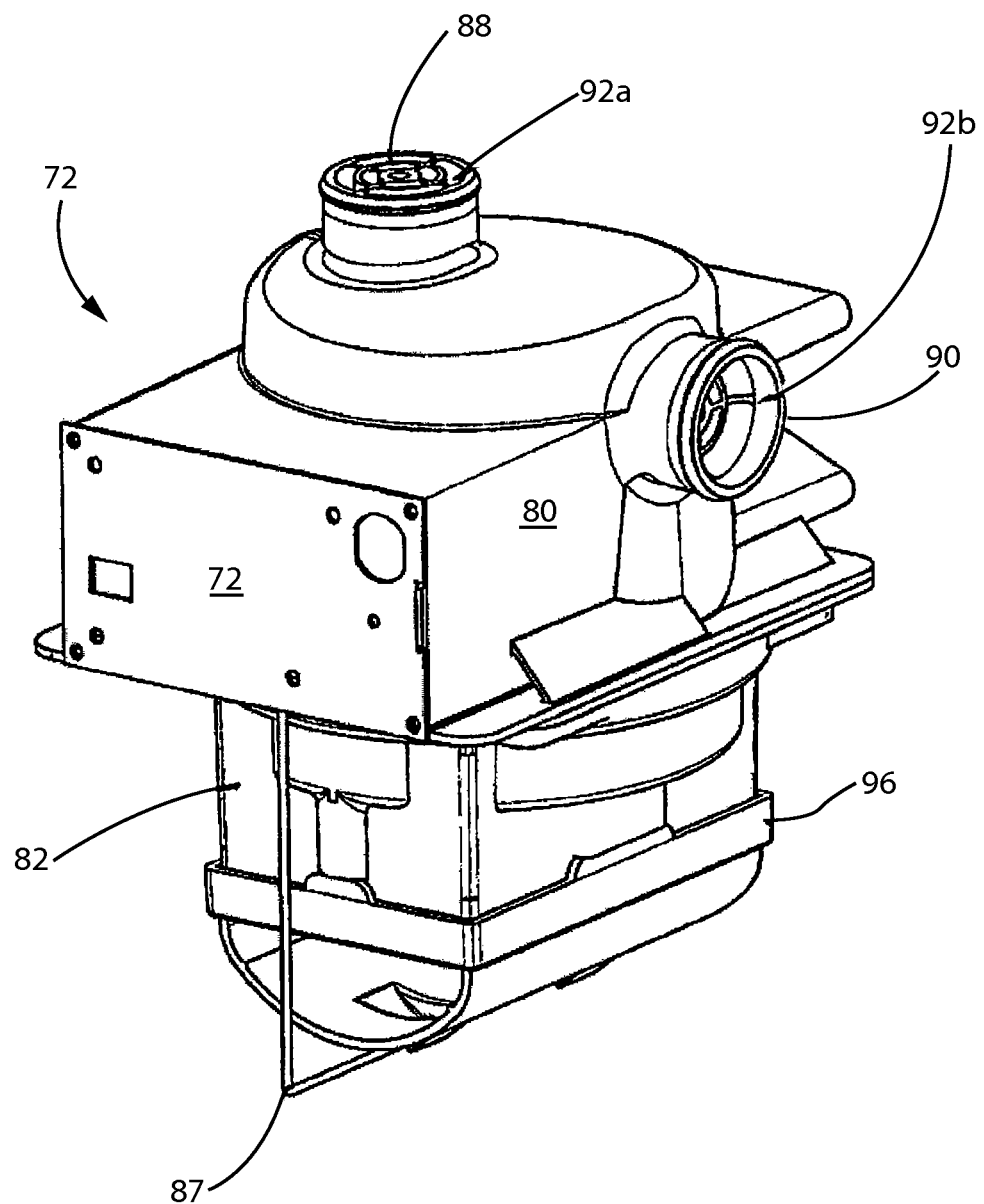
FIG. 15 is an elevation view of the hand dryer motor of the lavatory system according to the present invention.
Figure 16:
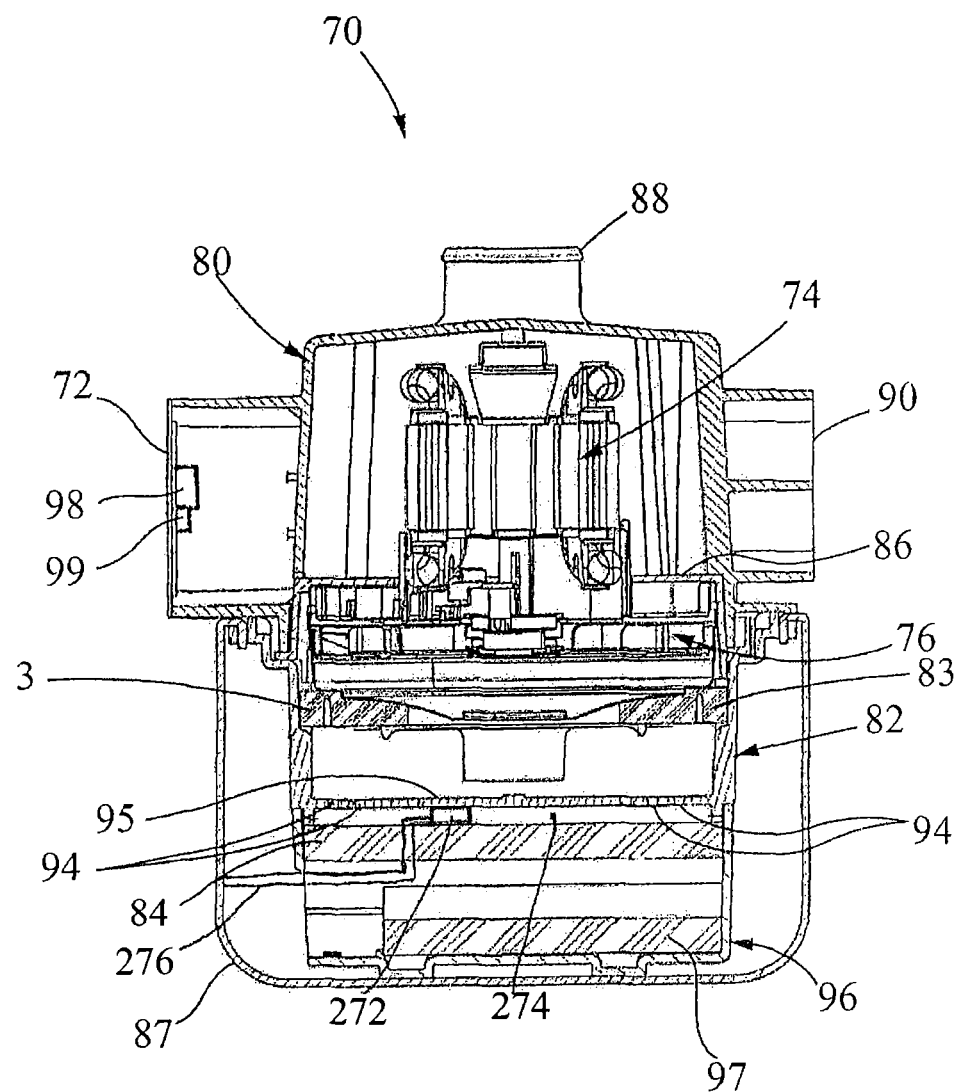
FIG. 16 is a side cross-sectional view of the hand dryer motor of the lavatory system according to the present invention.

The hand dryer blower motor 74 and motor housing 70 are best shown in FIGS. 15 and 16. Motor housing 70 includes an aluminum cover plate 72 and an upper or outer casement 80. An intake air manifold cap or housing cap 82 is provided toward a lower end of the motor housing 70. The motor 74 is inside the motor housing 70 and has a fan 76 with blades (not shown). Preferably, a rubber motor mounting ring and/or housing isolation gasket 86 is also provided. This gasket 86 helps reduce vibrations and deaden the motor's sound. A filter 84 is preferably provided within the housing 70 to filter the intake air. The filter 84 is preferably constructed of HEPA media or other suitable media. Also contained within the motor housing 70 is acoustic insulation foam 83 to further isolate and lessen motor noise. The intake air portion or lower portion of the housing cap 82 is configured with a solid center section 95 surrounded by a circular pattern of holes 94. This configuration is spaced at a distance similar to the half wave length of the fan blade passing frequency of the fan motor 74. As a result, acoustical waves are reflected off of the solid center section 95 on the bottom of the housing cap 82 at a fan cowling and the acoustical foam 83, and eventually propagate through the circular hole pattern 94 in an attenuated manner.

A filter or intake cover 96 may also be provided in the housing 70 to contain or to hold the filter 84 in place. To further attenuate sound generated by the fan motor 74, insulation or acoustical foam 97 is placed on the inside of the intake cover 96. The cover 96 is preferably further configured to redirect the intake air 90 degrees from the axial center of the fan 76 and motor 74. This design promotes reflection of acoustical waves off of the noise reducing acoustical foam 97. A wire 87 is provided to keep the filter cover 96 in place.

As shown in FIG. 15, the first outlet port 88 and second outlet port 90 may include first outlet port grate 92a and second outlet port grate 92b, respectively, to prevent fingers or hands from accidentally being pushed into the motor 74 (not shown). These grates are preferably integrally molded into the port outlets.

Referring to FIG. 16, in one preferred embodiment, a motor control board or circuit board 98 is contained in the housing 70 and includes a motor control, e.g., a microcontroller 99, for turning the motor on/off and further controlling the motor 74. This microcontroller 99 may be in communication with several other sensors and/or subsystems, as will be described more fully below. The board 98 is preferably in communication with aluminum plate 72 which acts as a heat sink to channel heat away from the board 98. The plate 72 also acts as mounting platform for the board 98.

Figure 18:
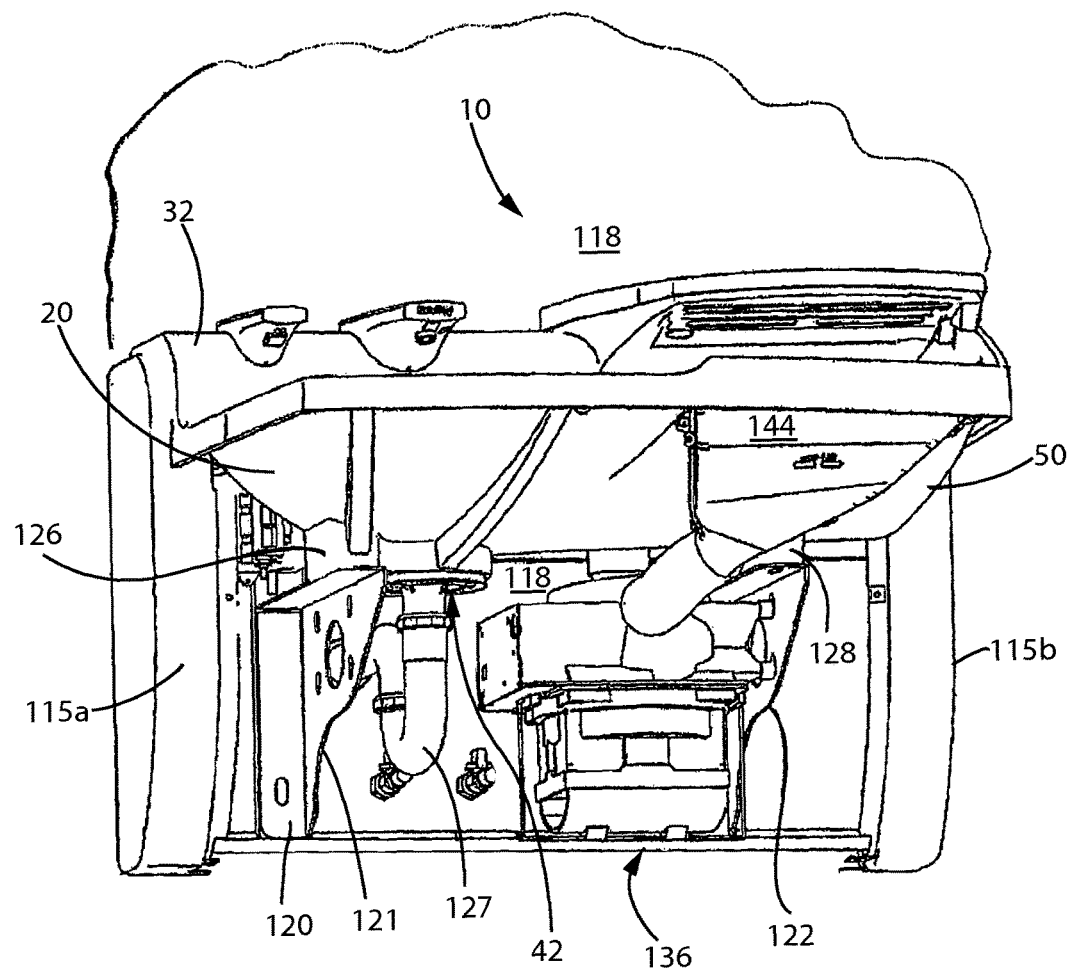
FIG. 18 is a lower front view of the lavatory system according to the present invention with a cover removed to show the mounting hardware.

As shown in FIG. 18, the lavatory system 10 is preferably attached to a lavatory wall 118 and can be mounted at different heights to accommodate adults, children, and those with disabilities. A frame 120 may be connected to the lavatory wall to support the lavatory system 10. The frame 120 preferably has two triangular-shaped brackets 121, 122 having flat surfaces support columns 126, 128 on an underside of the wash basin 20 and hand dryer portion 50. A drain pipe 127 connects the drain 42 (see, e.g., FIG. 2) to the lavatory's plumbing behind the lavatory wall 118. Screws or other fastening means secure the brackets in place.

The frame 120 and drain pipe 127 (FIG. 18) are preferably covered by a lavatory system cover 130 as seen in FIGS. 1 and 2. The lavatory system cover 130 not only conceals the frame, motor, electrical connections, and plumbing, but it also preferably reduces the sound level experienced by the user. The cover 130 preferably also has brand indicia 131 and other user instructional indicia contained thereon. First end cap 115a and second end cap 115b help secure the cover 130 to lavatory system 10. The end caps 115a, 115b are preferably made of stainless steel and the cover 130 is preferably made of a plastic and/or resin material, e.g., a Class A fire-rated polymer. A primary air inlet 136 (see, e.g., FIG. 9) is preferably provided by creating a small gap between the lavatory wall 118 and the cover 130. The gap provides noise attenuation and also prevents foreign objects from getting sucked into the primary air inlet 136.

Figure 19:
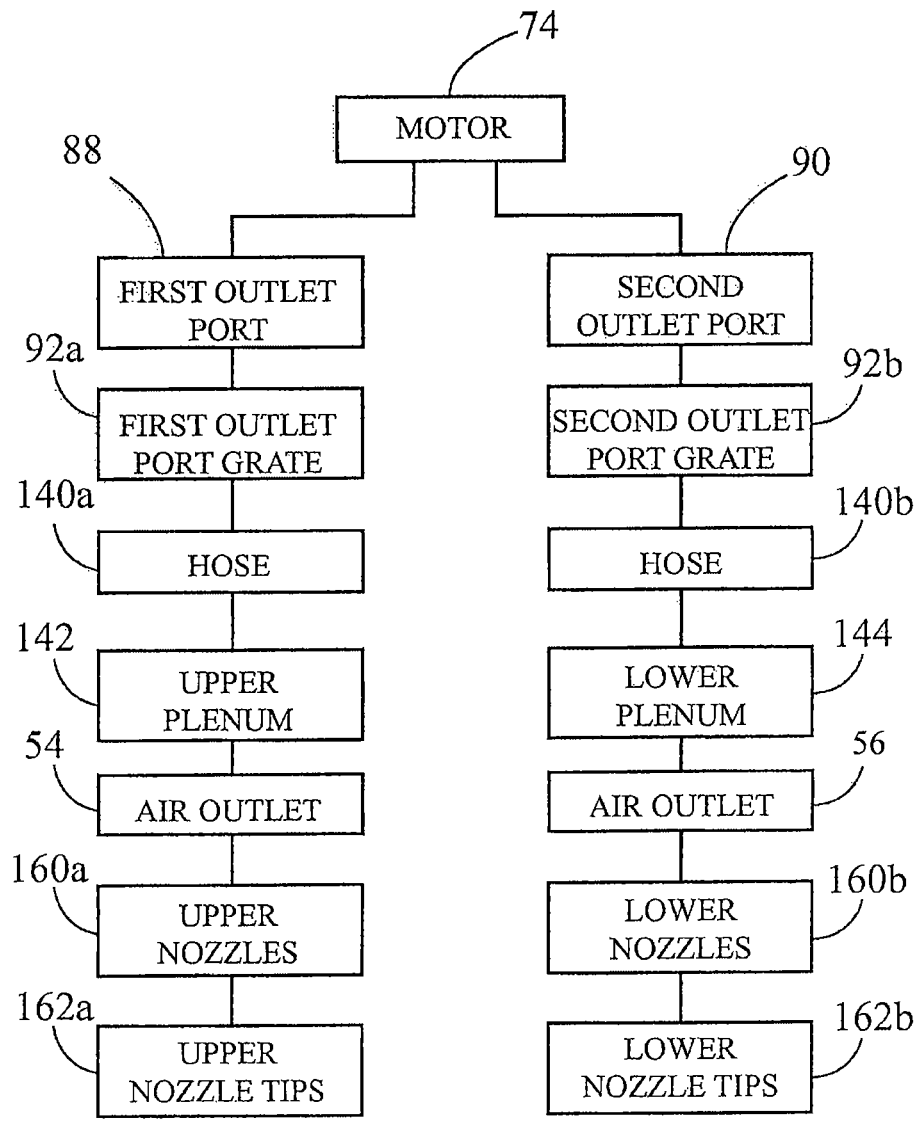
FIG. 19 is a block diagram showing a preferred air flow path from the hand dryer motor.

FIG. 19 is a diagram showing a preferred air flow from the motor 74 out the first outlet port 88 and second outlet port 90. From the first outlet port 88, the air travels up through a grate 92*a* and via a hose 140*a* to a first or upper plenum 142 and out an air outlet 54. The air outlet 54 channels the air through individual upper nozzles 160*a* having upper nozzle tips 162*a* with air holes and into columns of air directed downwardly at a user's hands in the cavity. From the second outlet port 90, the air travels through a second outlet port grate 92*b* and via a hose 140*b* to a second or lower plenum 144 and out an air outlet 56. The air outlet 56 channels the air up through lower nozzles 160*b* having lower nozzle tips 162*b* with air holes and into columns of air directed outwardly at a user's hands in the cavity.

In a preferred embodiment, upper and lower nozzle tips 162*a*, 162*b* connected to the nozzles 162*a*, 162*b* emit high speed colliding columns of air to shear water off the user's hand. The tips, holes, and resulting air columns are spaced and calibrated in such a way as to reduce forces on the user's hand which would otherwise move the hand toward the upper or lower plenums or the side surfaces. As mentioned, one way of accomplishing this spacing and calibration is to have the axis of the air flow from upper plenum 142 nozzle holes 164*a* angled about 1 degree from vertical and aimed toward the cavity back wall 60 (FIG. 9) and the axis of the air flow from lower plenum 144 nozzle holes 164*b* angled about 37 degrees from horizontal and aimed toward the cavity back wall 60. Moreover, the upper to lower nozzle tip spacing may be about 3.5 inches apart and the hand-receiving cavity 52 (see, e.g., FIG. 5) may have width of about 9.5 to 10 inches to provide the user with optimal comfort when using.

In one embodiment, the nozzles 160*a*, 160*b* preferably have tips 162*a*, 162*b* that are pointed protrusions that help pull static air into the air columns. These rows of nozzles are preferably mounted on two, approximately ten inch, rectangular blocks or blades that fit, respectively, into the top and bottom air outlets 54, 56. The blades are preferably integral with the upper and lower plenums 142, 144. There are approximately 20 nozzles with tips formed or molded into each blade. These tips are approximately 0.050-0.060 inches long and have a diameter at the base of approximately 0.160-0.220 inches. The holes therein are preferably about 0.101 inches in diameter. From the center of one nozzle hole to the center of the next nozzle hole, it is preferably about 0.50 inches. As mentioned, the tips 162*a*, 162*b* preferably have a generally frustoconical shape to help prevent water from entering the nozzles 160*a*, 160*b* and also have about a 6 degree taper. In one preferred embodiment, the tips have a smooth, slightly rounded side wall to prevent catching of clothing or jewelry. When the dryer 50 is in use, the user's hands are preferably about 0.75 inches away from the nozzle tips.

As discussed, in one embodiment the nozzles and holes on the top blade and the nozzles and holes on the bottom blade are at different angles from the horizontal plane and vertically aligned with one another so that the collision of the upper and lower streams of air provide a unique air flow pattern. This configuration helps to generate an s-shaped airflow pattern. However, in another alternative embodiment, the holes and nozzles are lined up directly across the cavity from each other.

In one embodiment, the bidirectional or dual-sided dryer uses 1600 watts (or 13.7 amps) and will dry hands in about 15 seconds at 80 decibels (dB) with 70 cubic feet per minute (CFM). In this embodiment, the dryer runs off a 120V outlet and requires a dedicated 20 ampere (amp) circuit. Ground fault interruption (GFI) circuit protection is preferred.

Figure 17:
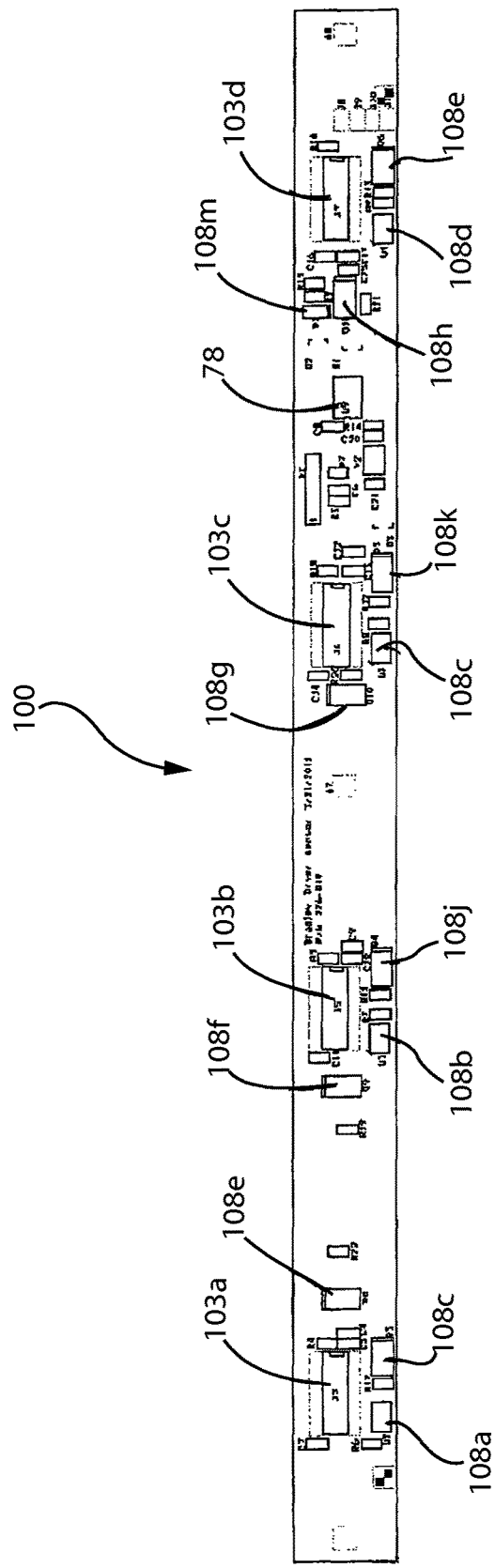
FIG. 17 is a view of the sensor board of the lavatory system according to the present invention.

Referring now primarily to FIG. 17, a sensor control board 100 is preferably provided in the top portion 53 near the upper plenum 142 (see, e.g. FIG. 9). The sensor control board 100 includes a microcontroller 78, and a multitude of sensors 103*a*, 103*b*, 103*c*, 103*d*. In the preferred embodiment, four proximity sensors are provided in series each of which works through triangulation to detect an object or user's hand in the cavity 52 (see, e.g., FIG. 5). Lights or LEDs 108*a-m* may also be mounted to the control board 100. Some or all of the LEDs 108*a-l* may be activated when the sensors 103*a-d* detect an object in the hand-receiving cavity 52.

In one preferred embodiment, the LEDs 108*a-m* are operably connected to the hand dryer 50. For example, LEDs 108*a-d* continuously illuminate the hand-receiving cavity 52 at a low intensity level when a sensor does not detect the presence of an object, i.e., the cavity is not in use or in "stand-by". However, when a sensor detects that an object has entered into the hand-receiving cavity 52, and during dryer 50 activation, preferably the LEDs 108*e-h* and 108*i-l* also illuminate the cavity and thus increase the overall intensity level of light in the cavity. In another embodiment, LEDs 108*a-d* do not begin to illuminate the cavity until the soap is dispensed or the water begins to flow in the basin. Further, this illumination turns off at a preset period after the last dryer use—e.g., to save energy.

In a preferred embodiment, when a staff member wishes to clean and service the lavatory system 10 the staff member may engage a service mode. Here the LEDs 108*a-d* and 108*e-h* continuously illuminate the hand-receiving cavity 52. Activation of hand dryer 50 is also suppressed by communication between microcontroller 78 and microcontroller 99. In one embodiment, service mode activation is accomplished by triggering a sensor, e.g., the right-most sensor 103*d* in the upper portion of the hand-receiving cavity 52, for an extended time period. Thus, if this one sensor consistently detects an object in the hand-receiving cavity 52, the hand dryer 50 is disabled for about 30 to 60 seconds and some of the LEDs, e.g., LEDs 108*e-h*, may be illuminated at a high-intensity level. This allows the hand-receiving cavity 52 to be temporarily cleaned without further engaging the hand dryer 50.

The LEDs, e.g., 108*i-l*, may flash in certain ways when the service mode has been started and/or is about to end. For example in one embodiment, prior to the service mode, one row of 4 white LEDs provides lower level illumination of the hand dryer cavity. However, if the rightmost sensor is triggered within the last 2 seconds and if a hand is placed over the rightmost sensor for the period of 3 seconds, a row of 4 amber LEDs will rapidly flash twice to designate that the unit is entering the service mode. At the same time, a second row of 4 white LEDs will turn on to increase the illumination of the hand cavity for approximately 30 seconds to assist in cleaning. After approximately 25 seconds from when the service mode was started, the row of 4 amber LEDs will flash three times to indicate that the service mode cycle is nearing completion. At the end of the service mode cycle (5 seconds after the 4 amber LEDs flash three times or about 30 seconds in total service cycle length), the second row of white LEDs will turn off and the hand dryer cavity will remain lit at the lower level of illumination by the first row of 4 LEDs.

In one embodiment, the service mode includes a microcontroller with a programmed touchless cleaning mode feature wherein if one sensor is the only sensor activated within the last two seconds and if activated continuously for about three seconds, the hand dryer 50 will enter the mode to allow cleaning of the hand dryer 50. This mode lasts for about 30 seconds without activation of the dryer and then the microcontroller will return the system to normal operation. The microcontroller will flash the LED lights twice when entering the cleaning mode and three times when approaching a time near the end of a cleaning cycle which is approximately 25 seconds into an about 30 second cleaning cycle. If the cleaning mode is longer in another embodiment, the lights will flash 3 times 5 seconds before the end of the cleaning cycle.

Figure 20:
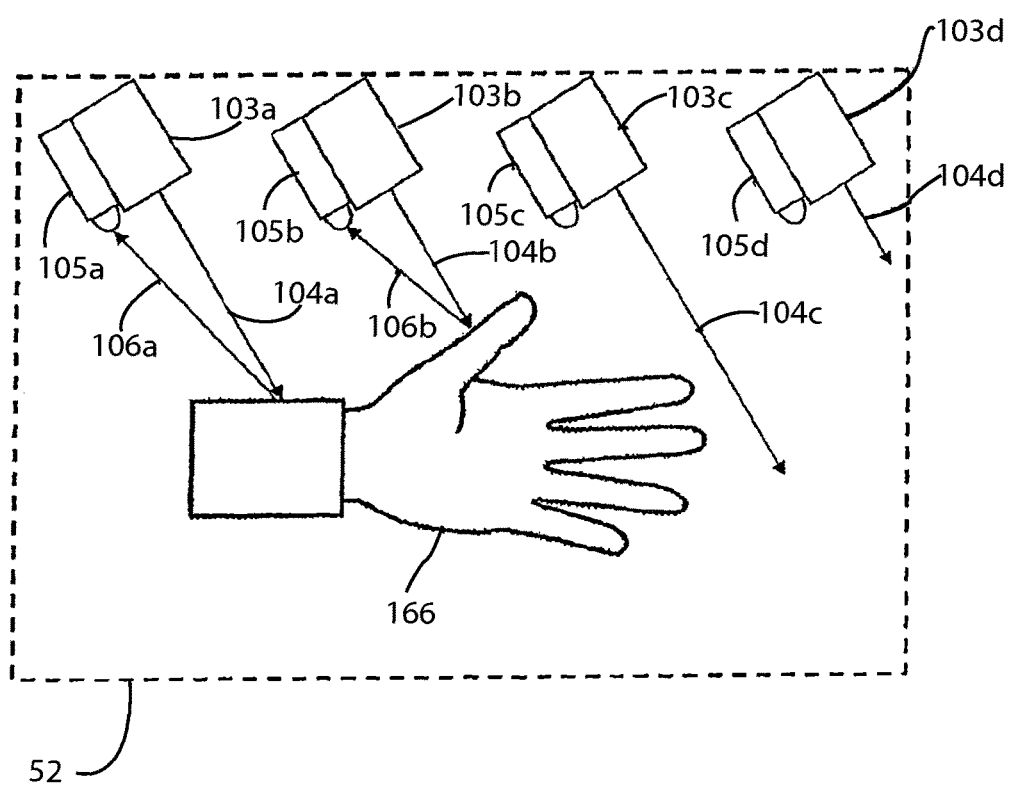
FIG. 20 is a diagram showing the hand dryer sensors according to the present invention interacting with a hand.

FIG. 20 is a diagram showing triangulation of the sensors 103a-103d in detecting an object in the hand-receiving cavity 52, e.g., a user's hand 166. In a preferred embodiment, it should be noted that hand entry occurs at an oblique angle. Hand 166 entry angles range from approximately 5 to 50 degrees from horizontal depending on the user's height and the mounting height of the lavatory system 10. For example, sensors 103a-d may be infrared (IR) sensors with emitter sections emitting IR light 104a-d, respectively. The IR light 104a and 104b may be reflected by hand 166. Each IR sensor 103a-d also has a detection module 105a-d, respectively.

The sensor detection modules 105a and 105b utilize an internal triangulation algorithm to sense IR light, 106a and 106b respectively, when an object is in the sensor's field of view. When a user's hand 166 enters the hand-receiving cavity 52, the sensor detection modules 105a and 105b output an electrical signal e.g., a 5-volt signal. This signal is used by the microcontroller 78 to determine whether to activate the hand dryer (50) and LED lights 108e-l (see FIG. 17).

Figure 21:
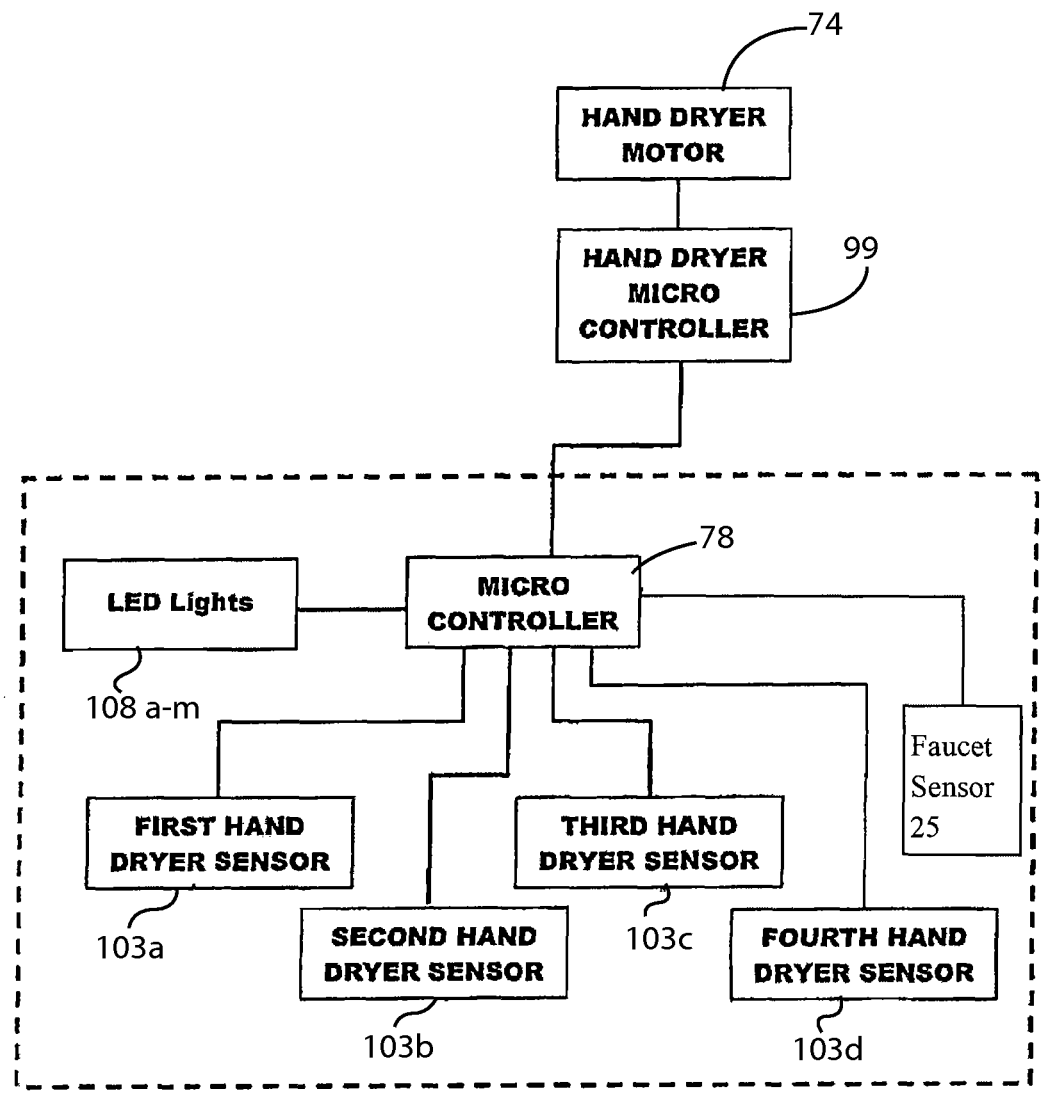
FIG. 21 is a block diagram showing the hand dryer electrical components.

FIG. 21 is a diagram showing a preferred electronic control communications embodiment. In this embodiment, at least one microcontroller 78 communicates with the various subsystems, e.g., the first, second, third, and fourth hand dryer sensors 103a-d, LED lights 108a-l, and hand dryer 50 (including hand dryer motor's microcontroller 99). In this embodiment, the microcontroller 78 may include a pre-programmed programmable unit having a time delay mechanism for turning the subsystems on and off in a certain sequence. For example, the delay may be approximately 400-800 ms. Of course, it is appreciated that one or more microcontrollers may be used, for example, one for each subsystem, and may therefore be configured to communicate with each other. In one embodiment, a sensor control board or circuit board 100 (see, e.g., FIG. 17) is provided and includes a microcontroller 78 and a single bank of sensors (103a-d) to measure distance by triangulation. There may also be present on this sensor control board 100, LEDs 108a-d that will continuously illuminate the hand-receiving cavity 52. LEDs 108e-h and LEDs 108i-l may also be present and illuminate when the sensors 103a-d detect a user's hand 166 in the cavity. In one embodiment, white lights are used when the dryer is in stand-by, and amber lights are used when the dryer is in use.

A programmable unit may be present on the sensor control board 100 and/or motor control board 98 and preferably includes a time-delay mechanism, for example, in communication with an on/off switch for the motor 74. In this embodiment, when one of the sensors 103a-d is activated by an object in the hand-receiving cavity 52, the microcontroller 78 rechecks the activated sensor multiple times to validate that an object is in the hand-receiving cavity 52. Then the delay mechanism allows users to enter their hands 166 fully into the hand-receiving cavity 52 prior to the hand dryer motor 74 achieving full speed. This minimizes the potential of any splashing of water back on the user as a result of the fully active hand dryer imposing a shearing action on water present on the user's hands. There may be additional sensors (not shown) that may inhibit the dispensing of water or soap or activation of the dryer when a critical water level is reached in the wash basin and thus prevent overflow, flooding, and/or motor damage.

In one embodiment, multiple distance sensors 103a-d utilize triangulation one at a time and from left to right in their field of view to detect an object. These sensors are preferably positioned so they are recessed in the upper portion 53 and aimed vertically into the hand-receiving cavity 52. Recessing is minimal, however, to avoid adversely impacting sensor operation. In one embodiment, the sensor board 100 is programmed to check all sensors at about 130 milliseconds (ms) intervals. When a sensor flags a detection, it is then rechecked 15 times over about a 15 ms period to ensure the detection was not a false trigger.

The temperature rise of the air during a drying cycle is dependent upon how long the user keeps the hand dryer 50 activated. Since the system 10 does not use an auxiliary air heater, the air temperature rise is a result of the heat generated by the inefficiency of the motor 74. The other factor dictating the motor temperature rise is how frequently the motor 74 is activated. In a high usage environment (airport, sports arena, etc.), the motor 74 will not typically cool down very much between cycles and the air temperature rise experienced by the user will be significantly higher than that of a hand dryer which operates infrequently. The following chart shows some typical temperatures.

| Drying Cycle | Cycle Length | Expected Temperature Rise Above Ambient Temperature (F.) @ 120 V (rated operating voltage) |
| --- | --- | --- |
| Normal | 12-15 seconds | 12-50 |
| Maximum | 30 seconds | 22-50 |

In one embodiment, additional safety and cleaning features may be present. For example, UV lighting or some other sterilization technique to disinfect the hand-receiving cavity 52 may be provided. Further, only one drain may be provided between the wash basin 20 and outside of hand-receiving cavity 52 to eliminate the need for another device to catch water from the dryer 50 that must be emptied and can collect harmful molds or germs. Certain dryer components, like the nozzles 160a, 160b, may have an antimicrobial additive molded into the plastic. Further, the entire wash basin 20 and hand-receiving cavity 52 may be constructed, in part, of an antimicrobial material or may be coated with such a material during manufacture.

In one embodiment, a second row of holes, a slot, and a port are present to provide a lower velocity air stream to further minimize water splashing onto a user.

Figure 22:
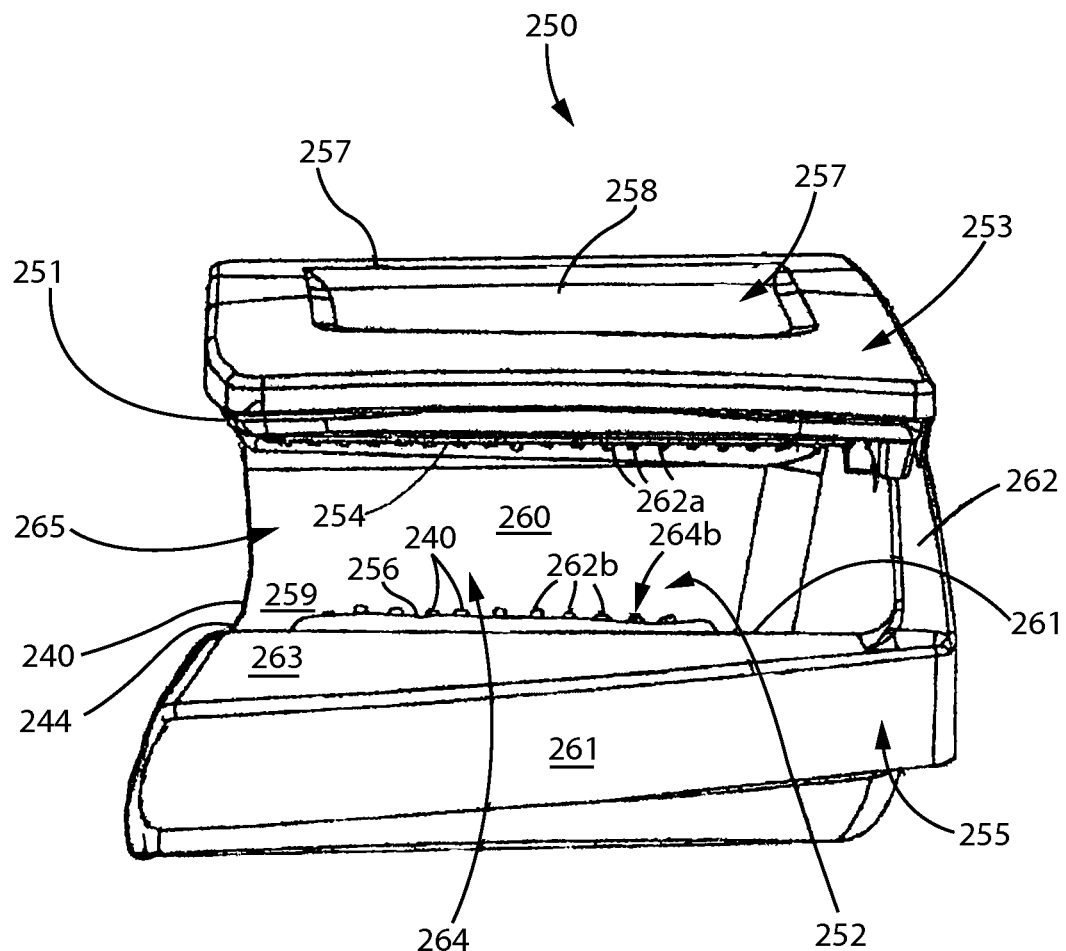
FIG. 22 is a front elevation view of another embodiment of a lavatory system according to the present invention.

In the embodiment shown in FIG. 22, the drying system or dryer 250 may be a stand alone unit but still mounted in close proximity to the wash basin. In this embodiment, lavatory hand dryer 250 includes a hand-receiving cavity 252, a top portion 253, a bottom portion 255, a back side or wall 260, and at least one side wall 262. Note that while a right side wall is shown, the dryer may have only a left side wall. Alternatively, two side walls or partial side walls may be present. The top portion 253 may also include a hood 251 which forms a top wall or side 257 of the cavity 252. The top portion hood 251 may also include a top portion cover which may form a shelf 258. An upper air outlet 254 is also provided in the top or upper portion 253 and incorporates nozzle holes 262a.

A bottom portion 255 includes a lower air outlet 256. The bottom portion 255 is formed, in part, by a bottom wall or side 259. The bottom portion 255 of the hand-receiving cavity 252 also includes a back wall or side 260, front wall or side 261, and side wall 262. A front ledge 263 is integral with the front wall 261. The hand-receiving cavity 252, therefore, is preferably configured to have a front opening 264 and a side opening 265 (see e.g. FIG. 22). The side opening 265 (FIG. 22) allows a user to insert his/her hands into the hand-receiving cavity 252 by moving his/her hands along path 267 as indicated in FIG. 1. In this embodiment, the dryer's configuration and placement preferably allows the user to easily transition the hands from the wash basin to the dryer without dripping water onto the floor.

In one preferred embodiment, a mechanism 240 for preventing flooding and damage to the hand dryer motor is provided as well as to prevent water blown from a users' hands from falling to the floor and creating a slip hazard or unsanitary conditions. The mechanism 240 may include a flood relief rim 244 located on, for example, the left side of the hand-receiving cavity 252 at the opening 265. The flood relief rim 244 is provided below the lower portion's air outlet 256 and the nozzle tips 262b as shown. Thus, water flows over the flood relief rim 244 and not down the nozzle holes 264b and into the motor (not shown). In addition, another motor protection mechanism 240 may be the frustoconical lower nozzle tips 262b which resist the entry of water.

Other preferred embodiments of the hand dryer 250 may include a side wall 262 on the left side and an opening 265 on the right side. In yet another preferred embodiment, the hand dryer 250 may include both a left side, side wall and a right side, side wall (not shown).

The primary components of the inventive lavatory system including the dryer bottom wall, a back wall, and single side wall are preferably formed from a plastic and/or resin material. In one embodiment, the system components may be formed from a solid polymeric and/or a polymeric and stone material. In another embodiment, the system components may be manufactured from Terreon® or TerreonRE® which are low emitting, e.g., Greenguard™ materials and available from the Bradley Corporation of Wisconsin.

Figure 23:
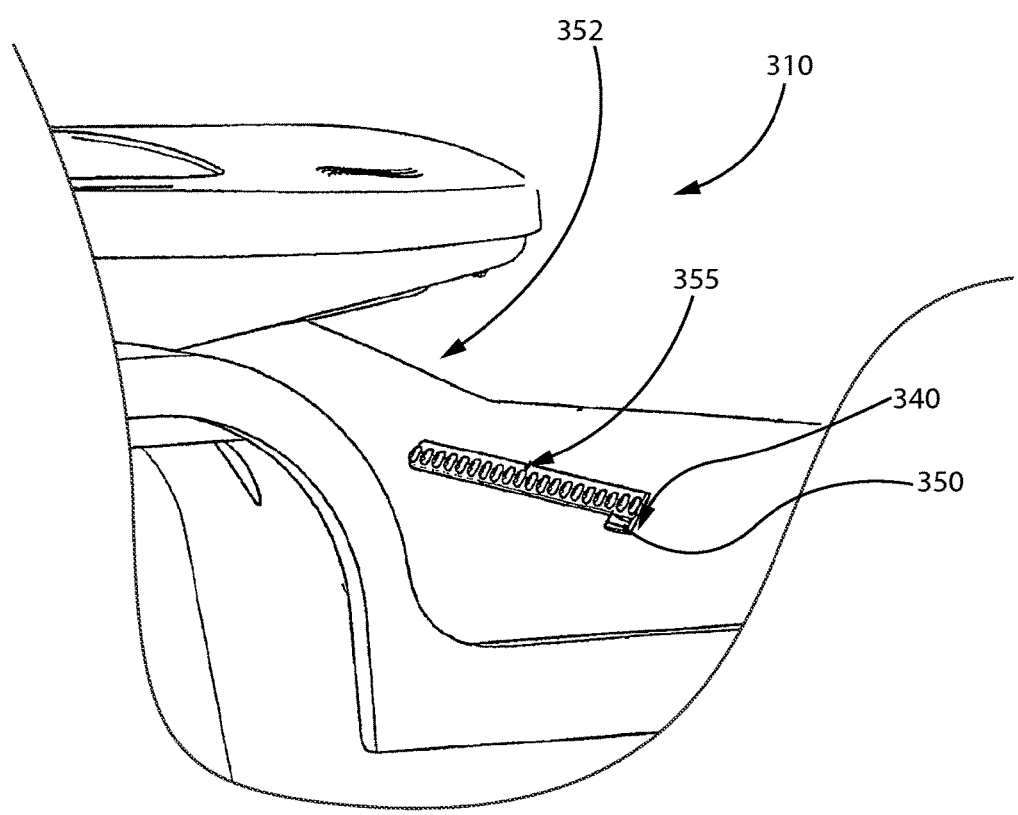
FIG. 23 is a side view of a cutaway portion of still another embodiment of the lavatory system according to the present invention illustrating a hand dryer, drain hole, and lower nozzle portion.
Figure 24:
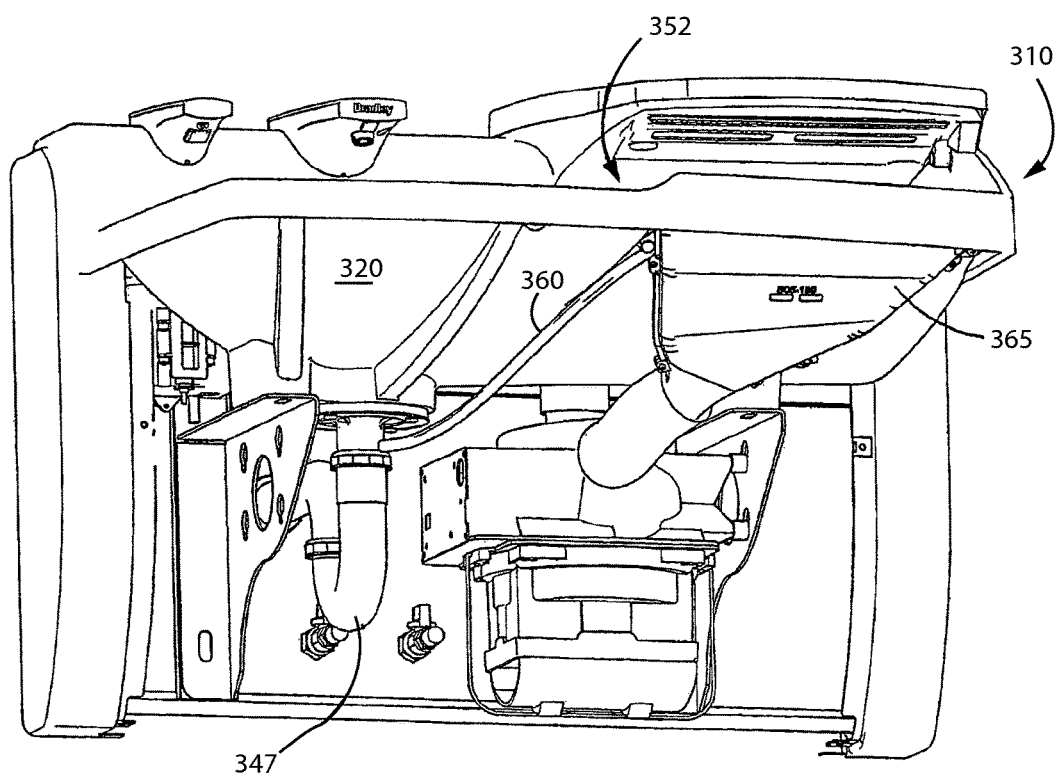
FIG. 24 is a lower front view of the embodiment of FIG. 23 according to the present invention with a cover removed to show a drain tube and drainpipe.

In another embodiment, as best shown in FIGS. 23 and 24, lavatory system 310 has another mechanism 340 to prevent flooding of the motor (not shown). For example, as shown a drainage hole 350 is present in a lower portion of the hand-receiving cavity 352 to preferably provide an integrated overflow drain. Hole 350 is connected a drainage tube 360 and is located slightly below the plenum 365 and plenum outlet 355 and nozzle holes to prevent flooding of the motor. The drainage tube 360 connects to the drainpipe 347 located beneath the basin 320. Of course, as is know in the art, traditional drainage systems, like weep holes in the basin itself, may also be provided.

Figure 25:
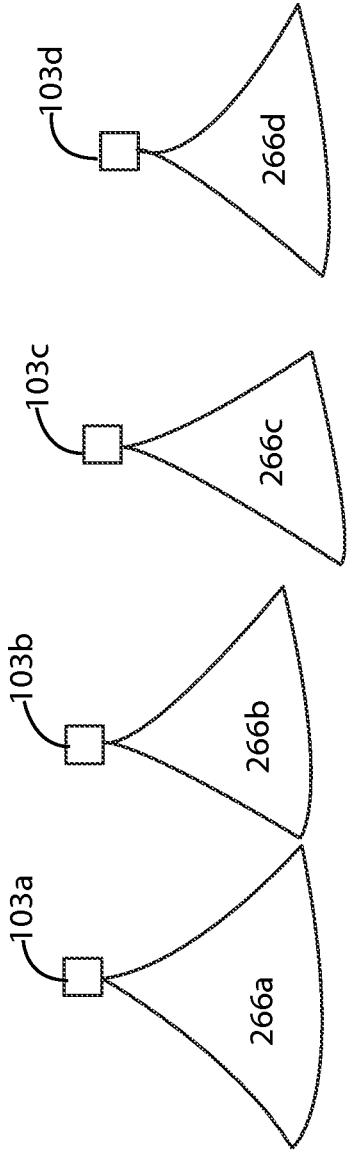
FIG. 25 is a schematic view of the fields-of-view provided by a bank of proximity sensors according to one embodiment of the invention.
Figure 26:
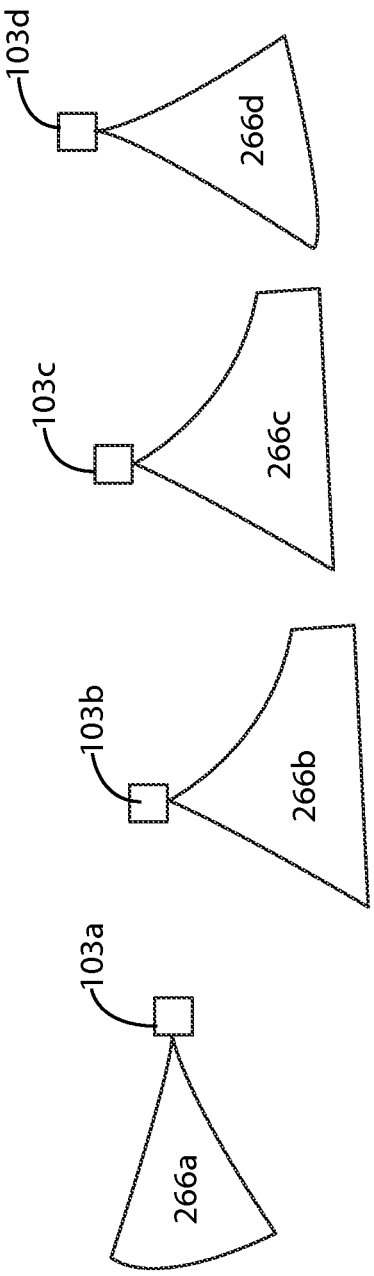
FIG. 26 is a schematic view of the fields-of-view provided by a bank of proximity sensors according to one embodiment of the invention.

As described above with respect to FIG. 17, the top portion 53 of the upper plenum 142 has, in one embodiment, four proximity sensors 103a, 103b, 103c, 103d that each work through triangulation to detect an object, i.e., user's hand(s), in the hand-receiving cavity 52. In one embodiment of the lavatory system 10, as shown particularly in FIG. 7, the sensors 103a, 103b, 103c, 103d are positioned adjacent the leading edge of the top portion of the 53 of the upper plenum 142. As described above, the sensors use triangulation to detect an object being presented to and present within the hand-receiving cavity 52. With additional reference to FIG. 25, the sensors 103a, 103b, 103c, 103d are configured and arranged to have non-overlapping fields-of-view (FOV) 266a, 266b, 266c, 266d, respectively. When a user's hand(s) are presented to the hand-receiving cavity 52, the leftmost sensor 103a first detects the presentment and provides a corresponding electrical signal to the microcontroller 78, which in turn provides a command signal to the hand dryer microcontroller 99. As described above, in one preferred embodiment, operation of the hand dryer is delayed by a preset value, e.g., 400 ms, upon detection of a user's hand being presented to the hand-receiving cavity.

The configuration of the hand-receiving cavity 52 allows a user to present his hand(s) for drying from the side of the hand-receiving cavity 52, such best illustrated in FIG. 2 or from front of the hand-receiving cavity 52, such as along arrow 268 of FIG. 9. In the case of the latter (front presentation), depending upon the lateral position of the user's hand(s), any of the sensors 103b or 103c may first detect the user's hand(s) and provide a corresponding activation signal, as described above. It has been found that when hand(s) are front-presented, as opposed to side-presented, the motor delay that is observed (which assumes a side-presentment to the hand-receiving cavity) is not long enough to avoid splashback. That is, a single motor delay based on side-presentment to the hand-receiving cavity can result in splashback onto the user when the user presents his hand(s) to the hand-receiving cavity 52 from the front.

Figure 35:
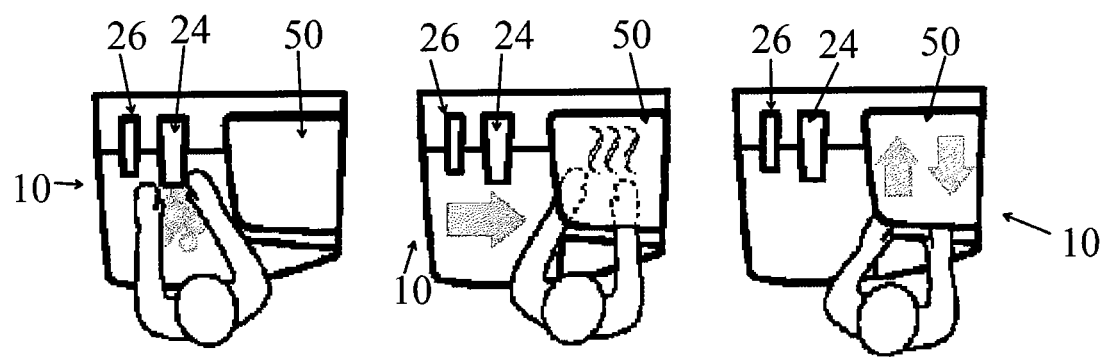
FIG. 35 is a top view of an embodiment of a lavatory system during use according to the present invention.

As discussed above, FIG. 35 shows the lavatory system 10 configured to allow a user to wash his/her hands with faucet 24 and soap dispenser 26 as shown on the left side of FIG. 35. The user may then dry his/her hands by moving from the faucet 24 entering the hand dryer 50 from the side. This motion is indicated with a horizontal arrow in the middle of FIG. 35. After the hands have entered the hand dryer 50, the user may move his/her hands back and forth in the hand-receiving cavity 52 (FIG. 2) as shown with back/forth arrows on the right side of FIG. 35.

Therefore, in accordance with another embodiment of the invention, one of two motor delays may be applied depending on how the user presents his hand(s) for drying. Referring again to FIG. 25, the sensors 103a, 103b, 103c, 103d are arranged such that the FOV 266a for sensor 103a will detect side-presentment to the hand receiving cavity 52. The FOVs 266b, 266c for the sensors 103b and 103c detect front-presentment of a user's hand(s) within the hand-receiving cavity 52, as described above. As sensor 103a only detects side-presentment to the hand-receiving cavity 52, actuation of the hand dryer motor 74 can be controlled based on which sensor detects presentment to the hand-receiving cavity. If sensor 103a is the first to detect, then side-presentment is assumed and the motor start delay will be 0-200 ms. If sensors 103b or 103c are first to detect, then front-presentment is assumed and the start delay will be 300 ms-800 ms.

For example, and in one preferred embodiment, if the first hand sensor 103 detects hand presentment to the hand-receiving cavity 52, the sensor 103a provides a corresponding electrical signal to the microcontroller 78. The microcontroller 78 includes software or firmware that distinguishes between an electrical signal being received from sensor 103a versus the other sensors 103b, 103c, 103d. With knowledge that the first object detection signal came from sensor 103a, the microcontroller 78 provides hand dryer motor activation signal to the hand dryer microcontroller 99. This motor activation signal results in the hand dryer motor being activated after a first preset delay period, e.g., 0-200 ms. However, if any of the other sensors 103b, 103c, 103d provides a first detection signal to the microcontroller 78, the hand dryer microcontroller 99 causes operation of the hand dryer motor 74 after a second preset delay period, e.g., 300-800 ms. Thus, in one embodiment, operation of the hand dryer motor is delayed more if a user presents his hand(s) to the hand-receiving cavity 52 from the front. This allows more time for the user to move his hands deeper into the hand-receiving cavity 52 before drying air is provided to the hand-receiving cavity. Preferably, the drying airstreams are provided at approximately wrist level in the hand-receiving cavity 52 and observing a longer delay before commencing drying when hands are front-presented allows the user sufficient time to insert his hands to the wrist level position before air is injected into the cavity 52.

It is contemplated that more than one microcontroller may be used to provide command signals to the hand dryer microcontroller 99. For example, the faucet sensor 25 may be coupled to a dryer sensor 100. Sensors 103a, 103b, 103c, 103d and 25 all may communicate with a shared microcontroller, similar to that shown in FIG. 21. This would allow the hand dryer motor 74 to begin operation at a standby speed, which is lower than full speed, when a hand is sensed by the faucet sensor 25. One or more of LEDs 108e-l may light up on the hand dryer to indicate the hand dryer motor is ramping up to the standby speed. After a hand is sensed by the dryer sensor 100, full speed operation of the hand dryer motor may commence. This function allows the dryer motor 74 to reach full speed with minimal wait time. Coupling the faucet sensor 25 to the dryer sensor 100 with multiple controllers would also allow the system to prevent accidental activation of the faucet when a user is operating the hand dryer, but allow a second user to operate the faucet while the first user is operating the hand dryer. In such an instance, a first user may operate the hand dryer. During this time, the faucet is prevented from activation. When a second user attempts to operate the faucet, faucet sensor 25 may use triangulation, and the controller may recheck the sensor signal multiple times confirming a second user present. This would then allow tandem operation of the hand dryer and faucet.

In accordance with an alternate embodiment of the present invention, the hand dryer 50 may include a second bank or set of sensors. These sensors are mounted along a side portion of the upper plenum and are designed to sense side-presentment of a user's hand(s) to the hand-receiving cavity. The afore-described sensors 103a, 103b, 103c, 103d are mounted adjacent the front of the hand-receiving cavity. Preferably, the respective sets of sensors have mutually exclusive fields-of-view (FOV) so that side-presentment of a user's hand(s) is not detected by the front-facing sensors and front-presentment of the user's hand(s) is not detected by the side-facing sensors.

Each set of sensors is operative to provide activation commands to the motor to commence operation of the motor. However, the front-facing sensors, upon detection of an object within their FOV, instruct the motor to commence activation after observing a longer delay period than that provided to the motor by the side-sensing sensors. In one embodiment, the longer delay period falls in the range of approximately 300-800 ms whereas the shorter delay period falls in the range of approximately 0-200 ms. These values are merely exemplary.

Figure 27:
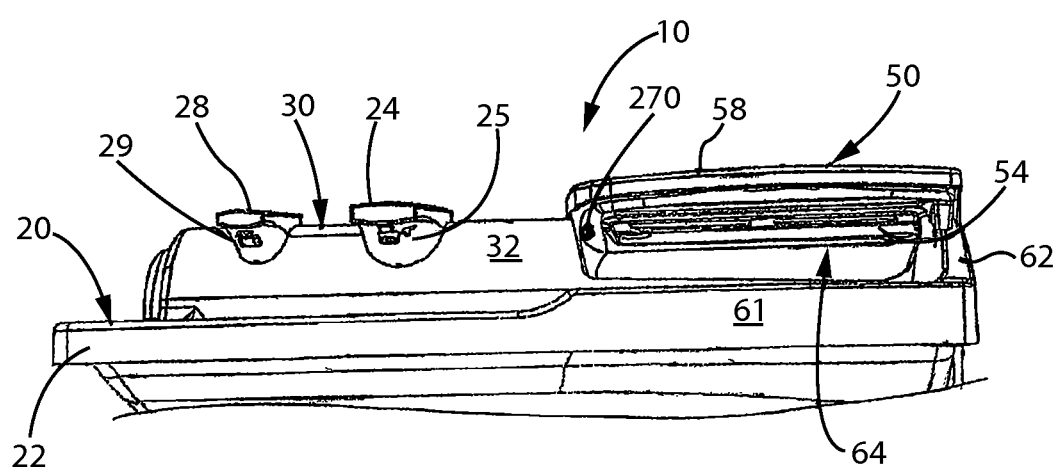
FIG. 27 is a front elevation cutaway view of a lavatory system according to a further embodiment of the present invention.

In accordance with yet another embodiment of the present invention, a single sensor is used to detect presentment of a user's hand(s) to the hand-receiving cavity 52. In this embodiment, which is shown in FIG. 27, a single sensor 270 with a side FOV is positioned at a corner of the top portion 53 (FIG. 1) near the upper plenum 142 (FIG. 10). The single sensor has a continuous side FOV that travels across the area adjacent the side of the hand-receiving cavity 52, the front side of the hand-receiving cavity, and the within the hand-receiving cavity. As the FOV is directed to the side and may also sense the front of the hand-receiving cavity, correlating the position of the FOV when the sensor 270 detects an object can be used to determine if the user is presenting his hand(s) in a side-presentment or a front-presentment manner. For example, in one embodiment, the sensor 270 has a pulsating emitter and a detector. The emitter is configured to iteratively pulse an IR beam beside, in front, and within the hand-receiving cavity. Based on which reflected pulse is detected by the detector, the microcontroller, e.g., microcontroller 78, can determine the presentment position of the user's hand(s) and control the hand dryer motor controller 99 accordingly. It is contemplated that other types of means may be used to sweep the FOV of the sensor 270 across the various detection zones.

In yet another embodiment that is similar to that described, it is contemplated that the sensors are sequentially pulsed to determine the position of the user's hand(s).

It will also be appreciated that the present invention can be embodied in a method of controlling operation of a hand dryer based on the position at which a user presents his hand(s) to a drying chamber having at least two points of ingress. In accordance with one embodiment of this method, the method includes iteratively scanning a first detection zone including the first point of ingress, iteratively scanning a second detection zone including the second point of ingress, supplying air with a first delay if an object is detected in the first detection zone, and supplying air with a second delay if an object is detected in the second detection zone, wherein the second delay is greater than the first delay. In one implementation, the first delay is a value between zero and 200 ms whereas the second delay is a value between 300-800 ms.

It will be appreciated that infrared sensors for detecting the ingress and egress of hands to and from the drying chamber is but one of a number of different object detecting technologies that could be used. For example, it is contemplated that camera and image processing technology, capacitive sensing, or passive infrared sensing could be used.

Further, it is contemplated that the invention could be used with a lavatory system having a single dryer situated between a pair of wash basins. It is also contemplated that sensors remote from the hand dryer could determine the direction of presentment. For example, sensors at or near the water faucet could detect motion of the hands after the water faucet has stopped dispensing water. If the hands are pulled away from the faucet the hand dryer could be caused to operate with a front-presentment to the hand drying cavity assumed. If the hands are moved sideways from the faucet, a side-presentment to the hand drying cavity could be presumed.

It is also noted that so-called "smart" technology could be incorporated into the lavatory system described herein to guide or sequence use of the various components of the lavatory system. For example, the lavatory system could be equipped with directional lights that guide (or at least remind) the user to apply soap and after washing, slide his hands into the drying chamber. Similarly, it is contemplated that the various components could be selectively locked out to prevent simultaneous activation of two components. For instance, it may be undesirable to have the water faucet capable of being activated when the dryer is forcing air into the drying chamber. If the water faucet were dispensing water while the dryer was active, it could lead to undesirable splashing of the water. Additionally, locking out certain components or features of the lavatory system may also sequence use of the lavatory system. For example, water faucet and dryer operation may be locked out until the soap dispenser has been activated. In such a situation, the aforementioned lights or similar devices could be used to direct the user to first apply soap to his hands before watering or drying the hands. Such a system may be highly preferred in food handling firms, such as restaurants.

It is, however, noted that in one embodiment the soap dispenser, water faucet, and hand dryer activation are controlled separately with independent controllers. Each of the aforementioned fixtures may function independently. In alternative embodiments, by interconnecting the controllers with wiring and software, the controllers may be programmed to communicate with each other.

Referring again to FIG. 16, in a preferred embodiment of the invention, a filter, i.e., HEPA filter 84, is provided within the motor housing 70 to filter the intake air. In a further embodiment, a filter sensor 272 is provided to monitor the condition of the filter 84. In one embodiment, the filter sensor 272 is a differential pressure (or vacuum) transducer that is located between the filter 84 and the intake to the motor 74, such as in intake cavity 274. The transducer measures the difference in pressure between atmospheric pressure and the vacuum in the intake cavity 274. As such, the filter sensor 272 is also fluidly connected to a vent hose 276 that is vented to atmosphere. The filter sensor 272 is connected to logic (not shown) of the motor control 98 in a conventional manner so that operation of the motor 74 can be controlled based on the condition of the filter 84. The filter sensor 272 can also be a non differential pressure or vacuum transducer. In this embodiment, the need for a hose or method of communicating two pressures is eliminated. In this case, the condition of the filter 84 is monitored in such a manner that the microcontroller (either 78 or 99) takes at least one vacuum/pressure measurement when the hand dryer 50 is not in use and again takes vacuum/pressure measurements when the hand dryer 50 is in use. Via computational methods, the microcontroller (either 78 or 99) calculates the difference in pressure/vacuum between the nonoperational and operational conditions of the hand dryer 50 and based upon this difference, the condition of the filter cleanliness can be determined. Further, an absolute pressure/vacuum measurement is attained during operation of the hand dryer 50 and because the resistance of filter 84 to air flow can vary within a given lot of material a predetermined maximum pressure loss or increase in vacuum can monitored so as to ensure that the hand dryer 50 performance is maintained at or above some minimum level. Furthermore, when an air filter is replaced 84, the microcontroller (either 78 or 99) can either automatically enter a programming mode or be instructed by the user to enter a programming mode such that the microcontroller (either 78 or 99) will automatically utilize the initial pressure/vacuum measurements with the new, unused filter to store the air pressure changes associated with the new filter.

In one preferred method of use, three actions are taken based on the output of the filter sensor 272 and thus, preferably, the output of the filter sensor 272 is compared by the logic to two different predefined levels. When the filter sensor 272 output is below a first vacuum level, no action is taken thereby indicating that the filter 84 is operating properly. However, if the filter sensor 272 output is at a first vacuum level, an indicator, i.e., light 278 (FIG. 1), is illuminated to indicate a "dirty filter" condition has been detected and, thus, signal a user or maintenance personnel that the filter 84 needs to be replaced. At a second vacuum level, as detected by the filter sensor 272, the motor controller 98 can shut down and disable operation of the motor 74 to prevent damage to the motor 74 or other components of the dryer.

In an alternate embodiment, a small tube (not shown) has an inlet end that is in fluid communication with the intake cavity 274 and an outlet end that is vented to atmosphere. In this embodiment, the filter sensor 272 is located in the tube. In this embodiment, it will be appreciated that the filter sensor 272 remotely monitors the pressure (vacuum) in the intake cavity.

While the preferred embodiments and best modes of utilizing the present invention have been disclosed above, other variations are also possible. For example, the materials, shape, and size of the components may be changed. Additionally, it is understood that a number of modifications may be made in keeping with the spirit of the system 10 of the present invention. For example, the system 10 may include features of the various embodiments set forth in PCT Application No. PCT/US2010/051647 filed on Oct. 6, 2010 and US Pub. Nos. US2008/0109956A1 published on May 15, 2008 and US2009/0077736A1 published on Mar. 26, 2009, and U.S. Ser. No. 13/267,429, all of which are expressly incorporated herein by reference. Further, a number of lavatory systems like the one shown in FIG. 1 can be mounted in a row or otherwise joined together as needed.

In addition to the above-described features and attributes, the present invention further provides for a lavatory system having one or more of the following features: (a) a color LED display 156, FIG. 2; (b) system diagnostics system 157, FIG. 16; (c) lavatory system communications system 158, FIG. 16; (d) active noise cancellation 159, FIG. 16; (e) various color and material combinations; (f) universal power supply; (g) sterilization features; (h) various nozzle designs; (i) plumbed dryer drain 161, FIG. 16; and (j) energy savings. Each of these features will be generally described below.

Incorporating a display and, preferably, a color LED display 156, FIG. 2, at one or more viewable portions of the lavatory system 10 facilitates the display of various types of information to an onlooker, such as a user or serviceperson. For example, the display could be used to display graphic or textual instructions to a user including, but not limited to, how to use the integrated lavatory system 10. That is, in addition to directing a user through the soaping, washing, and drying stations, the display could be used to provide guidance to a user as to how to lather soap, rinse, and dry. Diagnostic information, which will be described below, can be collected regarding use of the lavatory system 10, and can be displayed. It is contemplated that the display could be of the touch-screen type to facilitate user interaction therewith or include other I/O tools, such as buttons, and the like. It is further contemplated that the display could be used to display advertisements and similar consumer-driven notifications.

As noted above, the display could be used to display diagnostic information, such as to a serviceperson. In this regard, the lavatory system 10 may include an integrated data collection ("diagnostics") system that collects operational and performance data. For example, the diagnostics system may include sensors and the like that collect data regarding motor run time, soap level, period between use cycles, the period of each drying cycle, the time of day of each drying cycle, filter status, water used, water tray level indicator, and the like. Similarly, the display could be used to set operational parameters for the lavatory system, such as motor run time, faucet run time, volume of soap dispensed per cycle, and the like.

In one embodiment, the diagnostic information is acquired and stored and/or displayed locally, such as on the afore-described display. It is also contemplated that the diagnostic data could be transmitted to a centralized facility, such as a maintenance or operations room, for remote monitoring. This would allow service personnel to remotely monitor operation of multiple lavatory systems without having to visually inspect each lavatory system. The diagnostic information could be communicated across wired or wireless communication lines in a conventional manner.

One skilled in the art will appreciate that, in general, the greater the blowing force, the quicker hands may be dried in the drying cavity. However, an increased blowing force also increases the amount of noise emitted during a hand-drying cycle. When the user inserts their hands into the hand dryer, the noise level of the increased blowing force of the air is further amplified as the sound reflects off the user's hands back to their ears. To cancel or reduce the noise generated by the hand dryer, the lavatory system 10 preferably includes noise cancellation features. The noise cancellation features can include, but are not limited to, mechanical and/or electrical noise cancellation devices. For example, an electrical amplifier could be used to provide noise cancellation. The material makeup of the lavatory system could include sound-absorbing material or sound-absorbing panels. In this regard, it is contemplated that the lavatory system 10 could be manufactured from numerous materials, or combinations thereof, to provide a sterile yet noise abated washing environment. Furthermore, the noise cancellation devices may be designed or programmed in such a manner so as to mitigate only the audible frequencies typically generated by the hand dryer itself and/or the audible frequencies generated by the user upon insertion of their hands into the hand dryer. The selective cancellation of noise allows desirable sound to be heard, such as a discussion between people, the sound from a fire alarm, the sound over a public announcement (PA) system.

It is envisioned that the lavatory system 10 described herein could be used in a number of different geographical locations and, as such, additionally be equipped to handle different input voltages. Preferably, the lavatory system has a power circuit that allows the lavatory system 10 to be used universally without requiring significant modifications to the blower motor.

Reducing bacteria and germ growth in commercial lavatory systems is also important. To this end, the present invention contemplates that one or more sterilization features may be integrated into or used with the lavatory system 10. For example, ultraviolet (UV) waves could be emitted into the drying chamber or an ionization device could be employed. The energy from the UV waves may be used to sterilize the hand drying chamber and/or the wash basin only in the absence of a user so as to ensure a user is not exposed to UV radiation. For instance, a light detecting sensor could be employed in the hand dryer such that when the restroom is dark (e.g. during hours in which a store is closed or the restroom is unoccupied), the UV feature of the hand dryer turns on to sterilize the hand cavity basin.

The hand dryer mechanism can also serve as an air filter or air purifier. During periods in which the hand dryer is not drying an individual's hands, the hand dryer can continue to blow air at the same or another preferred velocity (or volume) A filter could be placed at some point in the communicative air path of the hand dryer mechanism such that air emitted through the nozzles 162, 164 is filtered. An alternative or secondary air path can be incorporated so that when the dryer is not functioning to dry an individual's hands, filtered air can be emitted in a more desirable or concealed direction. The filter mechanism can be of many forms such as a UV, electrostatic, HEPA or another appropriate filtering method. A bacteria or germ sensor could also be placed within the drying chamber or elsewhere on the lavatory system. The sensor could be operationally linked with an active air filter or purifier to initiate a filtration cycle.

In one embodiment of the invention, the nozzles 162, 164 are circular shaped but it is understood that the nozzle openings could have other types of shapes, such as ovals, trident, slots/slits, and the like. It is further contemplated that the nozzle body could have nozzle openings with different or non-uniform shapes and/or sizes. The lavatory system 10 could also be constructed so that the nozzles are oriented or angled at different areas within the drying chamber. Moreover, it is contemplated that the lavatory system 10 may have sensors within the drying chamber that detect the placement of the user's hands within the chamber. Selected ones of the nozzles could then be selectively opened and closed to direct drying air only through those nozzles that align with the placement of the user's hands within the drying chamber.

In yet another embodiment, the lavatory system 10 has a moisture detector or sensor that measures the wetness of the hands presented to the drying chamber. The run time and/or speed of the blower could be adjusted based on the detected hand wetness to optimize use of the hand dryer. In a similar manner, a sensor could be used to detect how soiled a user's hands are to control how much soap is dispensed by the soap dispenser and/or how much water is dispensed by the faucet.

In one embodiment of the lavatory system 10, a single drain 42 is used to drain water from the wash basin and drying chamber. Alternately, a second drain could be placed in the drying chamber.

Another alternate feature of the lavatory system 10 is the conversion of "wind" to electrical energy. This would allow air flow within the drying chamber to be collected, stored, and subsequently used to drive the blower motor. This could be accomplished by having air outlets within the drying chamber through which the blown air can pass to ultimately drive a small turbine or other device for the conversion of the wind energy to electrical energy.

As one skilled in the art may appreciate, there is a variety of electric blower motors and shapes that may be used in the present invention for the hand dryer. For example, one motor embodiment must be able to last for 0.5 to 1 million cycles over its life and be able to endure significant wear over that time period. The motor may be of brushed configuration or electronically commutated (brushless) dependent upon the hand dryer design requirements. Further, in one preferred embodiment of the invention, the dryer is configured to dynamically vary or reduce air pressure and/or air volume delivered by the electric blower motor within the unit and thus increase overall motor life.

In another embodiment, curvilinear brushes may be used like those used in some commercial hand dryer units. One such motor may be built to provide 68,000 activations per year wherein each activation is 15-30 seconds and the volume of air supplied to the hand cavity has a measured volume of approximately 333 cu. Inches, e.g., approximate dimensions of a length of 9.5 inches, depth of 10 inches, and heights of 3.5 inches.

To aid in maintaining the blower motor, one embodiment is provided with a cycle-counting software or other counter on board. Further, histogram cycle data, graphs, and/or charts may be provided for maintenance personal for each unit in each restroom in a given facility, e.g., the twelve units in each of the ten restrooms in an airport, conference center, office building, etc. This data could also be used by marketing personnel to determine hand dryer usage statistics. This data may be communicated in a variety of ways, some of which will be more fully described below.

In one embodiment, a pressure transducer may be provided for the motor to check for a dirty air intake filter. Alternatively, this may be provided on software on a chip on the mother board. Other maintenance usage filter life and performance data may be also be collected, communicated, and later displayed to maintenance personal.

In another embodiment, the lavatory system may have removable end caps on the left and right sides 115a, 115b (FIG. 1), allowing a maintenance person additional access to the electronics, plumbing, or other devices located within. Instead of end caps, additional lavatory systems may also be attached to the left and right sides of the lavatory system, giving the appearance of a single system with multiple basins, faucets, soap dispensers, and hand dryers. End caps 115a, 115b may be provided on the leftmost lavatory system and the rightmost lavatory system for a sealed, single unit appearance. The attached, multiple lavatory systems may share a common water supply manifold to simplify plumbing of the system.

As mentioned, a variety of communication means may be used to communicate problems or potential failure of certain components with the inventive system. In one embodiment, WIFI communications systems may transmit such data to maintenance personnel's cell phones, desk tops, laptops, notebooks, tablet PCs, or personal digital assistants, smart phones, etc. Moreover, a special software application or "App" may be provided for such devices for this purpose.

Figure 29:
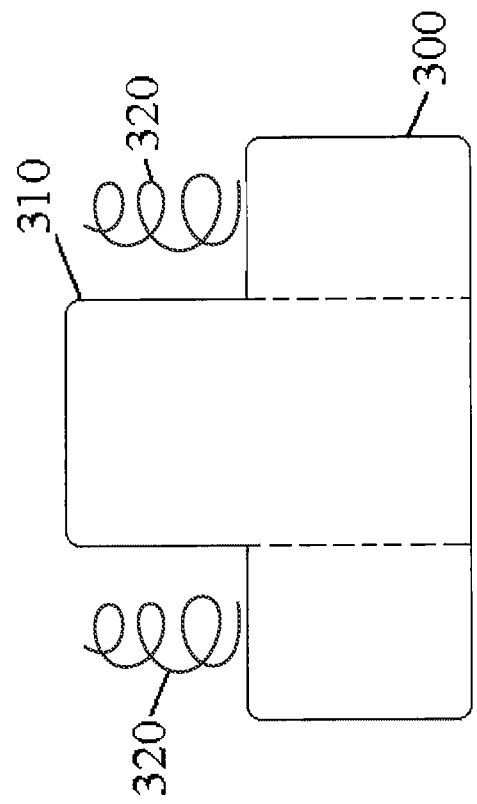
FIG. 29 is a side view of the helical brush motor according to one embodiment of the invention.
Figure 28:
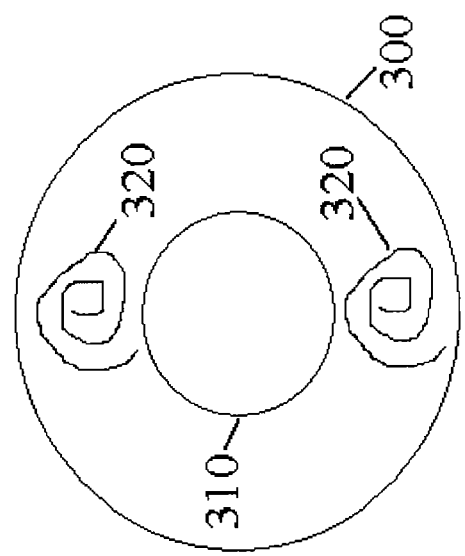
FIG. 28 is a top view of the helical brush motor according to one embodiment of the invention.

In another embodiment, the lavatory system may include an electric motor for powering the electric hand dryer that is equipped with a helical brush. As seen in FIGS. 5-9, the lavatory system 10 preferably includes an integral drying system, e.g., a hand dryer 50. The dryer 50 has a hand-receiving cavity 52 and a motor 74. The motor 74 may have helical brushes of the type shown in FIGS. 28 and 29. The motor housing 300 surrounds a spinning rotor 310. Helical shaped brushes 320 are positioned parallel to the rotor 310. The helix shape of the brushes 320 allows for longer brush life as the total length of the brush 320 is longer than a conventional, straight brush that would occupy the same space. A clock spring or constant force spring may be used to apply pressure against the brush 320, causing the brush 320 to contact the rotor 310. The helical shaped brushes 320 contact the rotor 310 at a perpendicular, or oblique angle. This causes a greater contact surface area between the brush 320 and the rotor. Increasing the surface area of the contact point lowers the amount of force per square inch on the brush, which lengthens service life. The constant rate spring may wrap around the rotor 310 in the space between the motor body 300 and rotor 310. As the constant rate spring always applies even force, the life of the brush may be accurately predicted. Because the helical brushes 320 occupy space in three dimensions, they have a much longer linear equivalent length. As the helical brush 320 wears, the constant rate spring advances it forward with a constant pressure. The helical brush 320 may be inserted into a cored-out mandrel. The mandrel may have a helical core which the brush 320 is inserted into. The mandrel may be held stationary, causing the brush 320 contact angle with the rotor 310 to always remain constant. Alternatively, the mandrel may be manufactured out of a sacrificial material. In this configuration, the mandrel and helical brush 320 are advanced in a rotating motion as one unit, keeping the contact angle of the brush 320 and the rotor 310 constant. The sacrificial material may then be consumed by frictional forces and heat at a rate even to brush wear. The disclosed helical brush 320 may be applied in any electric motor, not just the hand dryer 50 disclosed in FIGS. 5-9.

Figure 30:
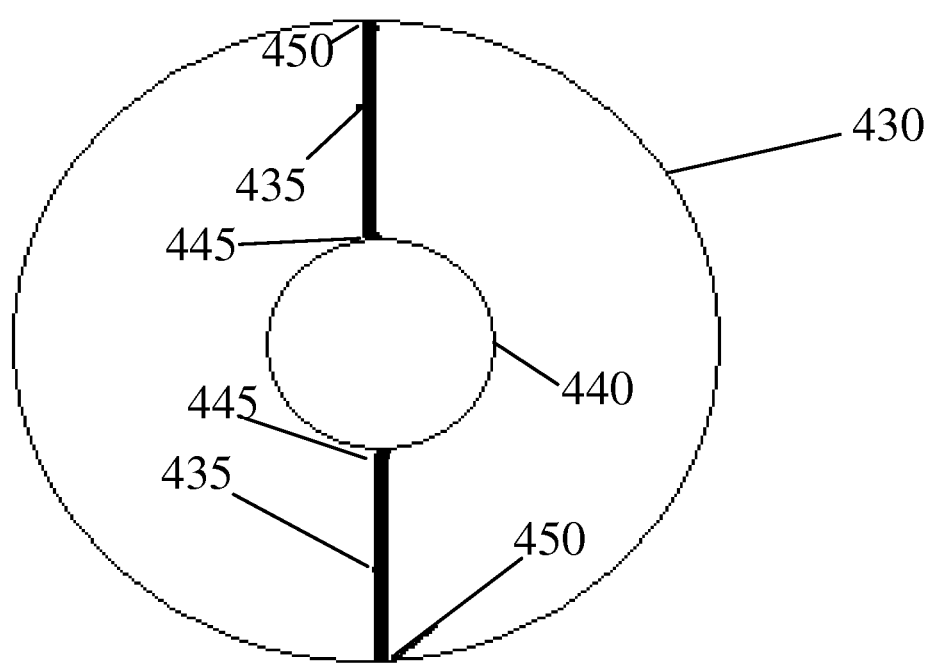
FIG. 30 is a pictorial view of a cross section of an electric motor according to the prior art.

FIG. 30 discloses the prior art, brushed motor which includes a motor body 430 and brushes 435. The brushes 435 contact the motor body at contact point 450 and contact the rotor 440 at contact point 445. A spring typically applies force to push the brush 435 against the rotor 440. As the rotor 440 spins when the motor is in operation the brushes 435 wear down. The spring advances the brush 435 forward to remain in contact with the rotor 440. Traditional spring pressures vary as the spring expands, making the force applied to the brush 435 inconsistent which causes uneven wear of the brushes 435. As the brushes 435 are linear, there is a limited amount of space the brush may occupy within the motor body 430.

Figure 31:
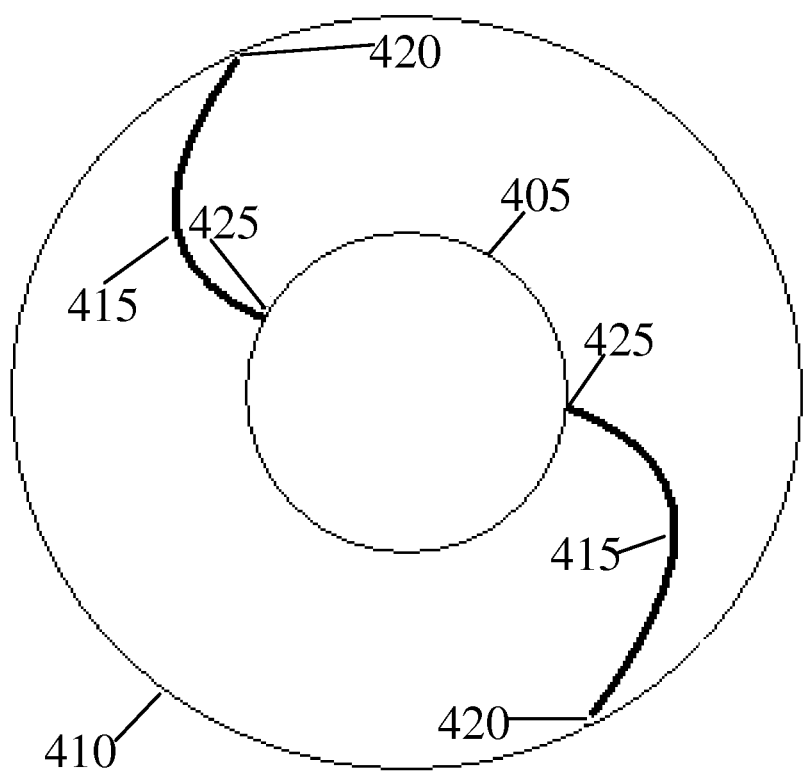
FIG. 31 is a pictorial view of a cross section of an embodiment of the inventive electric motor.

FIG. 31 discloses the inventive helical brush motor, preferably for a hand dryer used in a lavatory system. The motor body 410 surrounds a rotor 405 which rotates when the motor is operating. Three dimensional, helical brushes 415 may occupy space between the motor body 410 and rotor 405 in all three dimensions, thus forming a helical shape. The helical brushes 415 contact the motor body 410 at contact points 420. The contact points 420 may also include a constant rate spring. Constant rate springs, also called clock springs, apply the same spring pressure when they are at a maximum potential energy state and continue to apply the same pressure as they transfer stored potential energy to kinetic energy as they expand. The helical brush 415 contacts the rotor 405 at contact points 425.

Figure 32:
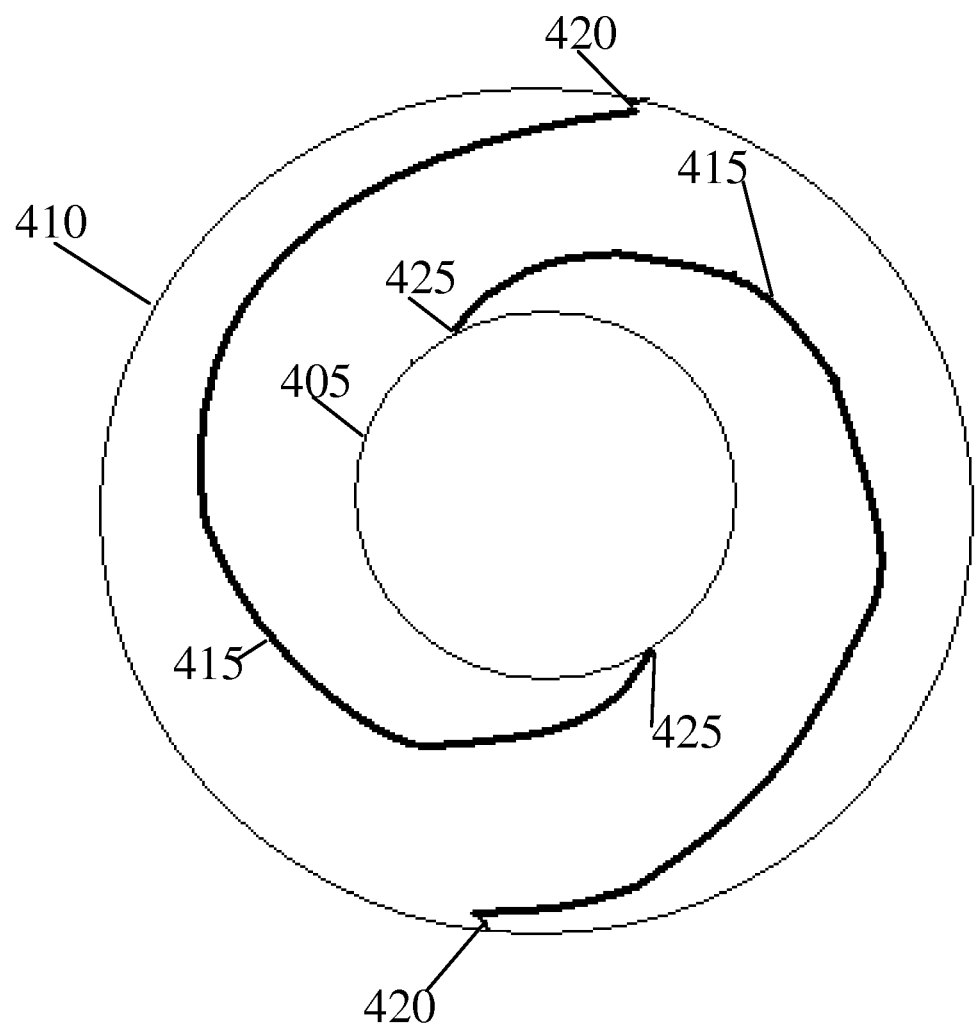
FIG. 32 is a pictorial view of a cross section of an alternate embodiment of the inventive electric motor.

FIG. 32 discloses another embodiment of the invention. Motor body 410 surrounds rotor 405. Helical brushes 415 surround the rotor 405. The amount the helical brushes 415 surround, or wraps around, the rotor 405 can be varied according to the amount of space between the motor body 410 and the rotor 405. The helical brushes 415 contact the motor body 410 at contact points 420 and the helical brushes 415 contact the rotor 405 at contact points 425. Contact points 420 include a not pictured clock spring, also referred to as a constant rate spring. The constant rate spring may wrap around the rotor 405 in the space between the motor body 410 and rotor 405. The constant rate spring will apply pressure forcing the helical brushes 415 against the rotor 405. As the constant rate spring always applies even force, the life of the brush may be accurately predicted, because the helical brushes 415 occupy space in three dimensions, they have a much longer linear equivalent length. As the helical brush 415 wears, the constant rate spring advances it forward with a constant pressure. Contact points 420 may include the constant rate spring or use additional electrical contact devices known in the electric motor art.

Figure 33:
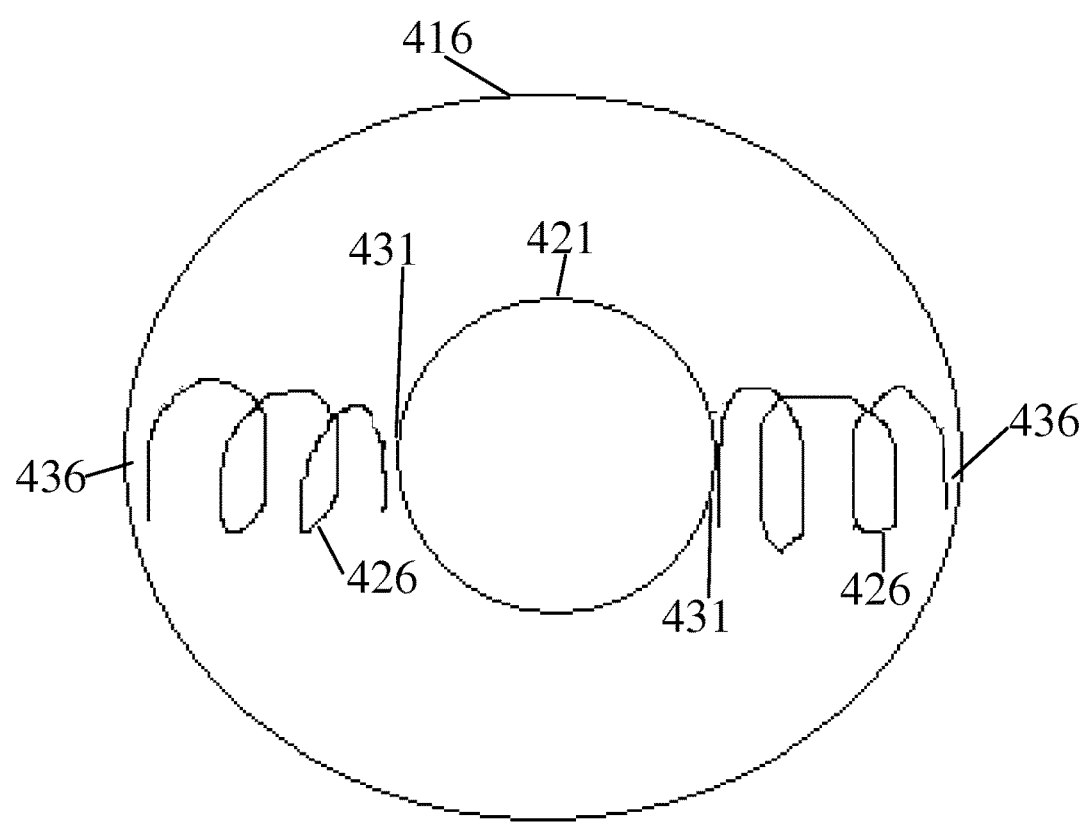
FIG. 33 is a pictorial view of a cross section of an alternate embodiment of the inventive electric motor.

Looking now to FIG. 33, an alternate embodiment of the helical brush 426 is shown. As opposed to having the helical brush 421 wrap around the rotor 421, the helix is formed at a perpendicular direction to the central, longitudinal axis of the rotor 421. Helical brushes 426 contact the rotor 421 at contact points 431 and contact the motor body 416 at contact points 436. The helical brushes 426 occupy similar space as the prior art brushes 435 in FIG. 30; however due to the helical shape, the brush has a much longer length. As a result, helical brush life is much longer than the prior art brush.

Figure 34:
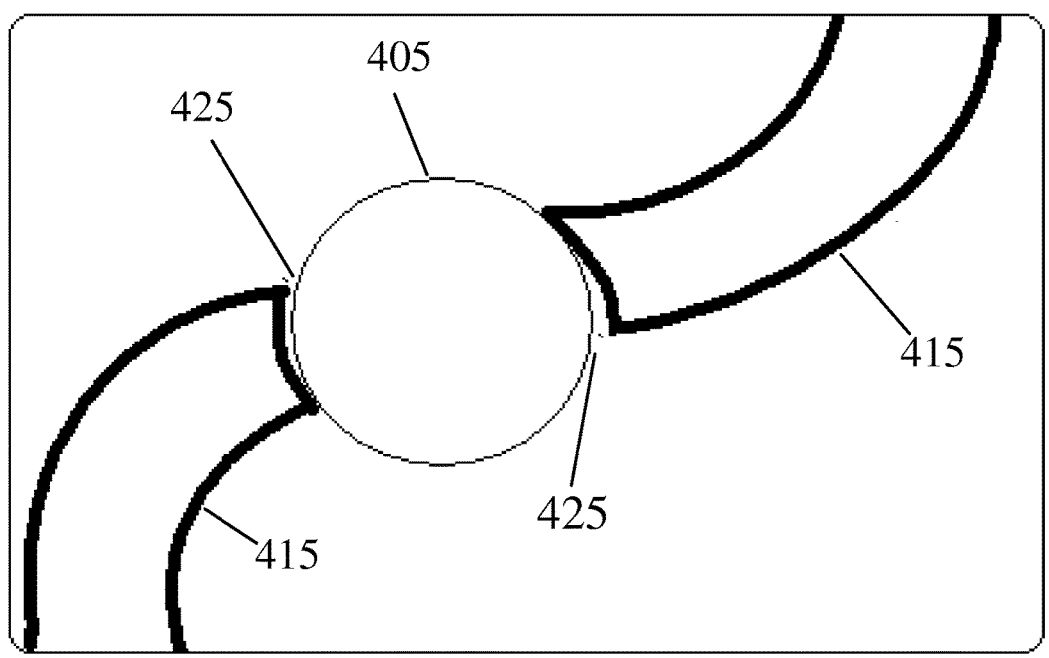
FIG. 34 is a close-up view of a cross section of an embodiment of the inventive electric motor detailing the contact between a rotor and a brush.

Transitioning to FIG. 34, a close up view of the contact point 425 between helical brushes 415 and rotor 405 is shown. This close up illustrates how any helical brush disclosed in any of the embodiments may contact a rotor. Only one point of the helical-shaped brush 415 contacts the rotor 405. As the helical brush 415 wears down, a constant force spring, also called clock spring, will continue to apply pressure to the helical brush 415, which keeps it in contact with the rotor 405.

An additional, alternate embodiment of the helical shaped brush motor may include a nested coil using two brushes. In this embodiment, two helical brushes would wrap around a rotor of an electric motor. The helical brushes may also each contact the rotor in one place and the helical brushes would also each make electrical contact with the motor body in one place. A constant rate spring would be placed within the motor body so as to apply even force of the helical brush throughout the helical brush's service life.

Thus, it is specifically intended that the present invention not be limited to the embodiments and illustrations contained herein, but includes modified forms of those embodiments including portions of the embodiments and combinations of elements of different embodiments as come within the scope of the following claims.

What is claimed is:

1. A lavatory system comprising:
   a basin including a water collecting area and a back splash;
   the back splash integrated with a soap dispenser and a faucet;
   a hand dryer integrated with the back splash and the water collecting area of the basin, the hand dryer having:
      a first plenum connected to the backs plash; and
      a second plenum connected to the water collecting area of the basin; and
   proximity sensors integrated with the soap dispenser, hand dryer, and faucet configured to activate the soap dispenser, hand dryer, and faucet, respectively, when an object is sensed with a triangulation algorithm for detecting an object or user's hand proximate to the soap dispenser, hand dryer, and faucet.

2. The lavatory system of claim 1, further comprising a LED display configured to display active information.

3. The lavatory system of claim 1, further comprising a first drain in the basin beneath the faucet and a second drain in the basin beneath the second plenum of the hand dryer.

4. The lavatory system of claim 1, further comprising an electric blower motor with a service life of 0.5 million to 1 million cycles over its service life.

5. The lavatory system of claim 1, further comprising a brushless blower motor configured to supply a pressurized air to the first and second plenums.

6. The lavatory system of claim 1, further comprising a blower motor configured to provide 68,000 activations per year, each activation enduring 15 to 30 seconds.

7. The lavatory system of claim 1, further comprising,
   a hand dryer microcontroller configured to control a plurality of LED lights and an electric blower motor for supplying air to the first and second plenums; and
   a plurality of proximity sensors connected to the first plenum for supplying input to the hand dryer microcontroller.

8. The lavatory system of claim 7, further comprising,
   a moisture sensor in communication with the hand dryer microcontroller for detecting a moisture content of a person's hands in proximity to the hand dryer; and
   a run time for the electric blower motor determined by the hand dryer microcontroller based on the moisture content.

9. The lavatory system of claim 1, further comprising,
   a flood relief portion in fluid communication with the basin and configured to prevent water in the basin from contacting the electric blower motor.

10. The lavatory system of claim 1, further comprising one of an ultraviolet light configured to disinfect an area in the basin and an ionization source configured to disinfect an area in the basin.

11. The lavatory system of claim 1, further comprising a plurality of nozzles within the first and second plenums, the plurality of nozzles being oriented with a plurality of angles and configured to prevent a water splashing onto a user.

12. A lavatory system comprising:
   a basin having an integrated water collecting area and a backsplash;
   the back-splash configured with a soap dispenser and a faucet;
   a hand dryer integrated with the backsplash and the integrated water collecting area of the basin;
   a first plenum connected to the backsplash;
   a second plenum connected to the integrated water collecting area of the basin; and
   a microcontroller programmed to control the hand dryer, soap dispenser, and faucet with a triangulation algorithm using a plurality of inputs from a plurality of proximity sensors configured to sense a person's hands proximate to the hand dryer, soap dispenser, and faucet.

13. The lavatory system of claim 12, further comprising a moisture sensor in communication with the microcontroller for detecting a moisture content of a person's hands in proximity to the hand dryer; and
   a run time determined by the microcontroller for the electric blower motor based on the moisture content.

14. The lavatory system of claim 12, further comprising a display screen attached to the lavatory system for displaying one of an active text based information and an active graphical information.

15. The lavatory system of claim 14, wherein the display screen is configured to display one of advertising and a time usage of the lavatory system.

16. The lavatory system of claim 12, further comprising a removable end cap on each side of the back splash, wherein the end cap may be removed for attaching a second lavatory system.

17. The lavatory system of claim 12, wherein the proximity sensors include at least one camera and the microcontroller is programmed with image processing to determine if a person's hands are proximate to the hand dryer.

18. The lavatory system of claim 12, further comprising an active noise cancellation system configured to cancel an acoustic noise produced by the lavatory system.

19. The lavatory system of claim 12 further comprising:
   a first plurality of nozzles within the first plenum, the plurality of nozzle oriented at a first angle;
   a second plurality of nozzle within the second plenum, the second plurality of nozzles oriented at a second angle;
   wherein the first plurality of nozzles is located closer to the user than the second plurality of nozzles; and
   wherein the second plurality of nozzles is located closer to the backsplash than the first plurality of nozzles.

20. A lavatory system comprising:
   a basin including a water collecting area and a backsplash;
   a hand dryer including a first plenum extending from the backsplash and a second plenum integrated with the water collecting area of the basin forming a drying cavity configured to receive a person's hands;
a faucet extending from the back splash;
a soap dispenser extending from the back splash;
a drain in the basin configured to receive a water from the faucet, a soap from the soap dispenser, and a liquid removed from the person's hands by the hand dryer;
a microcontroller programmed to control the lavatory system with a triangulation algorithm using a plurality of inputs from a plurality of proximity sensors, wherein the microcontroller delays an activation of the hand dryer when a person's hands are sensed by the proximity sensors for a set period of time;
a lavatory system cover beneath the basin configured to enclose a plumbing and a blower motor; and
a pair of end caps removably attached to a first and second side of the lavatory system configured to conceal attachments for additional lavatory systems.

* * * * *